US010192637B2

(12) United States Patent
Takemoto et al.

(10) Patent No.: US 10,192,637 B2
(45) Date of Patent: Jan. 29, 2019

(54) SPECIMEN ANALYZER AND SPECIMEN ANALYSIS METHOD

(71) Applicant: Sysmex Corporation, Kobe-shi, Hyogo (JP)

(72) Inventors: Seiji Takemoto, Kobe (JP); Takeshi Komoto, Kobe (JP); Hideki Hirayama, Kobe (JP); Takashi Yoshida, Kobe (JP); James Ausdenmoore, Elgin, IL (US)

(73) Assignee: SYSMEX CORPORATION, Kobe-shi (JP)

( * ) Notice: Subject to any disclaimer, the term of this patent is extended or adjusted under 35 U.S.C. 154(b) by 0 days.

(21) Appl. No.: 15/609,711

(22) Filed: May 31, 2017

(65) Prior Publication Data

US 2018/0349564 A1    Dec. 6, 2018

(51) Int. Cl.
| | |
|---|---|
| *G06F 3/12* | (2006.01) |
| *G16H 15/00* | (2018.01) |
| *G06F 3/14* | (2006.01) |
| *G01N 33/49* | (2006.01) |
| *G01N 33/487* | (2006.01) |
| *H04N 1/00* | (2006.01) |

(52) U.S. Cl.
CPC ....... *G16H 15/00* (2018.01); *G01N 33/48792* (2013.01); *G01N 33/49* (2013.01); *G06F 3/1208* (2013.01); *G06F 3/1243* (2013.01); *G06F 3/1288* (2013.01); *G06F 3/1407* (2013.01)

(58) Field of Classification Search
CPC .... G06F 3/1208; G06F 3/1243; G06F 3/1288; G06F 3/1407; G01N 35/00594; G01N 35/00603; G01N 35/1079; G01N 35/1083

USPC .................................................. 358/1.1–1.18
See application file for complete search history.

(56) References Cited

U.S. PATENT DOCUMENTS

| | | | |
|---|---|---|---|
| 5,587,129 A * | 12/1996 | Kurosaki | G01N 35/00603 422/63 |
| 6,635,488 B1 | 10/2003 | Saito et al. | |
| 6,772,650 B2 | 8/2004 | Ohyama et al. | |
| 6,938,502 B2 | 9/2005 | Tanoshima et al. | |
| 8,474,692 B2 | 7/2013 | Mizumoto et al. | |
| 8,790,577 B2 | 7/2014 | Mizumoto et al. | |
| 8,967,459 B2 | 3/2015 | Mizumoto et al. | |
| 9,297,819 B2 | 3/2016 | Ausdenmoore et al. | |
| 9,317,653 B2 | 4/2016 | Ausdenmoore et al. | |
| 9,395,378 B2 | 7/2016 | Mizumoto et al. | |
| 2006/0029520 A1 | 2/2006 | Tanoshima et al. | |
| 2008/0161661 A1 * | 7/2008 | Gizewski | A61B 5/0059 600/306 |

(Continued)

FOREIGN PATENT DOCUMENTS

| | | |
|---|---|---|
| JP | H06-027117 A | 2/1994 |
| JP | 2001-004634 A | 1/2001 |

(Continued)

*Primary Examiner* — Gabriel Garcia
(74) *Attorney, Agent, or Firm* — Metrolexis Law Group, PLLC

(57) ABSTRACT

This specimen analyzer includes: an analysis unit which analyzes a specimen collected from a subject; a print unit which prints on a print sheet; a display unit which displays an operation screen; and a controller which performs control of causing the print unit to print an analysis result of the analysis unit, and prohibiting the display unit from displaying the analysis result.

36 Claims, 58 Drawing Sheets

(56) References Cited

U.S. PATENT DOCUMENTS

2013/0023006 A1    1/2013   Ausdenmoore et al.
2013/0317773 A1*   11/2013   Oda ........................ G01D 3/00
                                                                      702/104
2015/0125938 A1    5/2015   Terashima et al.

FOREIGN PATENT DOCUMENTS

| | | |
|---|---|---|
| JP | 2001-124781 A | 5/2001 |
| JP | 2003-083960 A | 3/2003 |
| JP | 2009-068979 A | 4/2009 |
| JP | 2012-073164 A | 4/2012 |
| JP | 2013-024880 A | 2/2013 |
| JP | 2013-024881 A | 2/2013 |
| JP | 2013-024882 A | 2/2013 |
| JP | 2014-145685 A | 8/2014 |
| JP | 2015-163904 A | 9/2015 |

\* cited by examiner

Auto Rinse

Remove Clog

| Any Clinic
Anytown, State | 301 |

| Instrument type XW100
Selial # | 302 |

| Date Feb 25, 2016
Time 08:00 AM | 303 |
| Operator | 304 |

| Patient ID          0000000 | 305 |
| Patient DOB Jun 24, 1965 | 306 |

307

| WBC | **** | ALERT L |
| RBC | 4.81 x 10⁶/μL | |
| HGB | 24.3 x g/dL | ALERT H |
| HCT | 43.1 % | |
| PLT | **** | ALERT L |

| #Neut | **** | WBC Diff |
| %Neut | **** | WBC Diff |

| #Lymph | **** | WBC Diff |
| %Lymph | **** | WBC Diff |

| #OtherWBC | **** | WBC Diff |
| %OtherWBC | **** | WBC Diff |

| MCV | 81.6 fL | Low |
| MCH | 29.8 pg | |
| MCHC | 35.6 g/dL | |
| RDW SD | 41.9 fL | |
| RDW CV | 14.0 % | |
| MPV | 10.0 fL | |

102a(102)    102b(102)

308

NOTES

RECOMMEND FURTHER TESTING — 311

Potential ALERT Valve should be
acted upon IMMEDIATELY — 312

Adult Reference Ranges

| WBC | 3.9 – 10.4 x 10³/μL |
| RBC | 3.71 – 5.52 x 10⁶/μL |
| HGB | 10.9 – 16.7g/dL |
| HCT | 32.5 – 49.4% |
| PLT | 148 – 382 x 10³/μL |
| %Neut | 46.4 – 76.9% |
| %Lymph | 14.7 – 45.9% |
| %OtherWBC | 3.2 – 16.9% |
| MCV | 82.5 – 98.0 fL |
| MCH | 26.1 – 32.8 pg |
| MCHC | 30.7 – 35.9 g/dL |
| RDW SD | 39.1 – 51.6 fL |
| RDW CV | 11.8 – 15.8 % |
| MPV | 8.5 – 13.3 fL |

- - - End·Report - - -

| | | 313 | 102a(102) | 102b(102) |

300

| | | 313 | 102a(102) 102b(102) |
|---|---|---|---|
| 307 → | WBC | **** | ALERT L ---- 315 |
| | RBC | 4.81 x 10⁶/μL | |
| | HGB | 24.3 x g/dL | ALERT H ---- 315 |
| | HCT | 43.1 % | |
| | PLT | **** | ALERT L ---- 315 |
| 313 ---- | #Neut | **** | WBC Diff |
| | %Neut | **** | WBC Diff |
| | #Lymph | **** | WBC Diff |
| | %Lymph | **** | WBC Diff — 102b(102) |
| | #OtherWBC | **** | WBC Diff |
| | %OtherWBC | **** | WBC Diff — 102b(102) |
| | MCV | 81.6 fL | Low ---- 314 |
| | MCH | 29.8 pg | ← 102a(102) |
| | MCHC | 35.6 g/dL | |
| | RDW SD | 41.9 fL | |
| | RDW CV | 14.0 % | |
| | MPV | 10.0 fL | |

FIG.51

| ANALYSIS RESULTS | | PERMISSION/ PROHIBITION OF OUTPUT | PRINT EMBODIMENTS WHEN OUTPUT IS PROHIBITED |
|---|---|---|---|
| OUTSIDE FIRST DETERMINATION RANGE | | | |
| | NUMERICAL INFORMATION | OUTPUT PROHIBITED | SUBSTITUTE INDICATION |
| | CONTENT OF ERROR | OUTPUT PROHIBITED | NOT DISPLAYED |
| WITHIN NORMAL RANGE (Reference Range) | | | |
| | NUMERICAL INFORMATION | OUTPUT PERMITTED | — |
| | CONTENT OF ERROR | — | — |
| WITHIN FIRST ERRONEOUS RANGE (High or Low) | | | |
| INITIAL TEST | NUMERICAL INFORMATION | OUTPUT PROHIBITED | PROHIBIT OUTPUT OF PRINTED MATTER |
| | CONTENT OF ERROR | OUTPUT PROHIBITED | |
| RETEST RESULTS DETERMINED AS MISMATCHED | NUMERICAL INFORMATION | OUTPUT PROHIBITED | SUBSTITUTE INDICATION |
| | CONTENT OF ERROR | OUTPUT PERMITTED | — |
| RETEST RESULTS DETERMINED AS MISMATCHED | NUMERICAL INFORMATION | OUTPUT PERMITTED | — |
| | CONTENT OF ERROR | OUTPUT PERMITTED | — |
| WITHIN SECOND ERRONEOUS RANGE (ALERT H or ALERT L) | | | |
| WITHIN SECOND DETERMINATION RANGE | NUMERICAL INFORMATION | OUTPUT PROHIBITED | SUBSTITUTE INDICATION |
| | CONTENT OF ERROR | OUTPUT PERMITTED | — |
| OUTSIDE SECOND DETERMINATION RANGE | NUMERICAL INFORMATION | OUTPUT PERMITTED | — |
| | CONTENT OF ERROR | OUTPUT PERMITTED | — |
| CONTENT OF ERROR | | | |
| | NUMERICAL INFORMATION | OUTPUT PROHIBITED | SUBSTITUTE INDICATION |
| | CONTENT OF ERROR | OUTPUT PERMITTED | — |

FIG.52

| | LINEARITY GUARANTEE RANGE |
|---|---|
| WBC | 1.0 – 99.9 (×10³/μL) |
| RBC | 0.30 – 7.00 (×10⁶/μL) |
| HGB | 1 – 250 (g/L) |
| HCT | 10.0 – 60.0 (%) |
| PLT | 10 – 999 (×10³/μL) |

—350

|  | Pediatric (≥2 to <12 years of age) | | | | |
|---|---|---|---|---|---|
|  | ALERT LOW | Low | Reference Range | High | ALERT HIGH |
| WBC(×10³/μL) | 1.0-2.9 | 3.0-4.7 | 4.8-13.5 | 13.6-50.0 | 50.1-63.2 |
| RBC(×10⁶/μL) | – | 0.30-4.10 | 4.20-5.40 | 5.50-7.00 | – |
| HGB(g/dL) | 0.1-9.9 | 10.0-10.4 | 10.5-16.0 | 16.1-24.0 | 24.1-25.0 |
| HCT (%) | 10.0-24.9 | 25.0-28.9 | 29.0-48.0 | 48.1-60.0 | – |
| PLT (×10³/μL) | 10-99 | 100-162 | 163-369 | 370-999 | – |
| %Neut (%) | – | 0.0-34.9 | 35.0-76.0 | 76.1-100.0 | – |
| #Neut (×10³/μL) | – | 1.0-1.8 | 1.9-8.6 | 8.7-63.2 | – |
| %Lymph (%) | – | 0.0-19.9 | 20.0-54.0 | 54.1-100.0 | – |
| #Lymph (×10³/μL) | – | – | 1.0-7.2 | 7.3-63.2 | – |
| %OtherWBC (%) | – | – | 0.0-19.0 | 19.1-100.0 | – |
| #OtherWBC(×10³/μL) | – | – | 1.0-2.2 | 2.3-63.2 | – |
| MCV (fL) | – | 0.0-75.9 | 76.0-99.0 | 99.1-999.9 | – |
| MCH (pg) | – | 0.0-25.5 | 25.6-32.2 | 32.3-999.9 | – |
| MCHC (g/dL) | – | 0.0-32.1 | 32.2-36.5 | 36.6-999.9 | – |
| RDW CV (%) | – | 0.0-35.0 | 35.1-46.1 | 46.2-100.0 | – |
| RDW SD(fL) | – | 0.0-11.5 | 11.6-14.4 | 14.5-250.0 | – |
| MPV (fL) | – | 0.0-9.3 | 9.4-12.4 | 12.5-40.0 | – |

360(373)　372　371　372　373

| | Adolescents (≥12 to <21 years of age) | | | | |
|---|---|---|---|---|---|
| | ALERT LOW | Low | Reference Range | High | ALERT HIGH |
| WBC($\times 10^3/\mu$L) | 1.0-2.9 | 3.0-4.7 | 4.8-10.8 | 10.9-50.0 | 50.1-63.2 |
| RBC($\times 10^6/\mu$L) | - | 0.30-4.10 | 4.20-6.10 | 6.20-7.00 | - |
| HGB(g/dL) | 0.1-9.9 | 10.0-11.9 | 12.0-18.0 | 18.1-24.0 | 24.1-25.0 |
| HCT (%) | 10.0-24.9 | 25.0-36.9 | 37.0-52.0 | 52.1-60.0 | - |
| PLT ($\times 10^3/\mu$L) | 10-99 | 100-162 | 163-369 | 370-999 | - |
| %Neut (%) | - | 0.0-39.9 | 40.0-80.0 | 80.1-100.0 | - |
| #Neut ($\times 10^3/\mu$L) | - | 1.0-1.8 | 1.9-8.6 | 8.7-63.2 | - |
| %Lymph (%) | - | 0.0-14.9 | 15.0-40.0 | 40.1-100.0 | - |
| #Lymph ($\times 10^3/\mu$L) | - | - | 1.0-3.9 | 4.0-63.2 | - |
| %OtherWBC (%) | - | - | 0.0-19.0 | 19.1-100.0 | - |
| #OtherWBC($\times 10^3/\mu$L) | - | - | 1.0-2.0 | 2.1-63.2 | - |
| MCV (fL) | - | 0.0-79.9 | 80.0-99.0 | 99.1-999.9 | - |
| MCH (pg) | - | 0.0-25.5 | 25.6-32.2 | 32.3-999.9 | - |
| MCHC (g/dL) | - | 0.0-32.1 | 32.2-36.5 | 36.6-999.9 | - |
| RDW CV (%) | - | 0.0-35.0 | 35.1-46.1 | 46.2-100.0 | - |
| RDW SD(fL) | - | 0.0-11.5 | 11.6-14.4 | 14.5-250.0 | - |
| MPV (fL) | - | 0.0-9.3 | 9.4-12.4 | 12.5-40.0 | - |

| | Adult (≥21 years of age) | | | | |
|---|---|---|---|---|---|
| | ALERT LOW | Low | Reference Range | High | ALERT HIGH |
| WBC (×10³/μL) | 1.0-2.9 | 3.0-3.8 | 3.9-10.4 | 10.5-50.0 | 50.1-63.2 |
| RBC (×10⁶/μL) | - | 0.30-3.70 | 3.71-5.52 | 5.53-7.00 | - |
| HGB (g/dL) | 0.1-9.9 | 10.0-10.8 | 10.9-16.7 | 16.8-24.0 | 24.1-25.0 |
| HCT (%) | 10.0-24.9 | 25.0-32.4 | 32.5-49.4 | 49.5-60.0 | - |
| PLT (×10³/μL) | 10-99 | 100-147 | 148-382 | 383-999 | - |
| %Neut (%) | - | 0.0-46.3 | 46.4-76.9 | 77.0-100.0 | - |
| #Neut (×10³/μL) | - | 1.0-2.1 | 2.2-7.1 | 7.2-63.2 | - |
| %Lymph (%) | - | 0.0-14.6 | 14.7-45.9 | 46.0-100.0 | - |
| #Lymph (×10³/μL) | - | - | 1.0-3.4 | 3.5-63.2 | - |
| %OtherWBC (%) | - | 0.0-3.1 | 3.2-16.9 | 17.0-100.0 | - |
| #OtherWBC(×10³/μL) | - | - | 1.0-1.2 | 1.3-63.2 | - |
| MCV (fL) | - | 0.0-82.4 | 82.5-98.0 | 98.1-999.9 | - |
| MCH (pg) | - | 0.0-26.0 | 26.1-32.8 | 32.9-999.9 | - |
| MCHC (g/dL) | - | 0.0-30.6 | 30.7-35.9 | 36.0-999.9 | - |
| RDW CV (%) | - | 0.0-39.0 | 39.1-51.6 | 51.7-100.0 | - |
| RDW SD (fL) | - | 0.0-11.7 | 11.8-15.8 | 15.8-250.0 | - |
| MPV (fL) | - | 0.0-8.4 | 8.5-13.3 | 13.4-40.0 | - |

```
        313   313   102
300 →   WBC   ****         ALERT L  — 315
        RBC   4.81 x 10⁶/μL
        HGB   ****         ALERT H  — 315
307 →   HCT   43.1 %
        PLT   ****         ALERT L  — 315
        313

#Neut     ****     WBC Diff
        %Neut     ****     WBC Diff

#Lymph    ****     WBC Diff
        %Lymph    ****     WBC Diff

#OtherWBC ****     WBC Diff
        %OtherWBC ****     WBC Diff
```

FIG.57

```
300 →   RBC    4.81 x 10⁶/μL  ← 102
        HCT    43.1 %         ← 102

MCV    81.6 fL     Low  — 314

307 →   MCH    29.8 pg

MCHC   35.6 g/dL

RDW SD 41.9 fL

RDW CV 14.0 %

MPV    10.0 fL

NOTES
        ─────────────────────────
        RECOMMEND FURTHER TESTING  ← 311

308 →   Potential ALERT Valve should be  ← 312
        acted upon IMMEDIATELY
```

FIG.58

| ANALYSIS RESULTS | | FIRST MODIFIED EXAMPLE | SECOND MODIFIED EXAMPLE |
|---|---|---|---|
| OUTSIDE FIRST DETERMINATION RANGE | | | |
| | NUMERICAL INFORMATION | OUTPUT PROHIBITED (SUBSTITUTE INDICATION) | OUTPUT PROHIBITED (NOT DISPLAYED) |
| | CONTENT OF ERROR | OUTPUT PROHIBITED | NOT DISPLAYED |
| WITHIN NORMAL RANGE (Reference Range) | | | |
| | NUMERICAL INFORMATION | OUTPUT PERMITTED | OUTPUT PERMITTED |
| | CONTENT OF ERROR | — | — |
| WITHIN FIRST ERRONEOUS RANGE (High or Low) | | | |
| | NUMERICAL INFORMATION | OUTPUT PROHIBITED (SUBSTITUTE INDICATION) | OUTPUT PROHIBITED (NOT DISPLAYED) |
| | CONTENT OF ERROR | OUTPUT PERMITTED | NOT DISPLAYED |
| WITHIN SECOND ERRONEOUS RANGE (= WITHIN SECOND DETERMINATION RANGE) (ALERT H or ALERT L) | | | |
| | NUMERICAL INFORMATION | OUTPUT PROHIBITED (SUBSTITUTE INDICATION) | OUTPUT PROHIBITED (NOT DISPLAYED) |
| | CONTENT OF ERROR | OUTPUT PERMITTED | NOT DISPLAYED |
| FRACTIONATION ERROR | | | |
| | NUMERICAL INFORMATION | OUTPUT PROHIBITED (SUBSTITUTE INDICATION) | OUTPUT PROHIBITED (NOT DISPLAYED) |
| | CONTENT OF ERROR | OUTPUT PERMITTED | NOT DISPLAYED |

…

SPECIMEN ANALYZER AND SPECIMEN ANALYSIS METHOD

BACKGROUND

Field of Invention

The invention relates to a specimen analyzer and a specimen analysis method.

A specimen analyzer, which analyzes a specimen collected from a subject, outputs analysis results used for, e.g., diagnosis in clinical examination. For this reason, when analysis results are outputted to a user such as an operator of the apparatus, the analysis results are desired to be correctly recognized by the user.

Japanese Patent Application Publication No. 2003-83960 discloses a specimen analyzer which includes a display apparatus made up of a liquid crystal display and a touch panel, and which outputs analysis results to the display apparatus. Since a display screen of the display apparatus has a limited size, Japanese Patent Application Publication No. 2003-83960 discloses a technique of switching the display of the analysis results between a mode which displays screen 901 with small font size, and a mode which displays the analysis results divided on multiple screens 902, as illustrated in FIG. 61.

However, small font size on the display screen increases the risk that the user erroneously recognizes the analysis results because the content of the analysis results are hard to see. On the other hand, in the case of displaying the analysis results divided on multiple screens, there is possibility that the user may overlook some of the analysis results because the user does not notice there are multiple screens. The problem of a high possibility of erroneously recognizing the analysis results or overlooking the analysis results is particularly serious in a small, simplified specimen analyzer which has a small display screen. Given the above circumstances, it is desired to prevent erroneous recognition of analysis results attributed to low visibility and overlooking of analysis results by the user.

SUMMARY OF INVENTION

The invention is aimed at preventing erroneous recognition of analysis results attributed to low visibility and overlooking of analysis results by a user, even in the case of a small display screen.

Specimen analyzer (100) according to a first aspect of the invention includes: analysis unit (10) which analyzes specimen (101) collected from a subject; print unit (20) which prints on a print sheet; display unit (30) which displays an operation screen; and controller (40) which performs control of causing print unit (20) to print analysis result (102) of analysis unit (10), and prohibiting display unit (30) from displaying analysis result (102).

As described above, specimen analyzer (100) according to the first aspect includes controller (40) which performs control of causing print unit (20) to print analysis result (102) of analysis unit (10), and prohibiting display unit (30) from displaying analysis result (102). Thus, analysis results (102) are not displayed by display unit (30) but printed on print sheet (50) by print unit (20). Although the size of the display screen displayable at one time by display unit (30) is limited, the print area of print unit (20) can be adjusted as desired by, for example, changing the size of the print sheet. Thus, it is possible to print analysis results (102) without making the font size small. Additionally, also in the case of e.g. printing analysis results (102) on more than one print sheet (50), the user more easily recognizes the presence of more than one printed sheet by touching the printed sheets, unlike the case of switching screens. As a result, it is possible to prevent erroneous recognition of analysis results (102) attributed to low visibility and overlooking of analysis results (102) by the user, even in the case of a small display screen. There is a case where the operator of the apparatus directly communicates analysis results (102) to the ordering doctor or the like. In that case, by printing analysis results (102), the user such as an operator can hand in printed sheet (300) to the ordering doctor or the like without any modifications. Thus, miscommunication of analysis results (102) to the ordering doctor can be prevented.

In specimen analyzer (100) according to the first aspect described above, it is preferable that print unit (135) be capable of changing a size of print sheet (136), and print analysis result (102) on the same surface of a single piece of print sheet (136). In such a configuration, analysis results (102) are printed on one piece of print sheet (136) in one page. For this reason, it is possible to prevent a situation where e.g. the user overlooks the print content on the back side in the case of double-side printing and where the user finds it hard to recognize the content of analysis results (102) in the case of printing on multiple print sheets (136), and thus to easily and surely recognize all of analysis results (102) at one sight. Furthermore, when printing on one piece of print sheet (136) in one page, it is possible to print analysis results (102) on appropriate-sized print sheet (136) even when the print amount is large or small, depending on the content of analysis results (102).

In this case, it is preferable that print unit (135) include sheet set unit (135a) which holds print sheet (136) which is elongated, and that print unit (135) change the size of print sheet (136) by printing on an area of print sheet (136) with any length depending on a print amount. Here, print sheet (136) which is elongated is a sheet with its length long in a predetermined direction, and includes, for example, roll paper and a folded sheet. This configuration makes it possible to print analysis results (102) in any print amount by merely adjusting the length of the print area on same print sheet (136). This therefore eliminates the necessity of preparing several types of print sheets (136) with different sheet sizes, simplifying the apparatus configuration.

In specimen analyzer (100) according to the first aspect described above, it is preferable that analysis unit (120) perform analysis on analysis items, and print unit (135) print analysis result (102) for each of the analysis items. This configuration makes it possible to collectively recognize analysis results (102) of the multiple analysis items. Here, in a case where analysis results (102) of the multiple analysis items are displayed by display unit (131), the amount of information increases. This increases the risk of overlooking due to the necessity of displaying them in multiple screens. When analysis results (102) of the multiple analysis items are printed on print sheet (136), it is possible to prevent overlooking of analysis results (102) even when there is a large amount of information.

In specimen analyzer (100) according to the first aspect described above, it is preferable that in addition to analysis result (102), print unit (135) print analysis date, operator information (304) on an operator in charge of analysis, and subject attribute information (306) on the subject from which specimen (101) is collected. This configuration makes it possible to facilitate managing and dealing with printed sheet (300) because information necessary to manage analysis results (102) can be printed together with analysis results (102). Moreover, in the case of outputting information other than analysis results (102) in addition to analysis results (102), the amount of information increases. For this reason, there is increased possibility of overlooking because display unit (131) has to display the information in multiple screens. Hence, in the case of outputting other information such as analysis date (303) together with analysis results (102), it is particularly effective to print on print sheet (136) for the purpose of preventing overlooking of analysis results (102).

In this case, it is preferable that subject attribute information (306) include at least one of date of birth, age, and sex. The age of the subject can be calculated from the date of birth. The age and the sex of the subject are important information particularly useful for diagnosis based on analysis results (102), and thereby contributing to convenience for the user such as the ordering doctor when printed on printed sheet (300) together with analysis results 102.

In specimen analyzer (100) according to the first aspect described above, it is preferable that in addition to analysis result (102), print unit (135) print reference value information (309) to evaluate analysis result (102). Here, reference value information (309) is information on a reference value which is referred to when evaluating a value obtained as analysis result (102), and can include, for example, normal-value, high-value, or low-value information. This configuration makes it possible to improve convenience during diagnosis based on analysis results (102) because printed analysis results (102) and reference value information (309) can be compared on printed sheet (300). Moreover, in the case of outputting reference value information (309) in addition to analysis results (102), the amount of information increases. For this reason, there is increased possibility of overlooking because display unit (131) has to display the information in multiple screens. Hence, in the case of outputting reference value information (309) together with analysis results (102), it is particularly effective to print on print sheet (136) for the purpose of preventing overlooking of analysis results (102).

In this case, it is preferable that reference value information (309) be information on a numerical range indicating a normal range of analysis result (102). In such a configuration, on printed sheet (300), reference value information (309) makes it possible to grasp whether or not analysis results (102) are normal values. Hence, it is possible to improve convenience during diagnosis based on analysis results (102).

In the above-described configuration where reference value information (309) is printed in addition to analysis result (102), it is preferable that reference value information (309) is selectable from among two or more types of reference value information depending on subject attribute information (306) on the subject from which specimen (101) is collected, and print unit (135) print subject attribute information (306) and the types of reference value information (309) corresponding to subject attribute information (306) among the types of reference value information (309). This configuration makes it possible to provide a more appropriate reference value to the user depending on subject attribute information (306). As a result, it is possible to further improve convenience during diagnosis based on analysis results (102).

In this case, it is preferable that if analysis result (102) includes an abnormal value, controller (140) cause print unit (135) to print a predetermined message, and print unit (135) print analysis result (102), subject attribute information (306), reference value information (309), and the predetermined message on the same surface of a single piece of print sheet (136). Here, the predetermined message includes a message provided depending on the content of analysis result (102) such as a message notifying that an abnormal value which requires attention is obtained as analysis result (102), or a message prompting retest. This configuration makes it possible to print subject attribute information (306) and reference value information (309) useful for diagnosis, and when necessary, predetermined messages (311, 312), together with analysis result (102), and to collectively provide them to the ordering doctor or the like. Hence, it is possible to improve convenience during diagnosis based on analysis result (102). Moreover, it is possible to prevent overlooking of printed information by the user because printing is performed on one piece of print sheet (136) in one page even in the case of outputting subject attribute information (306), reference value information (309), and predetermined messages (311, 312) together with analysis result (102).

In the configuration where the predetermined message is printed if the above-described analysis result includes an abnormal value, it is preferable that the predetermined message include message (311) prompting further testing. In such a configuration, message (311) prompting further testing allows the user to propose to the patient that he/she have a detailed examination at, for example, a specialized medical facility, enabling appropriate diagnosis based on more appropriate analysis results. Moreover, it is possible to seek instructions of the ordering doctor or the like based on the message even if the operator of the apparatus does not understand the content of analysis results (102).

In this case, it is preferable that print unit (135) print the predetermined message subsequent to analysis result (102) on print sheet (136). This configuration makes it possible for the user such as the ordering doctor to recognize the predetermined message by continuously reading the print content after he/she checks analysis results (102) on printed sheet (300). Thus, it is possible to prevent overlooking of not only analysis results (102) but also the predetermined message.

In specimen analyzer (100) according to the first aspect described above, it is preferable that display unit (131) display print operation screen (P154) for starting of printing of analysis result (102), and print unit (135) start the printing of analysis result (102) based on an operation in accordance with print operation screen (P154). In such a configuration, when the user intentionally performs operation in accordance with print operation screen (P154), printing of analysis result (102) is started. This makes sure that the user recognizes printed sheet (300) of analysis result (102) by intentional operation, as opposed to the case where the user may forget to check printed sheet (300) at automatic start of printing when the analysis is completed. This also makes it possible to prevent overlooking of analysis result (102).

In this case, it is preferable that in print operation screen (P154), display unit (131) display operational guidance and an instruction on how to deal with printed sheet (300) after printing. The instructions to deal with printed sheet (300) include, for example, instructions to hand in printed sheet (300) to the operator of the apparatus. In such a configuration, prior to operation, print operation screen (P154) shows not only a description on the operation by the user in the case where print operation screen (P154) is displayed, but also instructions to deal with printed sheet (300) after operation and the printing is started. Since there is possibility that the user may not take a look at the display screen after he/she performs operation in accordance with print operation screen (P154), the above configuration makes sure that the user recognizes the instructions relating to printed sheet (300) before the printing is started. As a result, it is possible to more reliably communicate analysis results (102) to the ordering doctor or the like even if the user is unaccustomed to dealing with specimen analyzer (100).

In the above-described configuration of displaying, in print operation screen (P154), operational guidance and an instruction on how to deal with printed sheet (300) after printing, it is preferable that the instruction on how to deal with printed sheet (300) include a message instructing to deliver printed sheet (300) to an ordering doctor. In such a configuration, prior to outputting printed sheet (300), a message is displayed instructing to deliver printed sheet (300) to the ordering doctor. Thus, it is possible to more reliably communicate analysis results (102) to the ordering doctor or the like even if the user is unaccustomed to dealing with specimen analyzer (100).

In specimen analyzer (100) according to the first aspect described above, it is preferable that controller (140) perform control of disabling analysis unit (120) from analyzing next specimen (101) until print unit (135) completes printing of analysis result (102). In such a configuration, when analysis is performed on certain specimen (101), the analysis operation for next specimen (101) is not started unless analysis results (102) are printed. Thus, since analysis results (102) are reliably printed each time an analysis is performed, it is possible not only to prevent overlooking of analysis results (102), but also to prevent wrong taking of analysis results (102) in the case of performing analysis more than one time.

In specimen analyzer (100) according to the first aspect described above, it is preferable that if analysis result (102) includes an abnormal value, controller (140) cause display unit (131) to display abnormal value notification screen (P156) to report that the abnormal value is included, and analysis unit (120) be capable of retesting same specimen (101) if an operation in accordance with abnormal value notification screen (P156) is performed. In such a configuration, it is possible for the user to retest same specimen (101) as a recommended action if there is an abnormal value which requires attention during diagnosis based on analysis results (102). Since retest is not started unless operations are performed in accordance with abnormal value notification screen (P156), it is possible for the user, unaccustomed to dealing with specimen analyzer (100), to more reliably recognize the necessity of retest.

In this case, it is preferable that if analysis result (102) includes an abnormal value, controller (140) prohibit print unit (135) from printing analysis result (102), and cause abnormal value notification screen (P156) to show a message prompting to perform retesting. In such a configuration, the fact that analysis results (102) are not printed and the message prompting to perform retest make it possible for the user, unaccustomed to dealing with specimen analyzer (100), to strongly recognize the necessity of retest. In addition, since analysis results (102) including an abnormal value are not printed, it is possible to prevent wrong treatment based on the abnormal value.

In the configuration which can retest same specimen (101) if an operation is performed in accordance with above-described abnormal value notification screen (P156), it is preferable that if initial analysis result (102) matches retested analysis result (102), controller (140) cause print unit (135) to print analysis result (102), and if initial analysis result (102) does not match retested analysis result (102), controller (140) prohibits print unit (135) from printing mismatched analysis result (102). This configuration makes it possible to provide analysis results (102) to the user and to cause the user to perform necessary action because analysis results (102) with an abnormal value is correct if initial analysis results (102) match retested analysis results (102). On the other hand, if initial analysis results (102) do not match retested analysis results (102), there is possibility that correct analysis results (102) cannot be obtained for a reason. Hence, it is possible to keep analysis results (102) from being provided to the user. As a result, it is possible to avoid inappropriate treatment performed based on low-reliability analysis results.

In specimen analyzer (100) according to the first aspect described above, it is preferable that if analysis result (102) includes an abnormal value, controller (140) cause print unit (135) to print information (102*b*) indicating a type of an abnormality as analysis result (102). In such a configuration, if analysis results (102) of certain specimen (101) include an abnormal value, it is possible for the operator or the ordering doctor to know there is an abnormal value using printed sheet (300) on which information (102*b*) indicating the type of the abnormality is printed. As a result, it is possible to further improve the convenience during diagnosis based on analysis results (102).

In this case, it is preferable that if a certain abnormal value included in analysis result (102) is within preset predetermined numerical range (360), controller (140) exclude the certain abnormal value in analysis result (102) from printing. In this configuration, if predetermined numerical range (360) is set to a numerical range of abnormal value which requires attention particularly in clinical examination, for example, it is possible to strongly prompt to perform e.g. retest when a predetermined abnormal value is obtained which requires attention in particular because the predetermined abnormal value is not provided to the ordering doctor or the like. Additionally, it is possible to avoid inappropriate treatment performed based on an abnormal value belonging to predetermined numerical range (360).

In this case, it is preferable that when excluding the certain abnormal value from printing, controller (140) cause substitute indication (313) to be printed in place of the certain abnormal value. In such a configuration, it is possible to remove a predetermined abnormal value from printing while causing the user to recognize that certain analysis results (102) are obtained by using substitute indication (313). Hence, the user does not misunderstand that the analysis has not been performed for a reason, unlike the case of simply removing a predetermined abnormal value.

In specimen analyzer (100) according to the first aspect described above, it is preferable that in a case where analysis result (102) includes an abnormal value, controller (140) cause print unit (135) to print information (102*b*) indicating a type of an abnormality as analysis result (102), and in a case where there is an error other than analysis result (102) in the analyzer, controller (140) cause display unit (131) to display information indicating that there is the error. This configuration causes the ordering doctor or the like to surely recognize an error relating to analysis results (102) by handing over printed sheet (300) from the operator to the ordering doctor or the like, because the error relating to analysis results (102) is printed by print unit (135). On the other hand, display unit (131) displays an apparatus error which is not necessarily notified to the ordering doctor or the like. Thus, information unnecessary for diagnosis does not have to be printed on printed sheet (300).

In this case, it is preferable that controller (140) cause information that there is an error in at least one of the analysis unit (120) and a quality control process of analysis unit (120) to be displayed. This makes it possible for the user to recognize an error relating to analysis operations or analysis quality displayed on display unit (131).

In specimen analyzer (100) according to the first aspect described above, it is preferable that specimen (101) be blood, and analysis unit (120) analyze the number of blood cells and a concentration of a component contained in blood. To be more specific, the specimen analyzer is a blood cell counting apparatus. Analysis result (102) can include analysis values such as the number of cell components such as various blood cells and platelets, a measurement value of e.g. a concentration of a component in blood, ratios of blood cells based on the measured values, an average volume, and a distribution width. The blood cell counting apparatus performs some of the blood tests widely used in clinical examination, and analysis results (102) are clinically important because they are related to various types of diseases. For this reason, the invention, which is capable of preventing overlooking of analysis results (102), is suitably applied to blood cell counting apparatuses. Also, analysis results (102) of the blood cell counting apparatus tend to be large in amount because they include multiple items. This increases the risk of overlooking due to the necessity of displaying them in multiple screens. Hence, printing on print sheet (136) is particularly effective in preventing overlooking of analysis results (102).

In specimen analyzer (100) according to the first aspect described above, it is preferable that controller (140) do not proceed to a next process until print sheet (136) is set in print unit (135). In such a configuration, an analysis operation for specimen (101) does not start unless print sheets (136) are set. Hence, it is possible to surely prevent a situation where analysis results (102) are not printed because the print unit is out of paper, and thus to prevent overlooking of analysis results (102).

A specimen analysis method according to a second aspect of the invention is a specimen analysis method in specimen analyzer (100) which includes print unit (20) and display unit (30). The method includes: analyzing specimen (101) collected from a subject; causing print unit (20) to print analysis result (102) on a print sheet; and prohibiting display unit (30) from displaying analysis result (102).

In the specimen analysis method according to the second aspect, as described above, print unit (20) prints analysis results (102) on the print sheet, and display unit (30) does not display analysis results (102). Thus, analysis results (102) are not displayed by display unit (30), but printed on print sheet (50) by print unit (20). Although the size of the display screen displayable at one time by display unit (30) is limited, the print area of print unit (20) can be adjusted as desired by, for example, changing the size of the print sheet. Thus, it is possible to print analysis results (102) without making the font size small. Additionally, also in the case of e.g. printing analysis results (102) on more than one print sheet (50), the user more easily recognizes the presence of more than one printed sheet by touching the printed sheets, unlike the case of switching screens. As a result, it is possible to prevent erroneous recognition of analysis results (102) attributed to low visibility and overlooking of analysis results (102) by the user, even in the case of a small display screen. Also, there is a case where the operator of the apparatus directly communicates analysis results (102) to the ordering doctor or the like. In that case, by printing analysis results (102), the user such as an operator can hand in printed sheet (300) to the ordering doctor or the like without any modifications. Thus, miscommunication of analysis results (102) to the ordering doctor can be prevented.

A specimen analyzer according to a third aspect of the invention includes: analysis unit (410) which analyzes specimen (101) collected from a subject; print unit (420) which prints on print sheet (450); display unit (430) which displays an operation screen; and controller (440) which performs control of causing print unit (420) to print analysis result (102) of analysis unit (410), and causing display unit (430) to display notification message (461) indicating that printed sheet (300), on which analysis result (102) has been printed, is to be outputted.

As described above, the specimen analyzer according to the third aspect includes controller (440) which performs control of causing print unit (420) to print analysis result (102) of analysis unit (410), and causing display unit (430) to display notification message (461) indicating that printed sheet (300), on which analysis result (102) has been printed, is to be outputted. Thus, analysis results (102) are printed on print sheet (450) by print unit (420). Although the size of the display screen displayable at one time by display unit (430) is limited, the print area of print unit (420) can be adjusted as desired by, for example, changing the size of the print sheet. Thus, it is possible to print analysis results (102) without making the font size small. Further, by message (461) displayed by display unit (430), the user is allowed to recognize that analysis results (102) are outputted as printed sheet (300). As a result, it is possible to prevent erroneous recognition of analysis results (102) attributed to low visibility and overlooking of analysis results (102) by the user, even in the case of a small display screen. Also, there is a case where the operator of the apparatus directly communicates analysis results (102) to the ordering doctor or the like. In that case, by printing analysis results (102), the user such as an operator can hand in printed sheet (300) to the ordering doctor or the like without any modifications. Thus, miscommunication of analysis results (102) to the ordering doctor can be prevented.

A specimen analysis method according to a fourth aspect of the invention is a specimen analysis method in specimen analyzer (100) which includes print unit (420) and display unit (430). The method includes: analyzing specimen (101) collected from a subject; causing print unit (420) to print analysis result (102) on print sheet (450); and causing display unit (430) to display notification message (461) indicating that printed sheet (300), on which analysis result (102) has been printed, is to be outputted.

In the specimen analysis method according to the fourth aspect, as described above, print unit (420) prints analysis results (102) on print sheet (450), and display unit (430) displays notification message (461) indicating that printed sheet (300), on which analysis results (102) has been printed, is to be outputted. Thus, analysis results (102) are printed on print sheet (450) by print unit (420). Although the size of the display screen displayable at one time by display unit (430) is limited, the print area of print unit (420) can be adjusted as desired by, for example, changing the size of the print sheet. Thus, it is possible to print analysis results (102) without making the font size small. Further, by message (461) displayed by display unit (430), the user is allowed to recognize that analysis results (102) are outputted as printed sheet (300). As a result, it is possible to prevent erroneous recognition of analysis results (102) attributed to low visibility and overlooking of analysis results (102) by the user, even in the case of a small display screen. Also, there is a case where the operator of the apparatus directly communicates analysis results (102) to the ordering doctor or the like. In that case, by printing analysis results (102), the user such as an operator can hand in printed sheet (300) to the ordering doctor or the like without any modifications. Thus, miscommunication of analysis results (102) to the ordering doctor can be prevented.

A specimen analyzer according to a fifth aspect of the invention includes: analysis unit (120) which analyzes specimen (101) collected from a subject; print unit (135) which prints on print sheet (136); display unit (131) which displays an operation screen; and controller (140) which causes display unit (131) to automatically display print operation screen (P154) for starting of printing of analysis result (102) when analysis unit (120) finishes analyzing specimen (101), and causes print unit (135) to start the printing of analysis result (102) in response to an operation in accordance with print operation screen (P154).

As described above, the specimen analyzer according to the fifth aspect includes controller (140) which causes display unit (131) to automatically display print operation screen (P154) for starting of printing of analysis result (102) when analysis unit (120) finishes analyzing specimen (101), and causes print unit (135) to start the printing of analysis result (102) depending on an operation in accordance with print operation screen (P154). Thus, analysis results (102) are printed on print sheet (136) by print unit (135). Although the size of the display screen displayable at one time by display unit (131) is limited, the print area of print unit (135) can be adjusted as desired by, for example, changing the size of the print sheet. Thus, it is possible to print analysis results (102) without making the font size small. When print unit (135) starts the printing of analysis results (102) depending on the operations in accordance with print operation screen (P154), the user is allowed to recognize that analysis results (102) are outputted as printed sheet (300). As a result, it is possible to prevent erroneous recognition of analysis results (102) attributed to low visibility and overlooking of analysis results (102) by the user, even in the case of a small display screen. Also, there is a case where the operator of the apparatus directly communicates analysis results (102) to the ordering doctor or the like. In that case, by printing analysis results (102), the user such as an operator can hand in printed sheet (300) to the ordering doctor or the like without any modifications. Thus, miscommunication of analysis results (102) to the ordering doctor can be prevented.

BRIEF DESCRIPTION OF DRAWINGS

FIG. 49 is a diagram illustrating an example of print content of printed sheet;

FIG. 50 is a diagram for explaining a result displaying section of the printed sheet;

FIG. 51 is a diagram for explaining rules of outputting analysis results on the printed sheet;

FIG. 52 is a diagram for explaining first determination ranges;

FIG. 55 is a diagram for explaining numerical ranges for evaluating analysis results for an adult;

FIG. 56 is a diagram for explaining a first modification of a printing embodiment of the analysis results;

FIG. 57 is a diagram for explaining a second modification of the printing embodiment of the analysis results;

FIG. 58 is a diagram for explaining first and second modifications of the rules of outputting the analysis results;

DETAILED DESCRIPTION OF PREFERRED EMBODIMENTS

First Embodiment

Hereinafter, embodiments are described based on the drawings.

[Overview of Specimen Analyzer and Specimen Analysis Method]

Figure 1:
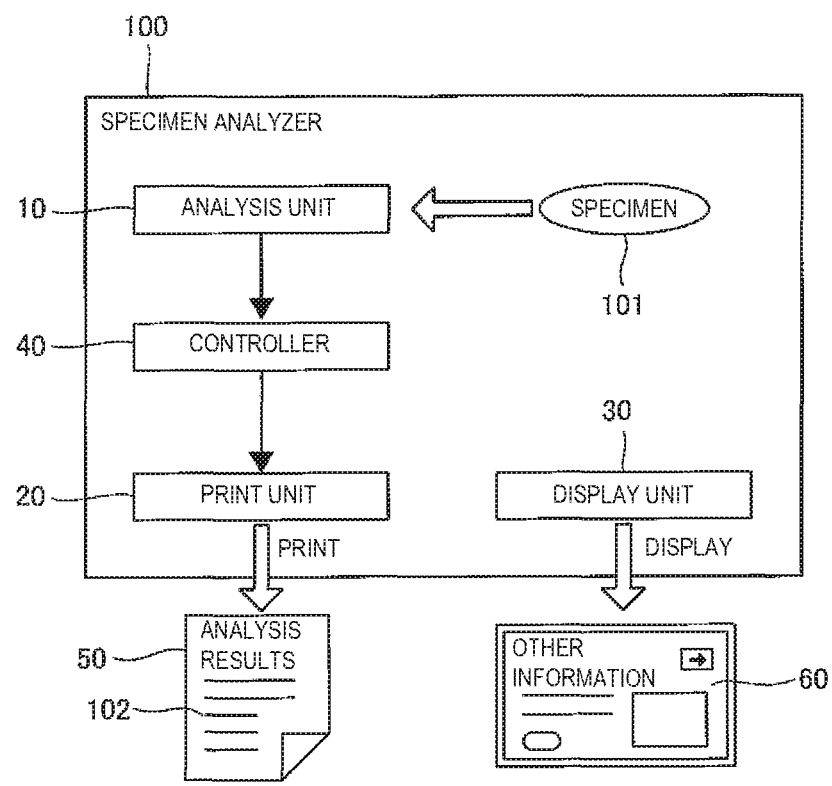
FIG. 1 is a diagram for explaining an overview of a specimen analyzer and a specimen analysis method according to a first embodiment.

With reference to FIG. 1, an overview of specimen analyzer 100 and a specimen analysis method according to a first embodiment is described.

Specimen analyzer 100 according to the first embodiment is an apparatus for analyzing a specimen collected from a subject.

The subject is a human in most cases, but may be an animal other than a human. Specimen analyzer 100 performs measurement or analysis for clinical examination of the specimen collected from, for example, a patient. Thus, the specimen is a specimen of biological origin. A specimen of biological origin is, for example, a liquid such as blood (whole blood, serum, or plasma), urine, or other body fluids collected from the subject, or a liquid obtained by performing predetermined pre-treatment on a collected body fluid or blood. In addition, the specimen may be, for example, part of the tissue or a cell of the subject, rather than liquid. The specimen contains, for example, a target component designated as a test item for clinical examination. The target component may contain, for example, a predetermined component, cells, or particles in the blood or the urine specimen. The target component may be, for example, a nucleic acid such as DNA (deoxyribonucleic acid), a cell, an intracellular substance, an antigen, an antibody, a protein, or a peptide. Specimen analyzer 100 may be, for example, a blood cell counting apparatus, a blood coagulation analyzer, an immunoassay apparatus, and a urine particle analyzer, or an analyzer different from these.

For example, specimen analyzer 100 sets a container which contains specimen 101, performs predetermined operations, and thereby measures the target components depending on the analysis items in specimen 101. As a result, the specimen analyzer outputs analysis results 102. Analysis results 102 may be primary measurement results or detection results obtained by measuring the target components, or may be secondary analysis results obtained analytically on the basis of the measurement results. Analysis results 102 have, for example, numerical information. In addition to numerical information, analysis results 102 may have, for example, diagrams such as a scattergram and a histogram, other statistical quantities, and qualitative determination results (e.g. − and +).

As illustrated in FIG. 1, specimen analyzer 100 includes analysis unit 10, print unit 20 for printing on a print sheet, display unit 30 for displaying an operation screen, and a controller 40.

Analysis unit 10 is configured to analyze specimen 101 collected from a sample. For example, analysis unit 10 includes one or more detectors depending on the analysis items, and measures or detects the target components in specimen 101. Also, analysis unit 10 includes a computer having a processor and memories, and analyzes measurement results or detection results to generate analysis results. The number of analysis items may be one or more. Analysis unit 10 outputs analysis results 102 having the generated measurement results and/or analysis results to controller 40.

Print unit 20 is configured to print information on a predetermined medium such as print sheet 50. In the first embodiment, print unit 20 is configured to output analysis results 102 of analysis unit 10 by printing. As described later, print unit 20 prints analysis results 102, but does not print information and the like on an apparatus irrelevant to analysis results 102. A user such as an operator of the apparatus acquires analysis results 102 printed by print unit 20. The way of printing of print unit 20 does not matter as long as it is possible to print on a predetermined medium such as a print sheet. Print unit 20 may be a printing apparatus such as a thermal printer, inkjet printer, or a laser printer.

Display unit 30 is configured to display information such as an operation screen on display screen 60. Display unit 30 is, for example, a built-in display apparatus fastened to an apparatus body of specimen analyzer 100. Display unit 30 may be, for example, a liquid crystal or organic electroluminescent monitor, or electronic paper. In the first embodiment, display unit 30 is configured to perform output processing by displaying information other than analysis results 102 of analysis unit 10. Display unit 30 displays information other than analysis results 102, but does not display analysis results 102 or information associated with analysis results 102.

Controller 40 may be, for example, a computer including a processor such as a CPU, and memories which have programs recorded therein. Controller 40 of the first embodiment is capable performing control such that information to be outputted to the user is outputted through printing by print unit 20, or alternatively the information to be outputted to the user is outputted through display by display unit 30.

To be more specific, controller 40 performs control of causing print unit 20 to print analysis results 102 of analysis unit 10, and prohibiting display unit 30 from displaying analysis results 102.

In other words, controller 40 causes print unit 20 to print analysis results 102 obtained by analysis unit 10 having analyzed specimen 101. If the analysis results have abnormal values other than normal values, analysis results 102 can have information indicating the type of the abnormality. Information printed by print unit 20 includes information associated with analysis results 102, as well as analysis results 102. Information associated with analysis results 102 can include, for example, information on the facility where specimen analyzer 100 is installed, information for identifying the specimen analyzer which has performed analysis, information on the date when the analysis has been performed, information on the operator who has performed operation, information for identifying the subject from which specimen 101 is collected, attribute information on the subject showing the characteristics and nature of the subject, a message to be notified to the user depending on the analysis results, and information on a reference value for evaluating analysis results 102.

Controller 40 prohibits display unit 30 from displaying information on analysis results 102 outputted by print unit 20. Controller 40 causes display unit 30 to display information other than analysis results 102. Information other than analysis results 102 can include, for example, information on operating situation or status of the apparatus, information on operational guidance and information used by the user when operating specimen analyzer 100, and error information on specimen analyzer 100. As a result, the user grasps analysis results 102 only with use of the printed sheet printed by print unit 20. On the other hand, the user can grasp various types of information necessary when using the apparatus from display screen 60 of display unit 30.

As described above, in specimen analyzer 100 of the first embodiment, analysis results 102 are not displayed by display unit 30 but printed on print sheet 50 by print unit 20. Here, although the size of display screen 60 displayable at one time by display unit 30 is limited, the print area of print unit 20 can be adjusted as desired by, for example, changing the size of print sheet 50. Thus, it is possible to print analysis results 102 without making the font size small. Additionally, also in the case of e.g. printing analysis results 102 on more than one print sheet 50, the user more easily recognizes the presence of more than one printed sheet by touching the printed sheets, unlike the case of switching screens. As a result, it is possible to prevent erroneous recognition of analysis results 102 attributed to low visibility and overlooking of analysis results 102 by the user, even in the case of small display screen 60.

There is a case where the operator of the apparatus directly communicates analysis results 102 to the ordering doctor or the like. In that case, by printing analysis results 102, the user such as an operator can hand in printed sheet 300 to the ordering doctor or the like without any modifications. Thus, miscommunication of analysis results 102 to the ordering doctor can be prevented.

Additionally, in the first embodiment, specimen analyzer 100 performs the following specimen analysis method. To be more specific, specimen analyzer 100 analyzes specimen 101 collected from the subject. Specimen analyzer 100 causes print unit 20 to print analysis results 102 on the print sheet. Specimen analyzer 100 does not cause display unit 30 to display analysis results 102.

According to this specimen analysis method, analysis results 102 are not displayed by display unit 30, but printed on print sheet 50 by print unit 20. Although the size of display screen 60 displayable at one time by display unit 30 is limited, the print area of print unit 20 can be adjusted as desired by, for example, changing the size of print sheet 50. Thus, it is possible to print analysis results 102 without making the font size small. Additionally, also in the case of e.g. printing analysis results 102 on more than one print sheet 50, the user more easily recognizes the presence of more than one printed sheet by touching the printed sheets, unlike the case of switching screens. As a result, it is possible to prevent erroneous recognition of analysis results 102 attributed to low visibility and overlooking of analysis results 102 by the user, even in the case of small display screen 60. Moreover, by printing analysis results 102, the user such as an operator can hand in printed sheet 300 to the ordering doctor or the like without any modifications. Thus, miscommunication of analysis results 102 to the ordering doctor can be prevented.

[Configuration Example of Specimen Analyzer]

Figure 2:
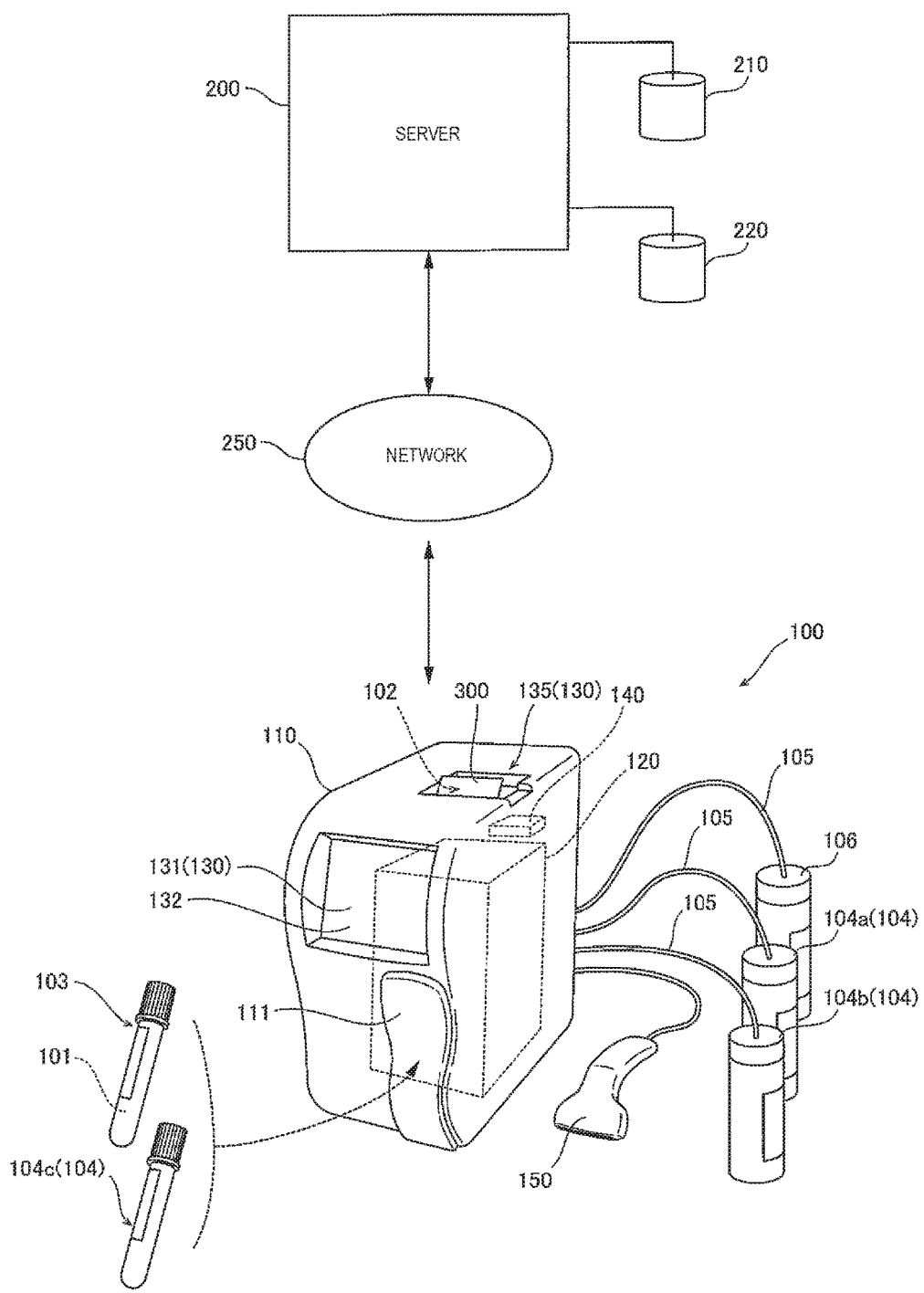
FIG. 2 is a perspective view illustrating a configuration example of the specimen analyzer.

With reference to FIG. 2 to FIG. 57, a configuration example of specimen analyzer 100 is described.

(Overall Configuration)

In the example illustrated in FIG. 2, specimen 101 is blood in specimen analyzer 100, and specimen analyzer 100 is a blood cell counting apparatus. The blood cell counting apparatus is an apparatus which counts the number of blood cells contained in a predetermined volume of blood specimen. Analysis unit 120 analyzes the number of blood cells and concentrations of the components contained in the blood. The blood cell counting apparatus performs some of the blood tests widely used in clinical examination, and analysis results 102 are clinically important because they are related to various types of diseases. For this reason, specimen analyzer 100 of the first embodiment, which is capable of preventing overlooking of analysis results 102, is suitably applied to blood cell counting apparatuses. Also, analysis results 102 of the blood cell counting apparatus tend to be large in amount because they include multiple items. This increases the risk of overlooking due to the necessity of displaying them in multiple screens. Hence, printing on the print sheet is particularly effective in preventing overlooking of analysis results 102.

When specimen container 103 containing specimen 101 is set, specimen analyzer 100 aspirates specimen 101 in specimen container 103 and analyzes the specimen. For example, a container in the shape of a generally-used blood collection tube can be used as specimen container 103. Specimen container 103 is, for example, a vacuum blood collection tube capped with a rubber cap or an open blood collection tube which has an opening. Specimen 101 to be contained in specimen container 103 is, for example, whole blood of a subject (human), and is added with an anticoagulant. The necessary amount of added anticoagulant is, for example, 10 μL to 15 μL inclusive.

Specimen analyzer 100 has apparatus body 110 which includes analysis unit 120 for analyzing the specimen collected from the subject, output unit 130 for outputting analysis results 102 of analysis unit 120, and controller 140. Moreover, specimen analyzer 100 includes information read unit 150 connected to apparatus body 110. Further, specimen analyzer 100 is connected to various types of consumables 104 used along with analysis operation for specimen 101.

Apparatus body 110 is a unit provided with analysis unit 120, output unit 130, etc. in a box-shaped housing. Apparatus body 110 is configured as a small blood cell counting apparatus which can be a desktop one, including information read unit 150 and consumables 104. Analysis unit 120 and controller 140 are built in apparatus body 110.

Container set unit 111 is provided at a front and lower portion of apparatus body 110. Container set unit 111 is configured such that it is openable and closable from the front surface of apparatus body 110 in the direction toward the user (see FIG. 3). Using container set unit 111, specimen container 103 containing specimen 101 is set in apparatus body 110.

In the example illustrated in FIG. 2, analysis unit 120 is configured to analyze multiple analysis items. As an example, as measurement items by analysis unit 120, the analysis items include e.g. eight items: white blood cell count (WBC), red blood cell count (RBC), hemoglobin concentration (HGB), hematocrit value (HCT), mean corpuscular volume (MCV), mean corpuscular hemoglobin (MCH), mean corpuscular hemoglobin concentration (MCHC), and platelet count (PLT). As analysis items to be analyzed on the basis of the analysis results of the measurement items, the analysis items include e.g. nine items: WBC-small cell ratio (% Lymph), WBC-middle cell ratio (% OtherWBC), WBC-large cell ratio (% Neut), WBC-small cell count (#Lymph), WBC-middle cell count (#OtherWBC), WBC-large cell ratio (#Neut), red blood cell distribution width (RDW-SD and RDW-CV), mean platelet volume (MPV). In this example, the number of analysis items of analysis unit 120 is 17.

Output unit 130 outputs various types of information on specimen analyzer 100 to the user. In the example of FIG. 2, output unit 130 includes display unit 131 and print unit 135. In the example of FIG. 2, display unit 131 is an LCD (liquid crystal display), and is disposed at a front and upper portion of apparatus body 110. In the example of FIG. 2, print unit 135 is a thermal printer which prints on thermal paper with use of heat, and is located on an upper surface of apparatus body 110.

Moreover, specimen analyzer 100 includes manual input unit 132 which receives an input operation of the user. In the example of FIG. 2, manual input unit 132 is a touch panel provided on display unit 131. The user is allowed to input information and perform various operations by touching the icons displayed on display unit 131.

In the example of FIG. 2, information read unit 150 is configured to read an identifier provided on each of consumables 104, and to receive inputted information. To be more specific, information read unit 150 is a read apparatus such as a barcode reader, a two-dimensional code reader, and a camera. The identifier is a barcode or a two-dimensional code.

In the example of FIG. 2, inputting of information on consumables 104 by manual input unit 132 is not permitted, but inputting by information read unit 150 is permitted. Controller 140 determines whether to use consumables 104 based on information on consumables 104 inputted by information read unit 150. To be more specific, controller 140 allows use of consumables 104 if information on consumables 104 inputted by information read unit 150 is registered on server 200.

Consumables 104 are consumed along with analysis operation of specimen 101 by specimen analyzer 100. Consumables 104 contain the reagent used for the analysis of specimen 101. In the example of FIG. 2, used as consumables 104 are diluted solution container 104*a* containing a diluted solution for diluting specimen 101 and hemolyzer container 104*b* containing a hemolyzer which hemolyzes blood cells. Moreover, consumables 104 contain a cleaning agent for cleaning specimen analyzer 100. In the example of FIG. 2, used as consumable 104 is cleaning agent container 104*c* containing a cleaning agent for cleaning a fluid circuit in the apparatus. Note that the diluted solution is used for a cleaning process. The cleaning agent contains a cleaning component such as a sodium hypochlorite solution, and has more cleaning power than the diluted solution. Cleaning with use of the cleaning agent is regularly carried out each time a predetermined period elapses, e.g. one week. Cleaning with use of the diluted solution is carried out more frequently than the cleaning with use of the cleaning agent each time the analysis of specimen 101 is performed, for example. The identifiers provided on consumables 104 have information on consumables 104 recorded therein. Information on consumables 104 includes at least one of the type of consumable 104, expiration date, lot number, and serial number.

As an example, in the example of FIG. 2, "pocH-pack D (manufactured by Sysmex Corporation, registered trademark)" is preferably used as the diluted solution, "pocH-pack L (manufactured by Sysmex Corporation, registered trademark)" is preferably used as the hemolyzer, and "CELLCLEAN (manufactured by Sysmex Corporation, registered trademark)" is preferably used as the cleaning agent.

(Configuration of Each of Units of Specimen Analyzer)

Figure 3:
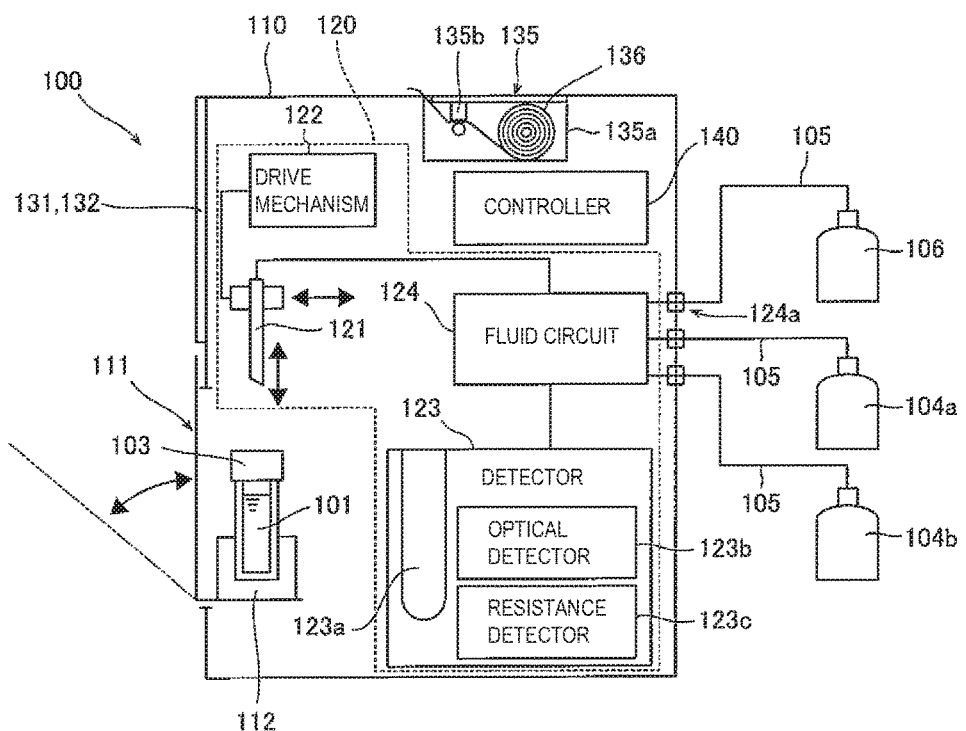
FIG. 3 is a schematic view illustrating an internal configuration example of the specimen analyzer.

In the example illustrated in FIG. 3, print unit 135 is configured such that it can change the size of print sheet 136, and is configured to print analysis results 102 on the same surface of a single piece of print sheet 136. To be more specific, analysis results 102 are printed on one piece of print sheet 136 in one page. For this reason, it is possible to prevent a situation where e.g. the user overlooks the print content on the back side in the case of double-side printing and where the user finds it hard to recognize the content of analysis results 102 in the case of printing on multiple print sheets 136, and thus to easily and surely recognize all of analysis results 102 at one sight. Furthermore, in a case of printing on one piece of print sheet 136 in one page, it is possible to print analysis results 102 on appropriate-sized print sheet 136 even in a case where the print amount is large or small, depending on the content of analysis results 102.

To be more specific, print unit 135 includes sheet set unit 135*a* which holds print sheet 136 which is elongated, and changes the size of print sheet 136 by printing on an area of print sheet 136 with an appropriate length depending on the print amount. This makes it possible to print analysis results 102 in any print amount by merely adjusting the length of the print area on the same print sheet 136. This therefore eliminates the necessity of preparing several types of print sheets 136 with different sheet sizes, thereby simplifying the apparatus configuration.

In the example of FIG. 3, set to sheet set unit 135*a* is print sheet 136 which is roll paper being rolled thermal paper which is elongated with a predetermined width. In addition, print unit 135 includes print head 135*b* which heats print sheet 136, and prints using print head 135*b* while forwarding rolled print sheet 136 with a not-illustrated motor. Thus, print unit 135 prints on an area of print sheet 136 with an appropriate length depending on the amount of information to be printed including analysis results 102. The user cuts the printed sheet sent from print unit 135 in an appropriate length, and acquires one sheet of printed sheet on which analysis results 102 are printed.

Container set unit 111 includes adapter 112 for holding a lower portion of specimen container 103. When open, container set unit 111 is capable of holding specimen container 103 in an upright state. Here, in addition to specimen container 103, it is possible to set, to container set unit 111, a QC reagent container (not illustrated) which contains a control specimen (hereinafter referred to as QC reagent) for quality control and cleaning agent container 104c.

Analysis unit 120 includes pipette 121 for aspirating specimen 101 from specimen container 103 set to container set unit 111 and drive mechanism 122 for pipette 121. Moreover, analysis unit 120 includes detector 123 for detecting components in specimen 101 and fluid circuit 124 for feeding liquid. Furthermore, analysis unit 120 (see FIG. 4) includes a computer which has processor 141 and memory 142.

Pipette 121 is an aspiration tube for measuring the amount of a liquid. Drive mechanism 122 includes linear mechanisms made up of e.g. a guiderail, a motor, and a belt pulley mechanism, and holds pipette 121. Pipette 121 is provided at a position above specimen container 103 set in container set unit 111, and is configured such that it can move in the up-down direction and in the horizontal direction. Pipette 121 is connected to a syringe pump provided in fluid circuit 124, and is capable of aspirating a predetermined amount of specimen 101 contained in specimen container 103. Pipette 121 is moved down from a position above specimen container 103, enters the inside of specimen container 103, and is allowed to aspirate a predetermined amount of specimen 101 by fluid circuit 124. Moreover, pipette 121 is moved by drive mechanism 122 to a position above a mixing chamber of fluid circuit 124 to be described later and to a position above container unit 123a of detector 123, and is allowed to aspirate and discharge liquid by fluid circuit 124 at each of the positions. In the case where the QC reagent container containing the QC reagent and the cleaning agent container are set in container set unit 111, pipette 121 can also aspirate the QC reagent and the cleaning agent by performing the same or similar operations.

Fluid circuit 124 includes e.g. a mixing chamber, a pressure source, a syringe pump, a diluted solution, chambers for hemolyzer and waste liquid, a cleaning Spitz for cleaning pipette 121, various valves for switching liquid feed, and a sensor. Fluid circuit 124 connects pipette 121 and detector 123 together in a fluid manner via a flow path such as a liquid feed tube. Moreover, fluid circuit 124 is connected in a fluid manner to external connectors 124a provided on the back surface of apparatus body 110. The number of external connectors 124a provided is three, which are separately connected via connection tubes 105 to diluted solution container 104a, hemolyzer container 104b, and waste liquid container 106.

Fluid circuit 124 mixes a predetermined amount of specimen 101 aspirated by pipette 121 and a predetermined amount of diluted solution in a mixing chamber to prepare an RBC/PLT measurement specimen, which is a diluted specimen with a predetermined ratio. In addition, fluid circuit 124 mixes a predetermined amount of specimen 101, a predetermined amount of diluted solution, and a predetermined amount of hemolyzer to prepare a WBC/HGB measurement specimen which includes a mixed solution of blood specimen, diluted solution, and hemolyzer.

Detector 123 is configured to measure the target components in specimen 101 corresponding to the analysis items. In the example of FIG. 3, detector 123 measures multiple items. In the example of FIG. 3, detector 123 is configured to perform measurement in accordance with multiple measurement principles depending on the target components of the analysis items.

To be more specific, detector 123 performs RBC measurement and PLT measurement using a sheath flow electrical resistance method. Detector 123 performs WBC measurement using an electrical resistance method. Detector 123 includes resistance detector 123b for performing measurement using the sheath flow electrical resistance method and the electrical resistance method. Moreover, detector 123 performs HGB measurement using a colorimetric method. Detector 123 includes optical detector 123c for performing measurement using the colorimetric method.

The sheath flow electrical resistance method forms a sheath flow of a specimen flow and a flow of sheath liquid surrounding the specimen flow, and causes the sheath flow to pass through an orifice. Electrodes are provided in front and rear of the orifice, respectively, in the flow direction. A pulse signal, which represents the presence and volume information of each blood cell, is measured based on the change in resistance between the electrodes generated by the blood cells passing through the orifice.

Here, the diluted solution forms the flow of sheath liquid, and the RBC/PLT measurement specimen forms the specimen flow. Resistance detector 123b includes an orifice and a pair of electrodes used for measurement. Analysis unit 120 obtains the red blood cell count (RBC), the platelet count (PLT), and the hematocrit value (HCT) from the measured count value of the pulse signal.

The electrical resistance method causes the WBC/HGB measurement specimen to pass through an orifice, and measures a pulse signal which represents the presence and volume information of each blood cell based on the change in resistance between the front and rear electrodes of the orifice. Analysis unit 120 obtains the white blood cell count (WBC) from the measured count value of the pulse signal.

The colorimetric method causes a light source to emit measurement light to the WBC/HGB measurement specimen, and detects the measurement light having passed through the specimen with a light receiving element. Additionally, the same process is also performed on the diluted solution as a blank, and analysis unit 120 obtains the hemoglobin concentration (HGB) based on the difference in absorbance between the diluted solution and the WBC/HGB measurement specimen. Optical detector 123c includes the light source and the light receiving element used for measurement. The light source is, for example, an LED, and the light receiving element is, for example, a photodiode.

The mean corpuscular volume (MCV), the mean corpuscular hemoglobin (MCH), and the mean corpuscular hemoglobin concentration (MCHC) are calculated by analysis unit 120 from the measurement values of the red blood cell count (RBC), the platelet count (PLT), and the hematocrit value (HCT), respectively.

Based on the analysis results of the measurement items, analysis unit 120 obtains the analysis items of the WBC-small cell ratio (% Lymph), the WBC-middle cell ratio (% OtherWBC), the WBC-large cell ratio (% Neut), the WBC-small cell count (#Lymph), the WBC-middle cell count (#OtherWBC), the WBC-large cell ratio (#Neut), the red blood cell distribution width (RDW-SD and RDW-CV), the mean platelet volume (MPV).

Figure 4:
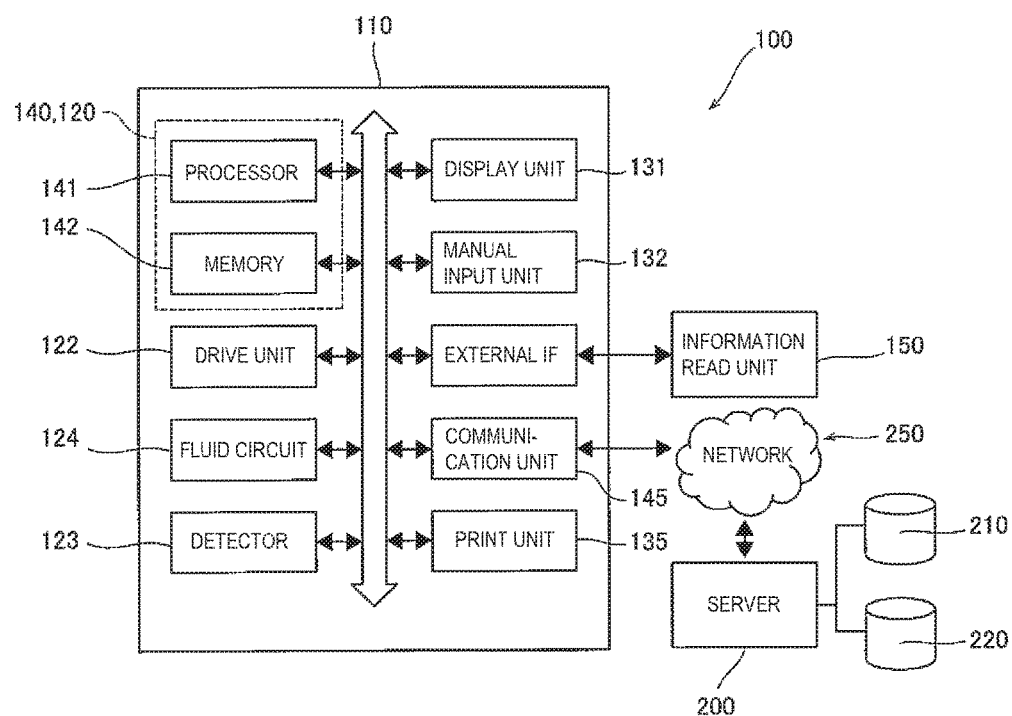
FIG. 4 is a block diagram illustrating a configuration of the specimen analyzer.

As illustrated in FIG. 4, controller 140 includes processor 141 such as a CPU and memory 142. Memory 142 can include a volatile memory such as a RAM, and a non-volatile memory such as a ROM, a flash memory, and a hard disk. Memory 142 has, for example, a control program for controlling specimen analyzer 100, analysis program for obtaining analysis results 102, and display screen data of display unit 131 recorded therein. Processor 141 executes a program recorded in memory 142 and thereby functions as controller 140 which performs operation control of units such as drive mechanism 122, fluid circuit 124, detector 123, display unit 131, and print unit 135. Moreover, processor 141 functions as part of analysis unit 120 which obtains analysis results 102 of the analysis items by executing the programs recorded in memory 142. Controller 140 and analysis unit 120 may be configured as a separate processor and memory. Furthermore, controller 140 obtains information inputted through manual input unit 132 and processes that information. What is more, controller 140 controls read operation by information read unit 150 through an external IF, and processes the read information. Still further, controller 140 is capable of connecting to network 250 via communication unit 145, and thus accessing management server 200 of specimen analyzer 100. Communication unit 145 includes a communication interface, and establishes cabled or wireless connection to network 250. Communication unit 145 connects to network 250 via, for example, an Ethernet cable.

(Description on Server)

Registered with storage unit 210 of server 200 are serial numbers of individual specimen analyzers 100. To be more specific, the user is allowed to use only specimen analyzers 100 registered with server 200. Registered with storage unit 220 of server 200 are lot numbers and serial numbers of reagents. To be more specific, the user is allowed to use only the reagents registered with server 200 in specimen analyzer 100. Moreover, stored in storage unit 220 of server 200 is information on a QC reagent being a control specimen for quality control. Information on a QC reagent is stored associated with the lot number of that QC reagent. To be more specific, information on a QC reagent includes information on a measurement range of the QC reagent. For example, QC reagents used include a High QC reagent containing a highly concentrated component, a Normal QC reagent containing a normally concentrated component, and a Low QC reagent containing a low concentrated component. A normal value of the measurement result is set for each QC reagent depending on High, Normal, and Low. Moreover, the QC reagent has a varying normal value depending on the lot. In light of this, storage unit 220 of server 200 stores ranges of normal values in the case of measuring QC reagents depending on the types High, Normal, and Low, and the lot number.

[Operation Example of Specimen Analyzer]

Figure 5:
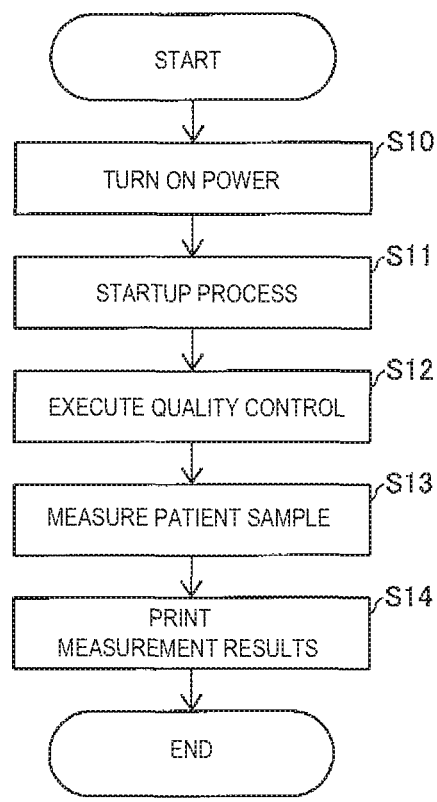
FIG. 5 is a flowchart illustrating an example of operations of the specimen analyzer.

With reference to FIG. 5, an operation example of specimen analyzer 100 is described.

When the power is turned ON at step S10, a startup process is performed at step S11. To be more specific, the system is automatically checked. Also, the inside of the apparatus is automatically cleaned. Additionally, blank check is performed.

At step S12, quality control is executed. The quality control is performed at predetermined intervals. Display unit 131 displays a screen requiring quality control at predetermined intervals. The user inputs data concerning quality control in accordance with what is being displayed, and instructs to measure quality control substances.

At step S13, a patient sample as a specimen is measured. Display unit 131 displays a screen of an instruction for sample measurement. The user performs sample measurement instruction in accordance with what is being displayed. At step S14, the measurement results are printed. To be more specific, the measured and analyzed results are printed and outputted from print unit 135. Note that display unit 131 does not display the measurement results.

[Description on Sample Measurement Process]

Figure 6:
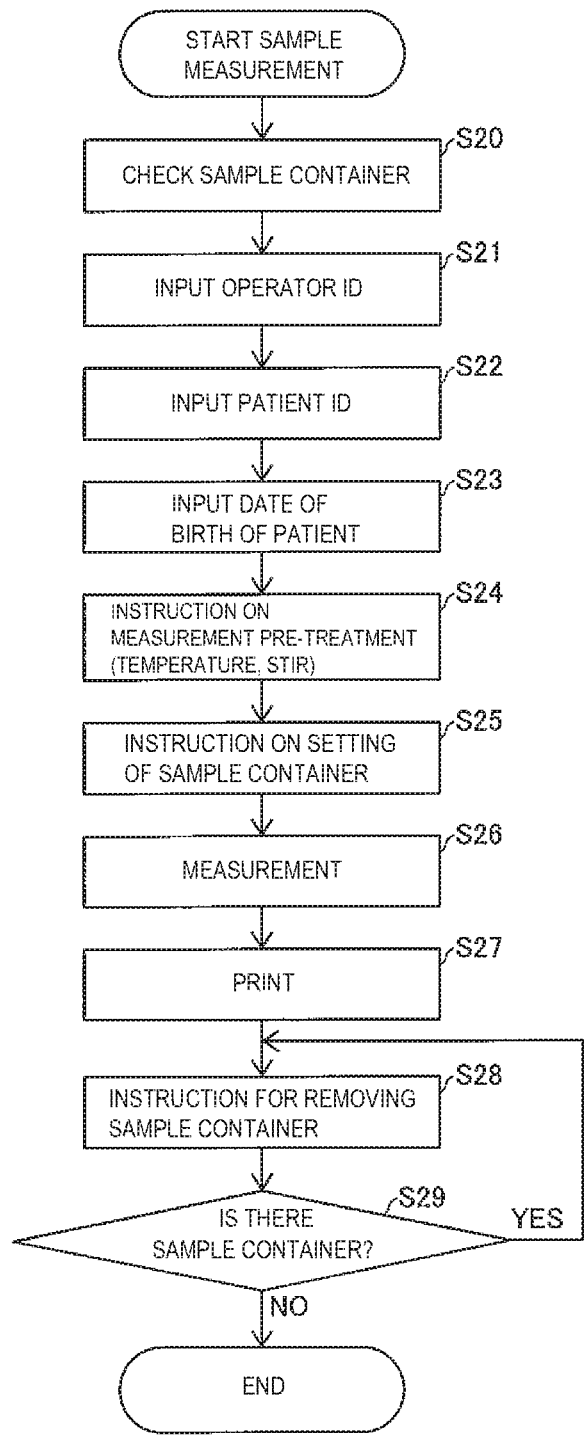
FIG. 6 is a flowchart illustrating an example of a sample measurement process.

With reference to FIG. 6, an example of a sample measurement process by specimen analyzer 100 is described. In the example illustrated in FIG. 6, specimen analyzer 100 measures and analyzes the sample of a patient as a specimen.

At step S20, a sample container is checked. To be more specific, display unit 131 displays images of the types of sample containers available. The user checks the sample container by comparing the images and the actual sample container. At step S21, an operator ID is inputted. To be more specific, the user inputs an ID for identifying the operator in accordance with the instructions of display unit 131.

At step S22, a patient ID is inputted. To be more specific, the user inputs an ID for identifying the patient in accordance with the instructions of display unit 131. At step S23, the date of birth of the patient is inputted. To be more specific, the user inputs the date of birth of the patient being the sample to be measured in accordance with the instructions of display unit 131.

At step S24, a measurement pre-treatment is performed. To be more specific, display unit 131 displays the instructions on the pre-treatment. The user performs the pre-treatment such as heating and stirring of the sample in accordance with the instructions of display unit 131. At step S25, a sample container is set. To be more specific, display unit 131 displays the instructions on the setting of the sample container. The user sets the sample container in specimen analyzer 100 in accordance with the instructions of display unit 131.

At step S26, the sample is measured. When the measurement of the sample finishes, measurement results are printed at step S27. To be more specific, after the measurement finishes, display unit 131 displays a button for starting of the printing. When the user operates the button for starting of the printing, print unit 135 prints the measurement result. The printing results are, for example, the name of the hospital, its location, the name of the measurement apparatus, the date and time of measurement, the operator ID, patient ID, the date of birth of the patient, the measurement results, messages, information on the reference value, and a print end mark.

At step S28, the sample container is removed. To be more specific, display unit 131 displays the instructions for removing the sample container. The user removes the sample container from specimen analyzer 100 in accordance with the instructions of display unit 131. At step S29, determination is made as to whether or not there is a sample container. If there is a sample container, the process returns to step S28, and if there is no sample container, the sample measurement process finishes.

[Display Example of Display Unit]

With reference to FIG. 7 to FIG. 48, a display example of display unit 131 in a case of using specimen analyzer 100 is described. It is possible to operate specimen analyzer 100 by following a series of instructions displayed on display unit 131.

(Display Example when Connecting Ethernet Cable)

Figure 7:
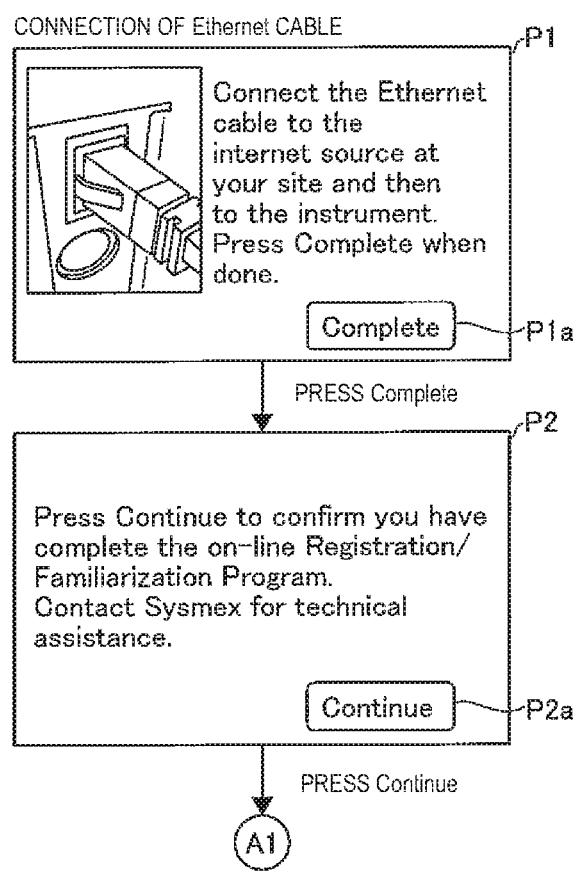
FIG. 7 is a diagram illustrating display example 1 for connecting an Ethernet cable.
Figure 8:
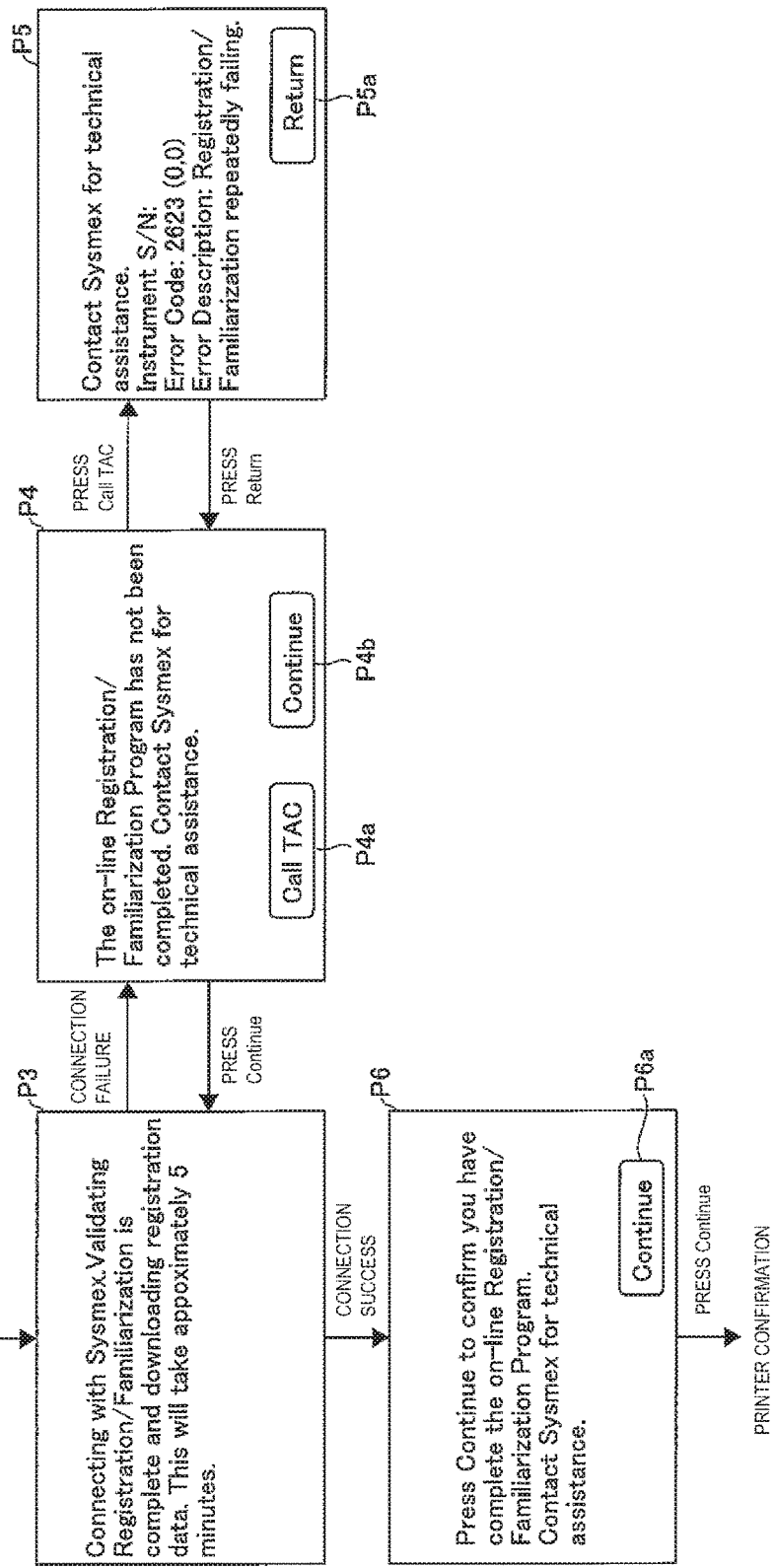
FIG. 8 is a diagram illustrating display example 2 for connecting an Ethernet cable.

With reference to FIG. 7 and FIG. 8, a display example when connecting an Ethernet cable is described.

It is impossible to use specimen analyzer 100 unless it is connected to server 200 via network 250. To be more specific, it is possible to use specimen analyzer 100 if it is registered with server 200. It is necessary to connect to server 200 in order to check whether or not specimen analyzer 100 is registered. Specimen analyzer 100 is connected to network 250 with an Ethernet cable. To this end, it is necessary to connect an Ethernet cable to specimen analyzer 100.

To begin with, when specimen analyzer 100 is set and the power is turned on, display unit 131 first displays a screen for connecting an Ethernet cable. To be more specific, as illustrated in FIG. 7, display unit 131 displays screen P1. Screen P1 shows a picture and an instruction on how to insert the Ethernet cable to specimen analyzer 100. Also, screen P1 shows Complete button P1a. When Complete button P1a is pressed, display unit 131 displays screen P2. Screen P2 shows Continue button P2a. When Continue button P2a is pressed, display unit 131 displays screen P3, as illustrated in FIG. 8. Thus, communication unit 145 of specimen analyzer 100 starts connection to server 200.

If the connection fails while screen P3 is being displayed, display unit 131 displays screen P4. Screen P4 shows Call TAC button P4a and Continue button P4b. When Call TAC button P4a is pressed, display unit 131 displays screen P5. When Continue button P4b is pressed, display unit 131 again displays screen P3.

Screen P5 shows error details. If the user telephones to a TAC (Technical Assistance Center) and communicates the description of screen P5, he/she can receive support smoothly. Screen P5 shows Return button P5a. When Return button P5a is pressed, display unit 131 displays screen P4.

If the connections succeeds while screen P3 is being displayed, display unit 131 displays screen P6. Screen P6 shows Continue button P6a. When Continue button P6a is pressed, the instructions to connect an Ethernet cable stop being displayed. Then, the screen proceeds to a screen of printer confirmation.

(Display Example at Printer Confirmation)

With reference to FIG. 9 to FIG. 12, a display example at printer confirmation is described.

Figure 9:
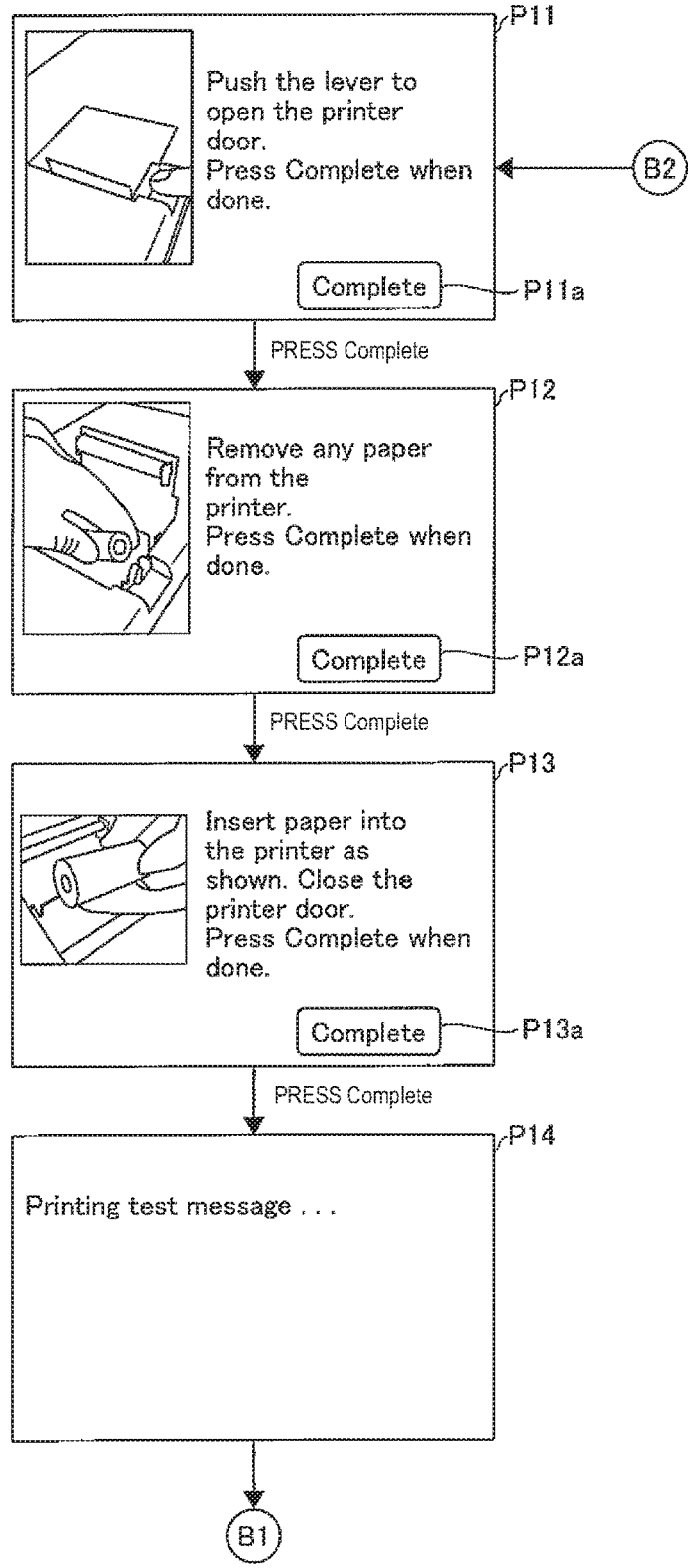
FIG. 9 is a diagram illustrating display example 1 for printer confirmation.

Display unit 131 displays a screen for confirming a printer as print unit 135. As illustrated in FIG. 9, display unit 131 displays screen P11. Screen P11 shows a picture and an instruction on how to open a door of the printer. Also, screen P11 shows Complete button P11a. When Complete button P11a is pressed, display unit 131 displays screen P12. Screen P12 shows a picture and an instruction on how to remove paper from the printer. Also, screen P12 shows Complete button P12a. When Complete button P12a is pressed, display unit 131 displays screen P13.

Screen P13 shows a picture and an instruction on how to insert paper in the printer and close the door. Also, screen P13 shows Complete button P13a. When Complete button P13a is pressed, display unit 131 displays screen P14. Thus, print unit 135 starts test printing.

Figure 10:
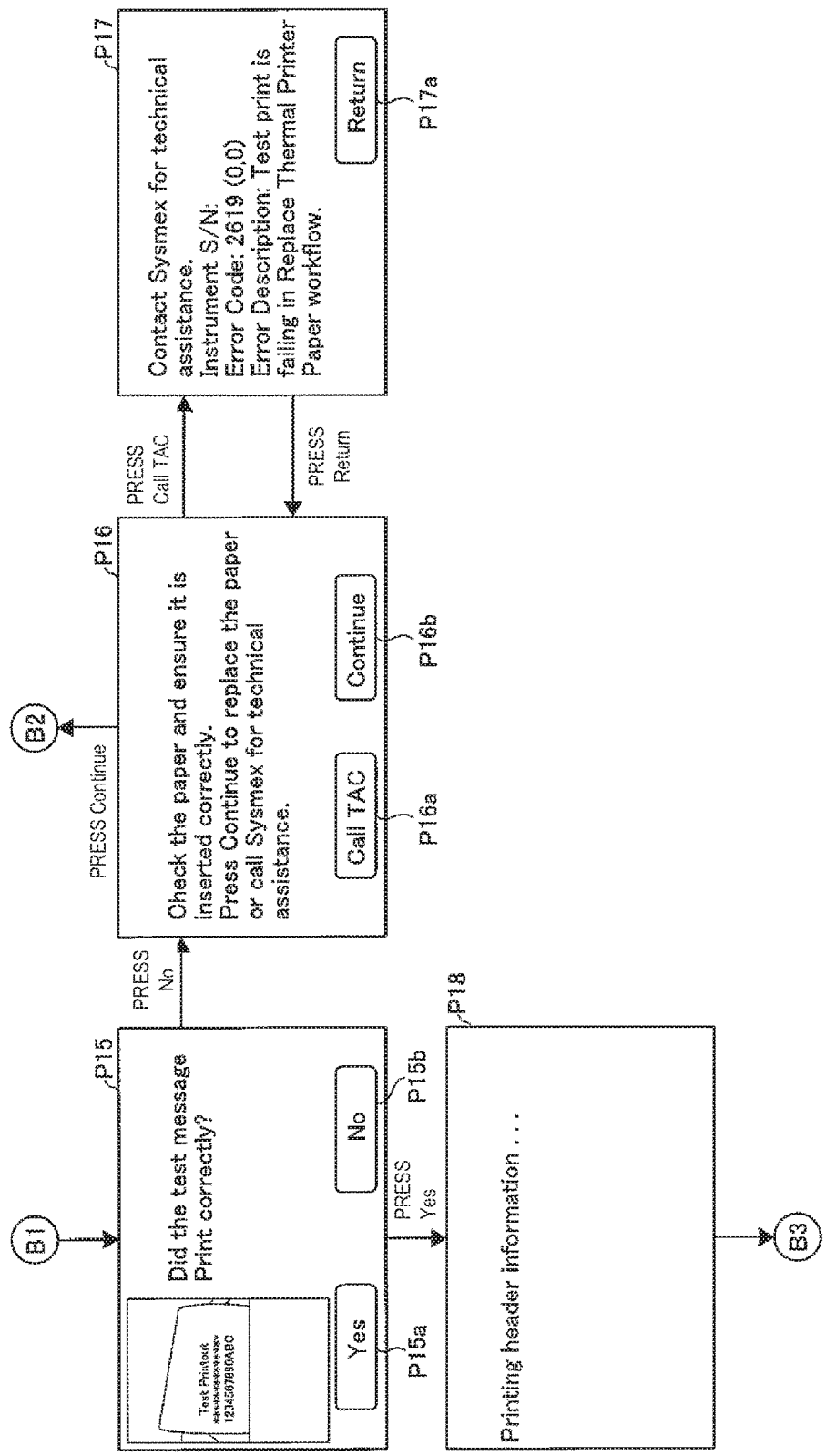
FIG. 10 is a diagram illustrating display example 2 for printer confirmation.

When the test printing finishes, display unit 131 displays screen P15 as illustrated in FIG. 10. Screen P15 shows a question asking whether or not the test printing has been correctly done, Yes button P15a, and No button P15b. When No button P15b is pressed, display unit 131 displays screen P16. When Yes button P15a is pressed, display unit 131 displays screen P18.

Screen P16 shows Call TAC button P16a and Continue button P16b. When Call TAC button P16a is pressed, display unit 131 displays screen P17. When Continue button P16b is pressed, display unit 131 again displays screen P11 (see FIG. 9).

Screen P17 shows error details. If the user telephones to the TAC and communicates the description of screen P17, he/she can receive support smoothly. Screen P17 shows Return button P17a. When Return button P17a is pressed, display unit 131 displays screen P16.

Figure 11:
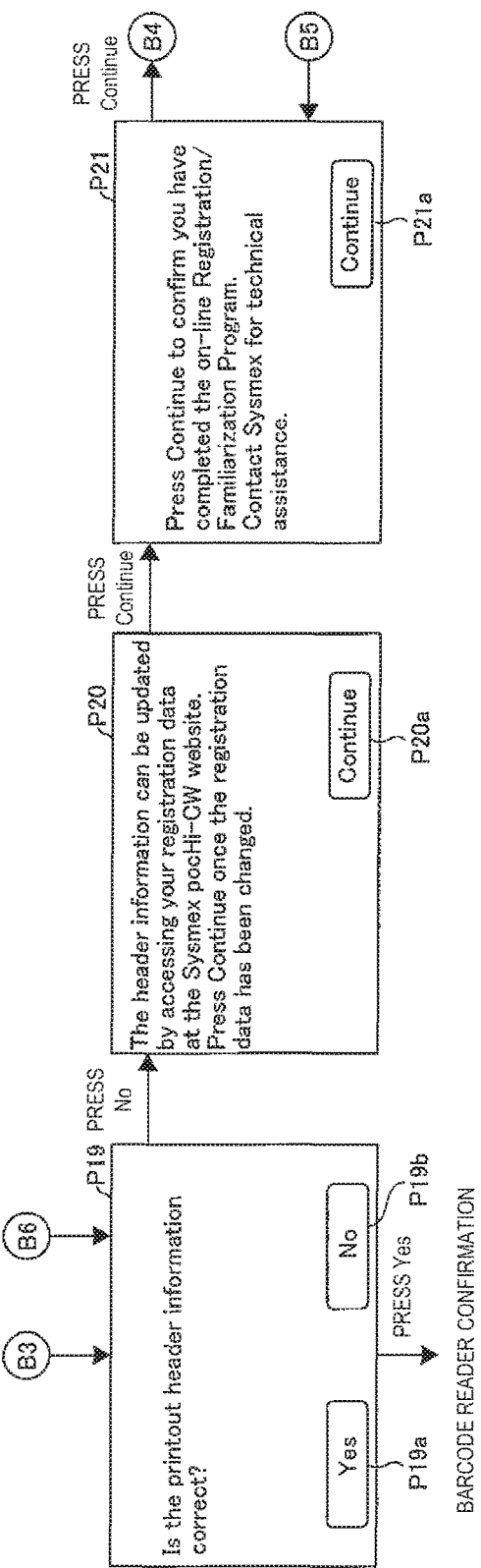
FIG. 11 is a diagram illustrating display example 3 for printer confirmation.

Display unit 131 displays screen P18 and print unit 135 starts printing header information. When the printing of the header information finishes, display unit 131 displays screen P19, as illustrated in FIG. 11. Screen P19 shows a question asking whether or not the header information is correct, Yes button P19a, and No button P19b. When No button P19b is pressed, display unit 131 displays screen P20. When Yes button P19a is pressed, printer confirmation stops being displayed. Then, the screen proceeds to a screen of barcode reader conformation.

Figure 12:
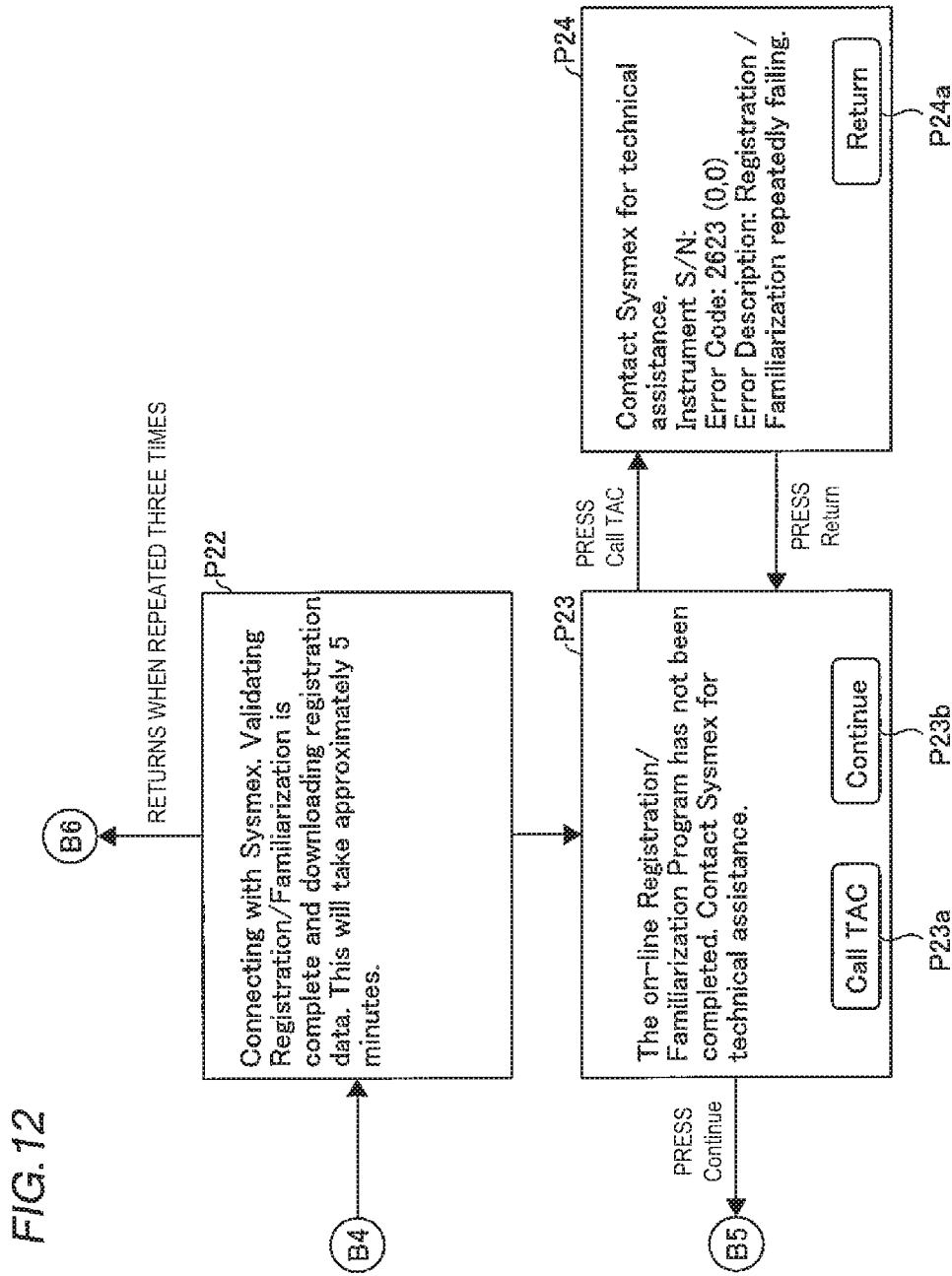
FIG. 12 is a diagram illustrating display example 4 for printer confirmation.

Screen P20 shows a description on update of header information and Continue button P20a. When Continue button P20a is pressed, display unit 131 displays screen P21. Screen P21 shows Continue button P21a. When Continue button P21a is pressed, screen P22 is displayed, as illustrated in FIG. 12.

Screen P22 shows a description on data download. Then, display unit 131 displays screen P23. It is to be noted that if screen P22 is repeated three times, display unit 131 displays screen P19 (see FIG. 11). Screen P23 shows Call TAC button P23a and Continue button P23b. When Call TAC button P23a is pressed, display unit 131 displays screen P24. When Continue button P23b is pressed, display unit 131 again displays screen P21 (see FIG. 11).

Screen P24 shows error details. If the user telephones to the TAC and communicates the description of screen P24, he/she can receive support smoothly. Screen P24 shows Return button P24a. When Return button P24a is pressed, display unit 131 displays screen P23.

As has been illustrated in FIG. 9 to FIG. 11, controller 140 does not proceed to the next process until print sheets 136 are set in print unit 135. Thus, an analysis operation for specimen 101 does not start unless print sheets 136 are set. Hence, it is possible to surely prevent a situation where analysis results 102 are not printed because the print unit is out of paper, and thus to prevent overlooking of analysis results 102.

(Display Example at Barcode Reader Confirmation)

Figure 13:
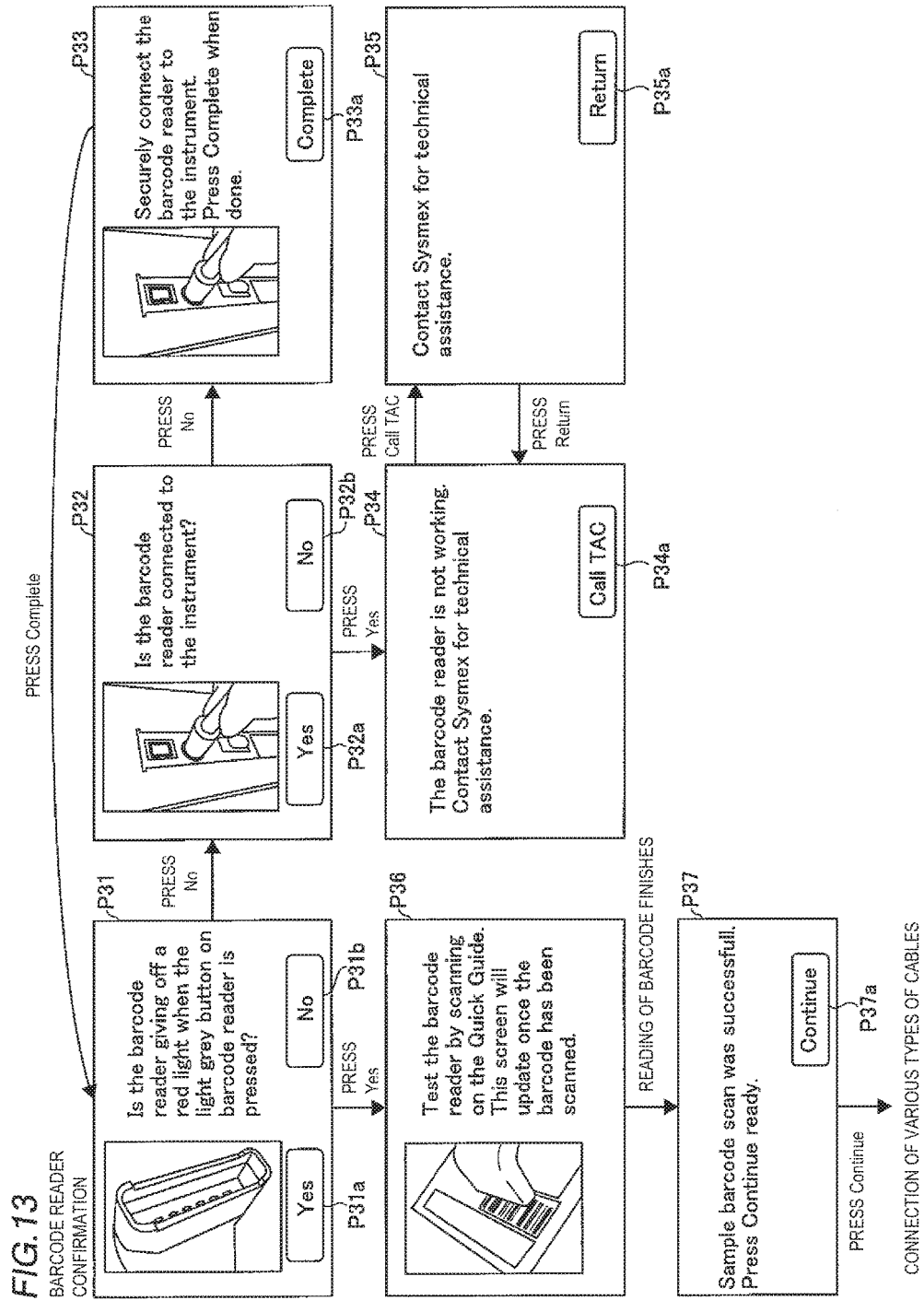
FIG. 13 is a diagram illustrating a display example for barcode reader confirmation.

With reference to FIG. 13, a display example at barcode reader confirmation is described.

Specimen analyzer 100 can input information on a reagent as a consumable and on CELLCLEAN for cleaning only through a barcode reader as information read unit 150. To be more specific, it is necessary to correctly attach a barcode reader to specimen analyzer 100.

As barcode reader confirmation, display unit 131 displays screen P31, as illustrated in FIG. 13. Screen P31 shows a picture of the barcode reader, a question asking whether or not the barcode reader gives off red light when the button is pressed, Yes button P31a, and No button P31b. When No button P31b is pressed, display unit 131 displays screen P32. When Yes button P31a is pressed, display unit 131 displays screen P36.

Screen P32 shows a picture instructing to connect the barcode reader, a question asking whether or not the barcode reader is connected to specimen analyzer 100, Yes button P32a, and No button P32b. When No button P32b is pressed, display unit 131 displays screen P33. When Yes button P32a is pressed, display unit 131 displays screen P34. Screen P33 shows a picture and an instruction on how to connect the barcode reader. Also, screen P33 shows Complete button P33a. When Complete button P33a is pressed, display unit 131 displays screen P31.

Screen P34 shows a description on a problem with the barcode reader and Call TAC button P34a. When Call TAC button P34a is pressed, display unit 131 displays screen P35. Screen P35 shows Return button P35a. When Return button P35a is pressed, display unit 131 displays screen P34.

Screen P36 shows a picture and an instruction on how to read the barcode of the Quick Guide using the barcode reader. When the barcode reader completes reading the barcode of the Quick Guide, display unit 131 displays screen P37. Screen P37 shows Continue button P37a. When Continue button P37a is pressed, the screen of barcode reader confirmation finishes being displayed. Then, the screen proceeds to a screen of the connection of various types of tubes.

(Display Example at Connection of Various Types of Tubes)

Figure 14:
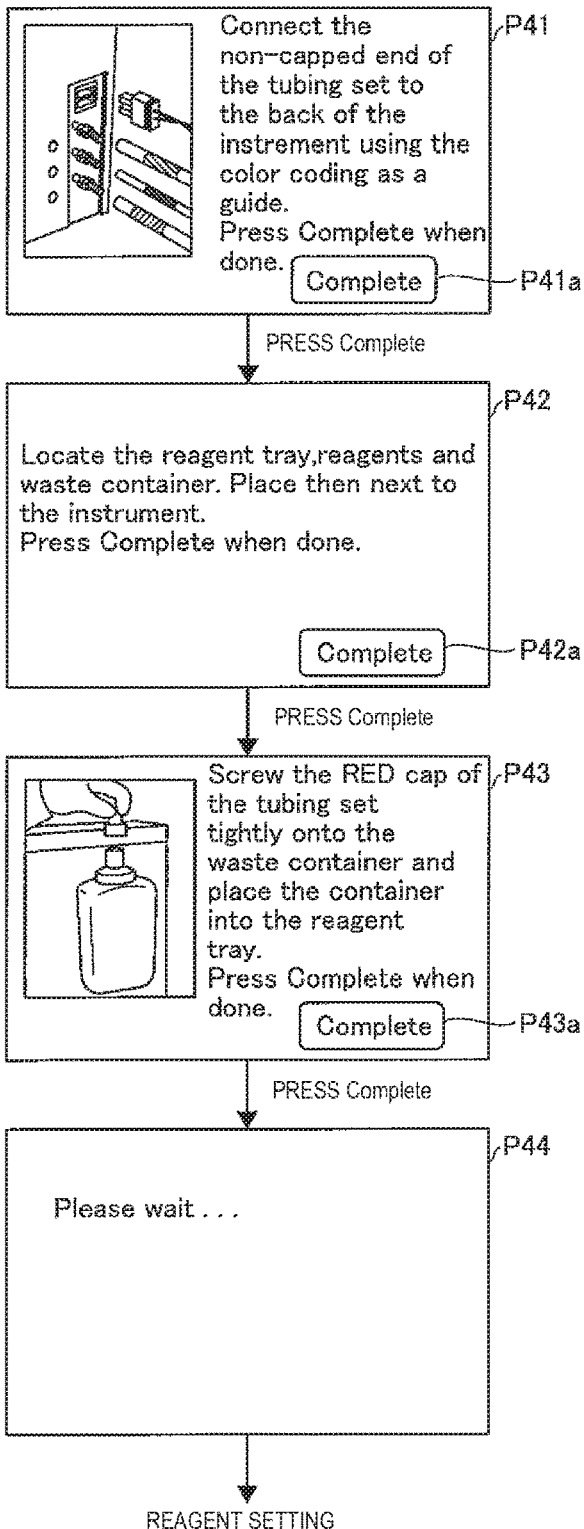
FIG. 14 is a diagram illustrating a display example for connecting various types of tubes.

With reference to FIG. 14, a display example at the connection of various types of tubes is described.

Display unit 131 displays screen P41 in order to connect various types of tubes to specimen analyzer 100, as illustrated in FIG. 14. Screen P41 shows a picture and an instruction on how to connect various types of tubes to specimen analyzer 100. Also, screen P41 shows Complete button P41a. When Complete button P41a is pressed, display unit 131 displays screen P42. Screen P42 shows instructions to place a reagent container, a waste liquid container etc. to be connected to tubes next to specimen analyzer 100. Also, screen P42 shows Complete button P42a. When Complete button P42a is pressed, display unit 131 displays screen P43.

Screen P43 shows a picture and an instruction on how to connect the waste liquid container. Also, screen P43 shows Complete button P43a. When Complete button P43a is pressed, display unit 131 displays screen P44. Finally, the screen on connecting various types of tubes finishes being displayed. Then, the screen proceeds to a screen of reagent setting.

(Display Example when Setting Reagent)

With reference to FIG. 15 to FIG. 21, a display example when setting a reagent is described.

Figure 15:
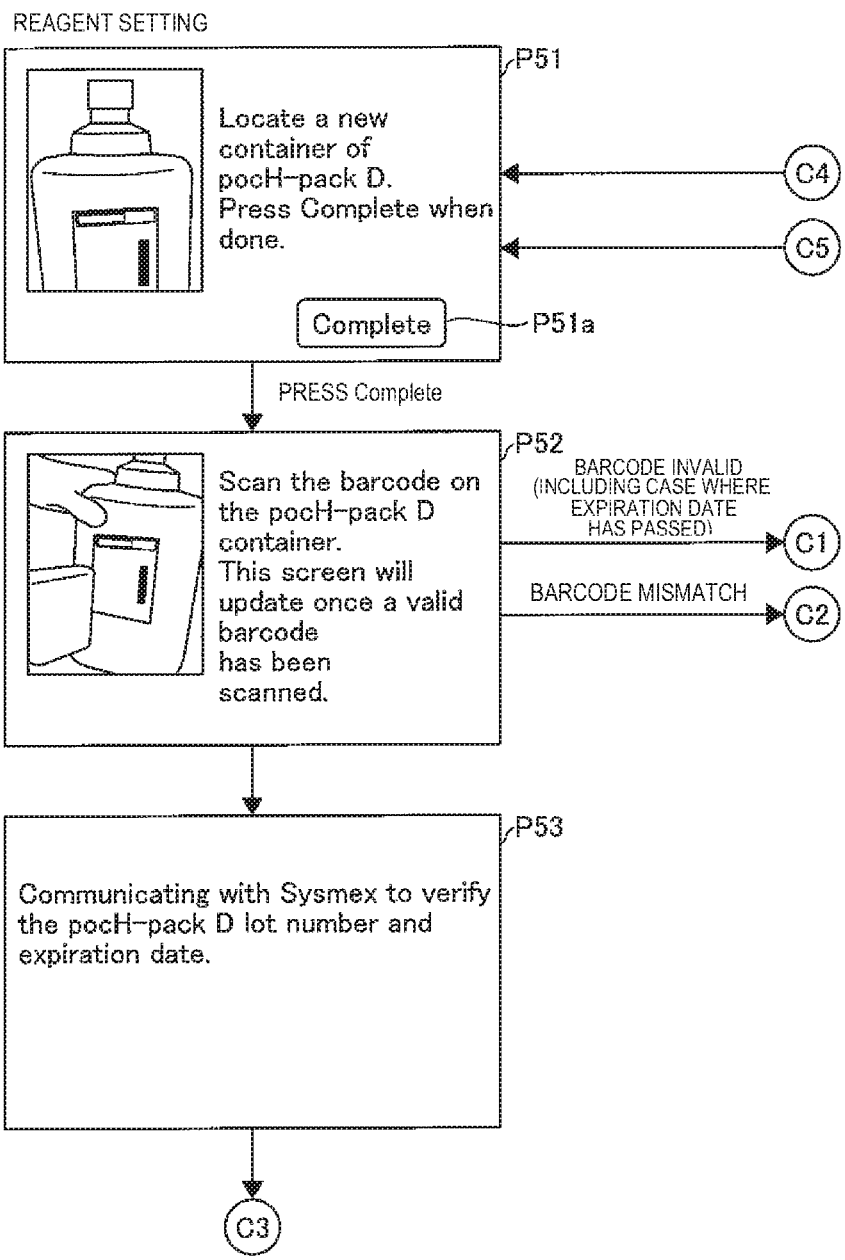
FIG. 15 is a diagram illustrating display example 1 for setting a reagent.

Display unit 131 displays screen P51 in order to set a reagent, as illustrated in FIG. 15. Screen P51 shows a picture and an instruction on how to set a container of a diluted solution used to analyze a specimen. Also, screen P51 shows Complete button P51a. When Complete button P51a is pressed, display unit 131 displays screen P52. Screen P52 shows a picture and an instruction on how to read a barcode attached on the container of the diluted solution. When the barcode is correctly read, display unit 131 displays screen P53. If a barcode is invalid, including the case where the expiration date has passed, display unit 131 displays screen P54 (see FIG. 16). If the barcode does not match, display unit 131 displays screen P55 (see FIG. 16).

While screen P53 is being displayed, connection is established to server 200, and whether or not the reagent can be used is checked. Thereafter, display unit 131 displays screen P57 (see FIG. 17).

Figure 16:
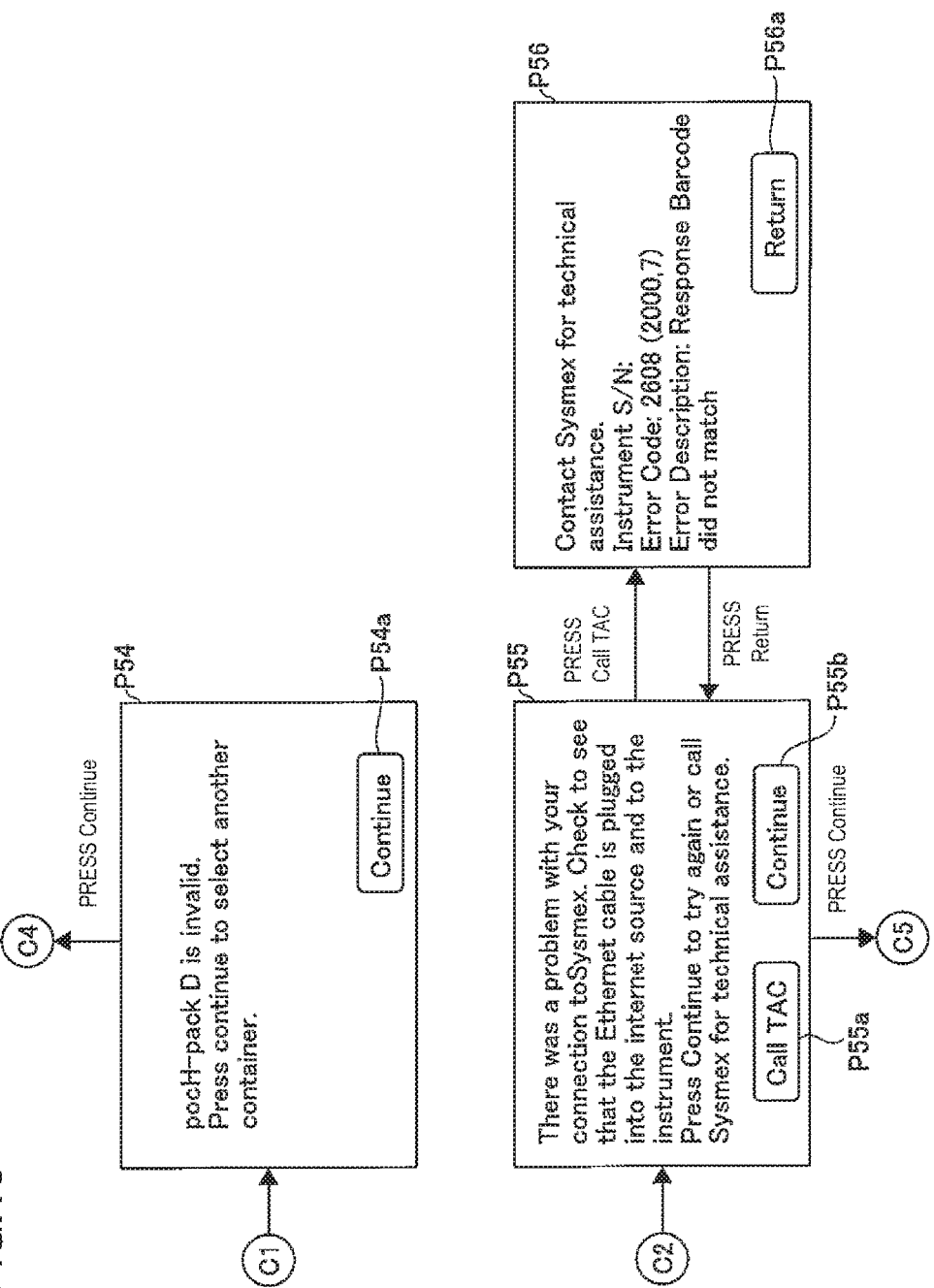
FIG. 16 is a diagram illustrating display example 2 for setting a reagent.

As illustrated in FIG. 16, screen P54 shows a description that the reagent of the read barcode is invalid. Also, screen P54 shows Continue button P54a. When Continue button P54a is pressed, display unit 131 displays screen P51 (see FIG. 15).

Screen P55 shows a description that there is a problem with the connection. Also, screen P55 shows Call TAC button P55a and Continue button P55b. When Call TAC button P55a is pressed, display unit 131 displays screen P56. When Continue button P55b is pressed, display unit 131 displays screen P51 (see FIG. 15). Screen P56 shows error details. If the user telephones to the TAC and communicates the description of screen P56, he/she can receive support smoothly. Screen P56 shows Return button P56a. When Return button P56a is pressed, display unit 131 displays screen P55.

Figure 17:
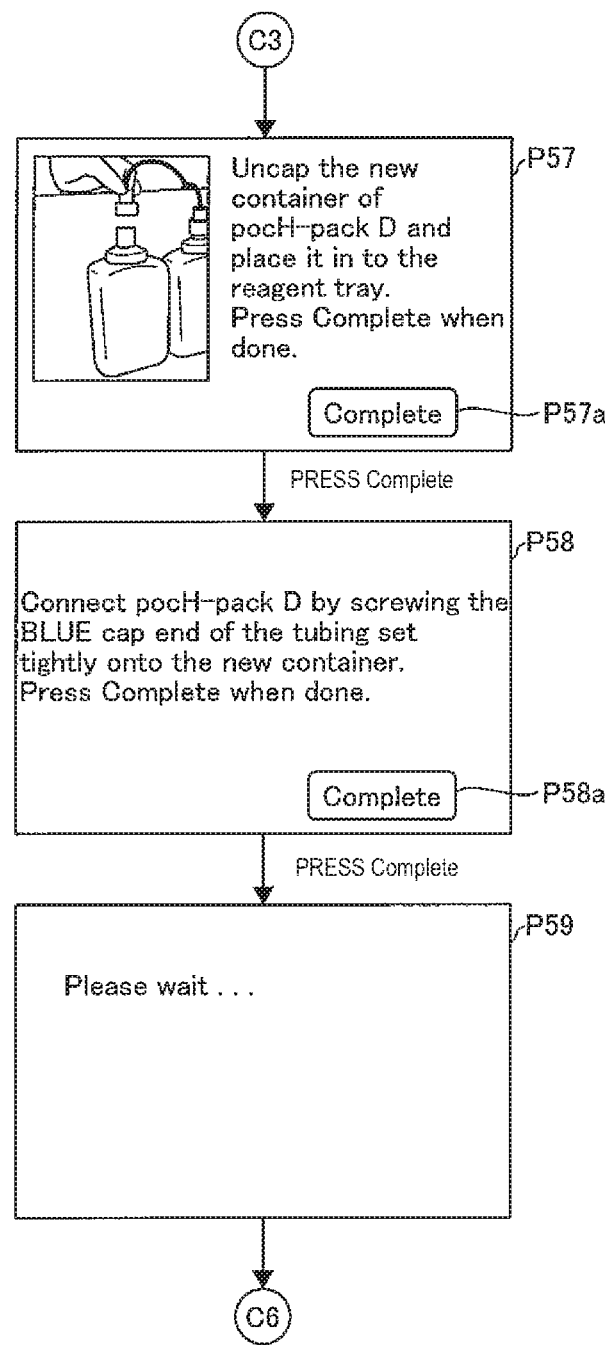
FIG. 17 is a diagram illustrating display example 3 for setting a reagent.
Figure 18:
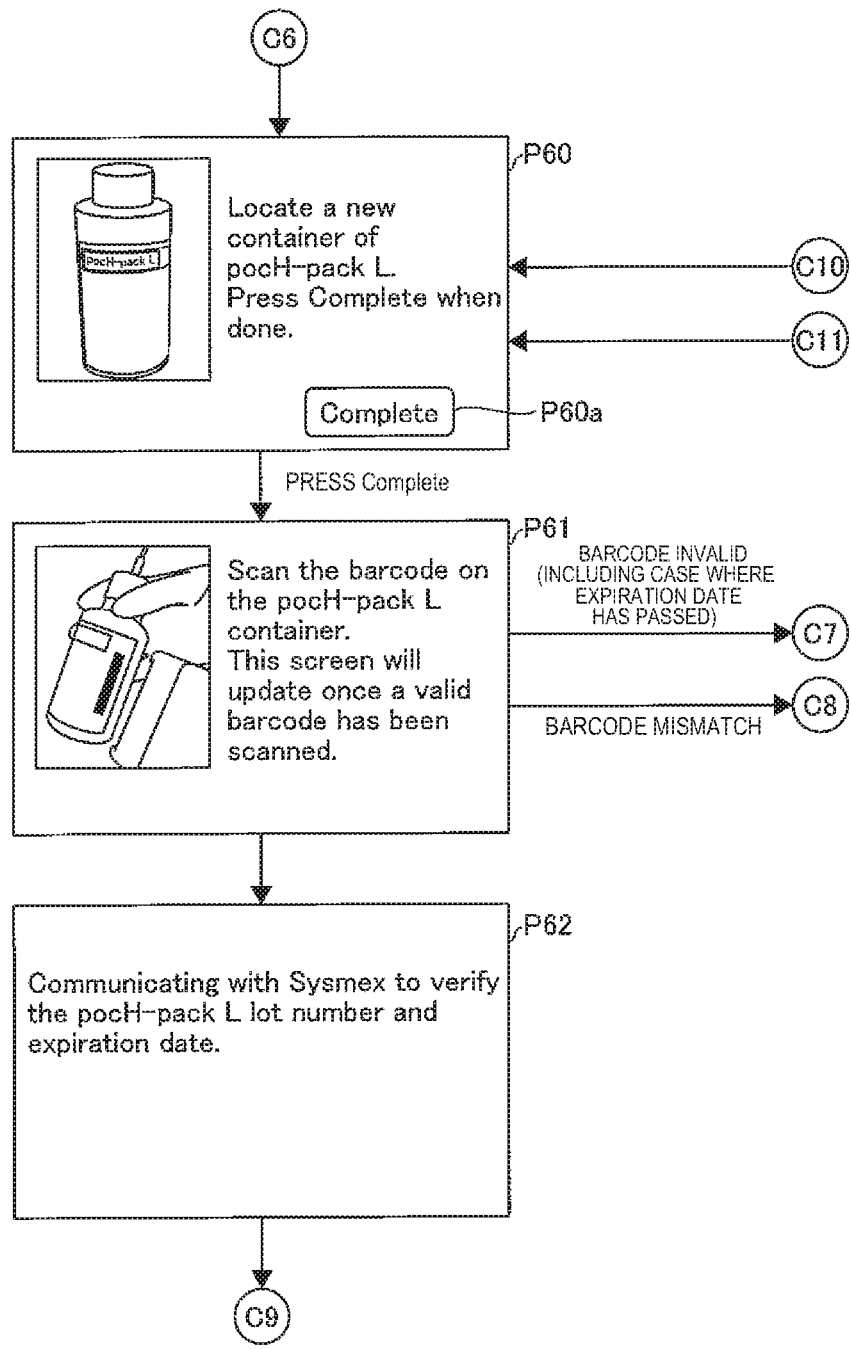
FIG. 18 is a diagram illustrating display example 4 for setting a reagent.

As illustrated in FIG. 17, screen P57 shows a picture and an instruction on how to place the reagent container. Also, screen P57 shows Complete button P57a. When Complete button P57a is pressed, display unit 131 displays screen P58. Screen P58 shows a description to connect the reagent container and the tube together. Also, screen P58 shows Complete button P58a. When Complete button P58a is pressed, display unit 131 displays screen P59. Thereafter, as illustrated in FIG. 18, display unit 131 displays screen P60.

Screen P60 shows a picture and an instruction on how to set a container of a hemolyzer used to analyze a specimen. Also, screen P60 shows Complete button P60a. When Complete button P60a is pressed, display unit 131 displays screen P61. Screen P61 shows a picture and an instruction on how to read a barcode attached on the container of the hemolyzer. When the barcode is correctly read, display unit 131 displays screen P62. If a barcode is invalid, including the case where the expiration date has passed, display unit 131 displays screen P63 (see FIG. 19). If the barcode does not match, display unit 131 displays screen P64 (see FIG. 19).

While screen P62 is being displayed, connection is established to server 200, and whether or not the reagent can be used is checked. Thereafter, display unit 131 displays screen P66 (see FIG. 20).

Figure 19:
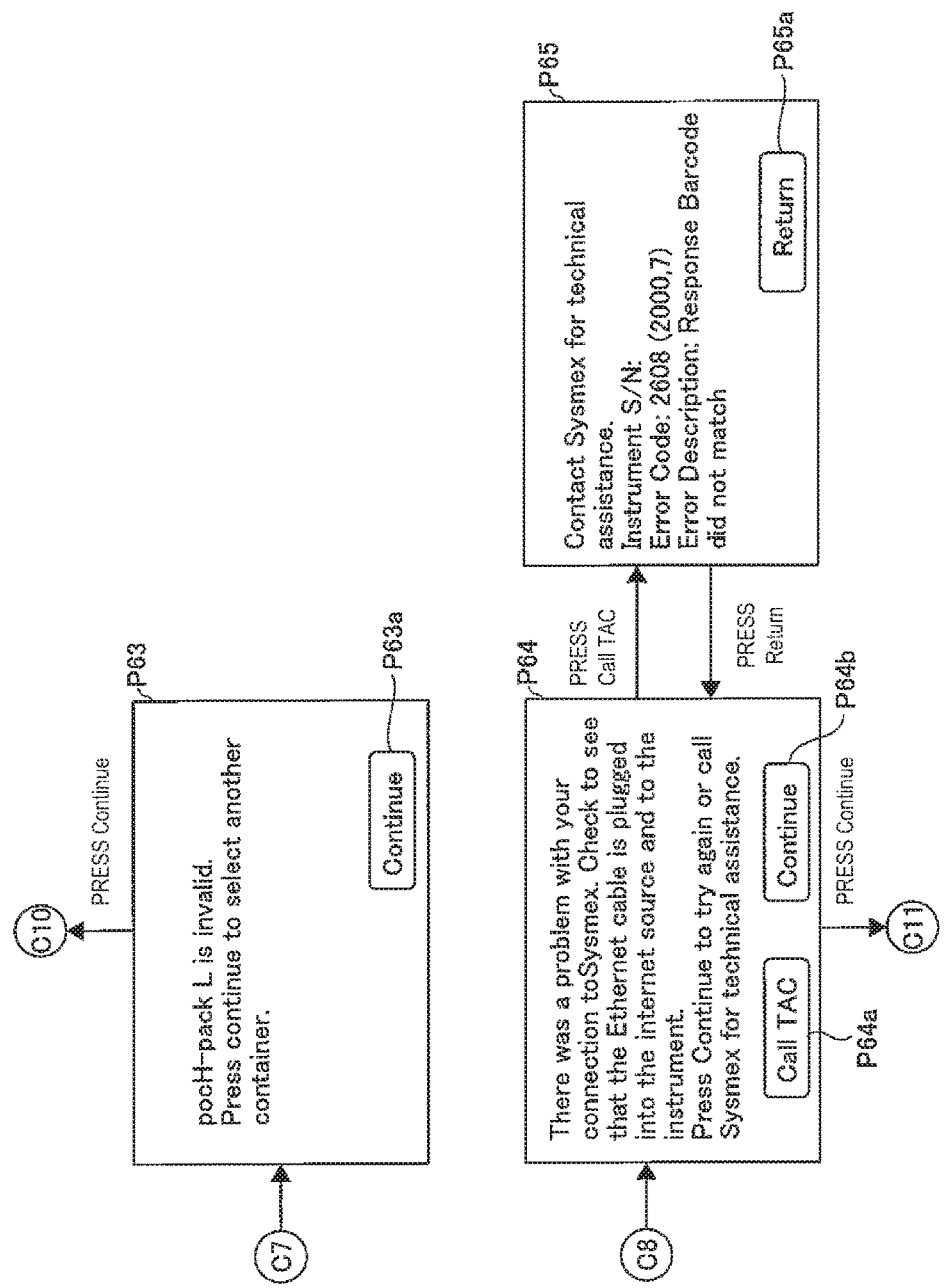
FIG. 19 is a diagram illustrating display example 5 for setting a reagent.

As illustrated in FIG. 19, screen P63 shows a description that the reagent of the read barcode is invalid. Also, screen P63 shows Continue button P63a. When Continue button P63a is pressed, display unit 131 displays screen P60 (see FIG. 18).

Screen P64 shows a description that there is a problem with the connection. Also, screen P64 shows Call TAC button P64a and Continue button P64b. When Call TAC button P64a is pressed, display unit 131 displays screen P65. When Continue button P64b is pressed, display unit 131 displays screen P60 (see FIG. 18). Screen P65 shows error details. If the user telephones to the TAC and communicates the description of screen P65, he/she can receive support smoothly. Screen P65 shows Return button P65a. When Return button P65a is pressed, display unit 131 displays screen P64.

Figure 20:
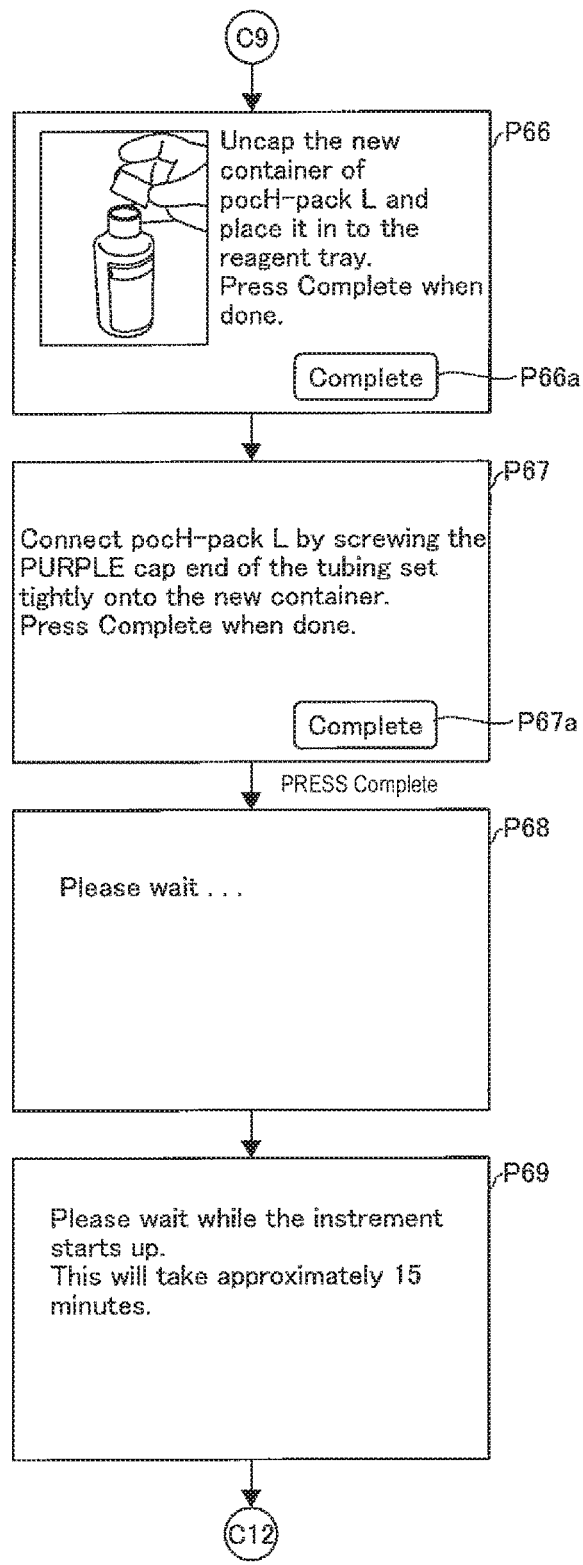
FIG. 20 is a diagram illustrating display example 6 for setting a reagent.

As illustrated in FIG. 20, screen P66 shows a picture and an instruction on how to place the reagent container. Also, screen P66 shows Complete button P66a. When Complete button P66a is pressed, display unit 131 displays screen P67. Screen P67 shows a description to connect the reagent container and the tube together. Also, screen P67 shows Complete button P67a. When Complete button P67a is pressed, display unit 131 displays screen P68. Thereafter, display unit 131 displays screen P69.

Figure 21:
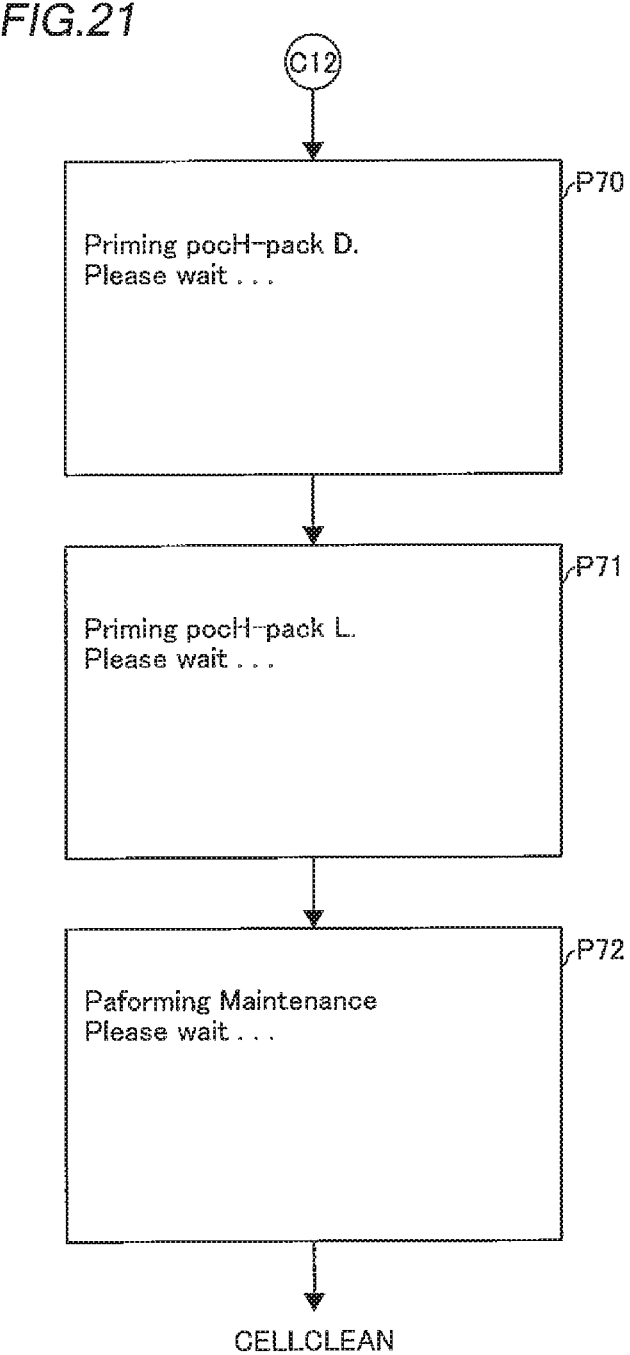
FIG. 21 is a diagram illustrating display example 7 for setting a reagent.

Subsequently, as illustrated in FIG. 21, display unit 131 displays screen P70. In addition, the diluted solution is fed to specimen analyzer 100. Thereafter, display unit 131 displays screen P71. Moreover, the hemolyzer is fed to specimen analyzer 100. Thereafter, display unit 131 displays screen P72. Finally, the screen of setting the reagent finished being displayed. Then, the screen proceeds to a screen of cleaning by CELLCLEAN.

(Display Example of Cleaning by CELLCLEAN)

With reference to FIG. 22 to FIG. 25, a display example of cleaning by CELLCLEAN is described.

Figure 22:
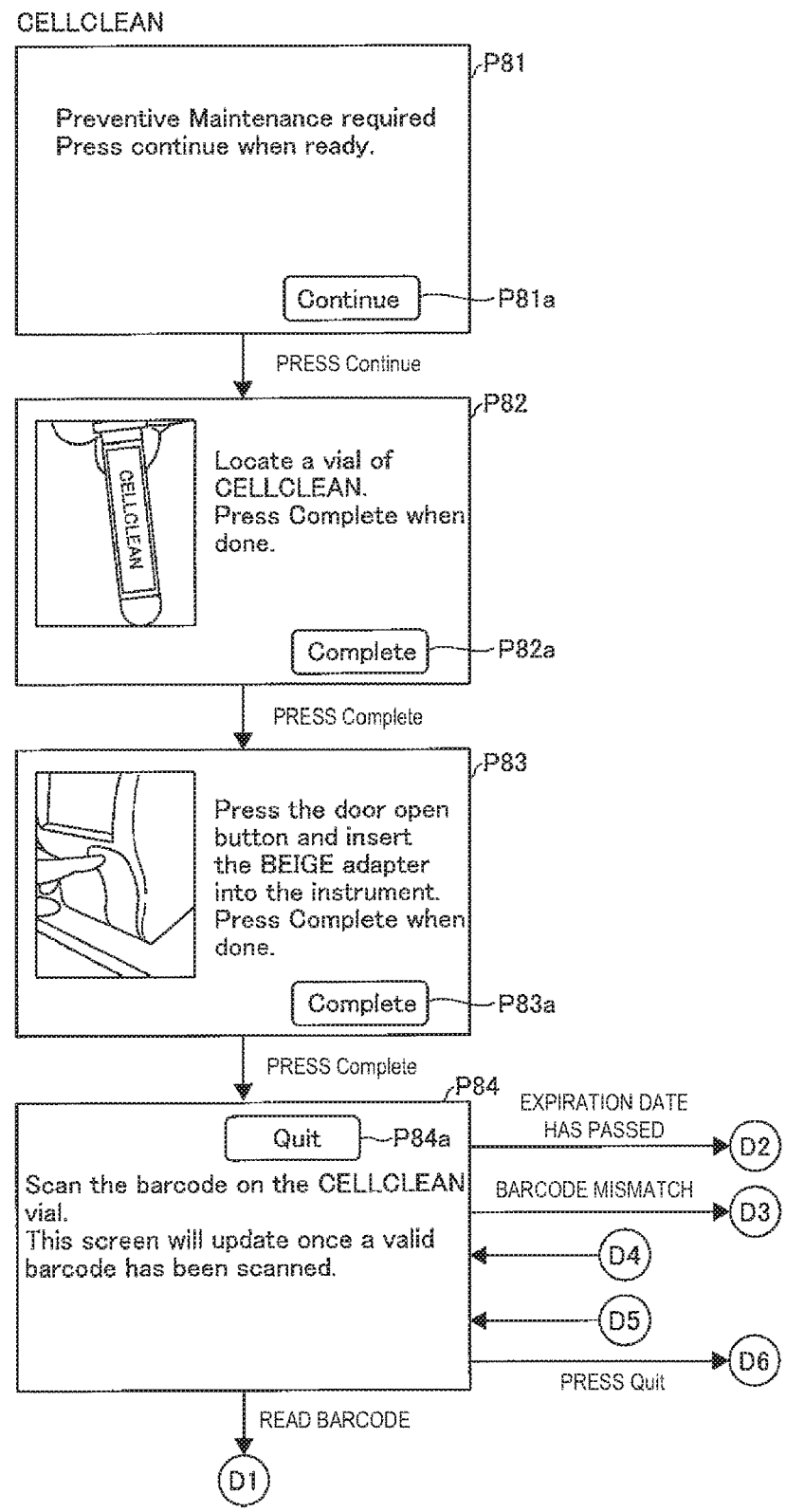
FIG. 22 is a diagram illustrating display example 1 for cleaning by CELLCLEAN.
Figure 23:
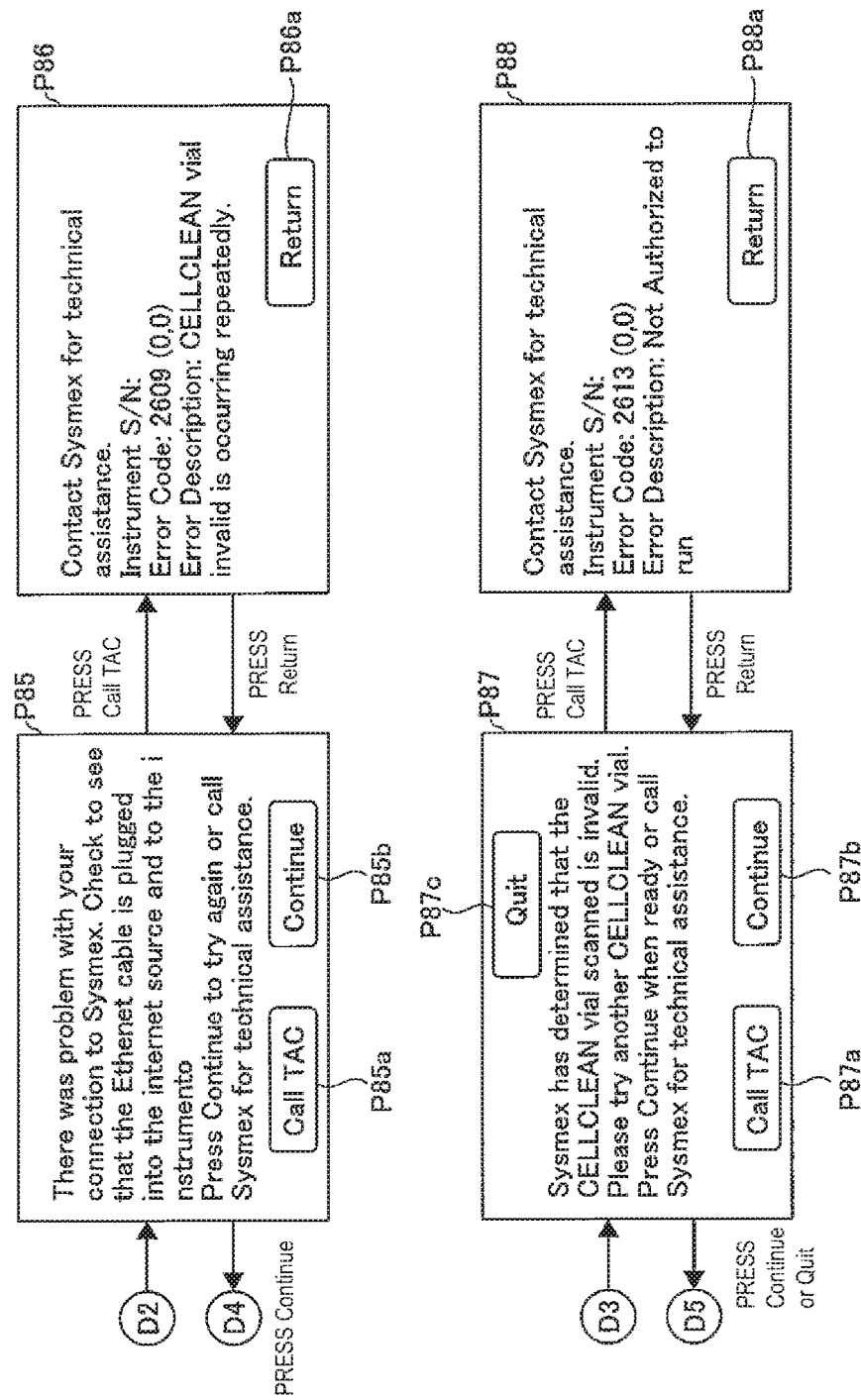
FIG. 23 is a diagram illustrating display example 2 for cleaning by CELLCLEAN.

As illustrated in FIG. 22, display unit 131 displays screen P81 in order to indicate the necessity of cleaning by CELL- CLEAN. Screen P81 shows Continue button P81a. When Continue button P81a is pressed, display unit 131 displays screen P82. Screen P82 shows a picture and an instruction on CELLCLEAN to be used. Also, screen P82 shows Complete button P82a. When Complete button P82a is pressed, display unit 131 displays screen P83.

Screen P83 shows a picture and an instruction on how to open a door and insert an adapter. Also, screen P83 shows Complete button P83a. When Complete button P83a is pressed, display unit 131 displays screen P84. Screen P84 shows a description to read a barcode attached on the container of CELLCLEAN. Also, screen P84 shows Quit button P84a. When the barcode is correctly read, display unit 131 displays screen P89 (see FIG. 24). In the case where the expiration date has passed, display unit 131 displays screen P85 (see FIG. 23). If the barcode does not match, display unit 131 displays screen P87 (see FIG. 23). When Quit button P84a is pressed, display unit 131 displays screen P91 (see FIG. 24).

Screen P85 shows a description that there is a problem with the connection. Also, screen P85 shows Call TAC button P85a and Continue button P85b. When Call TAC button P85a is pressed, display unit 131 displays screen P86. When Continue button P85b is pressed, display unit 131 displays screen P84 (see FIG. 22). Screen P86 shows error details. If the user telephones to the TAC and communicates the description of screen P86, he/she can receive support smoothly. Screen P86 shows Return button P86a. When Return button P86a is pressed, display unit 131 displays screen P85.

Screen P87 shows a description that CELLCLEAN is invalid. Also, screen P87 shows Call TAC button P87a, Continue button P87b, and Quit button P87c. When Call TAC button P87a is pressed, display unit 131 displays screen P88. When Continue button P87b or Quit button P87c is pressed, display unit 131 displays screen P84 (see FIG. 22). Screen P88 shows error details. If the user telephones to the TAC and communicates the description of screen P88, he/she can receive support smoothly. Screen P88 shows Return button P88a. When Return button P88a is pressed, display unit 131 displays screen P87.

Figure 24:
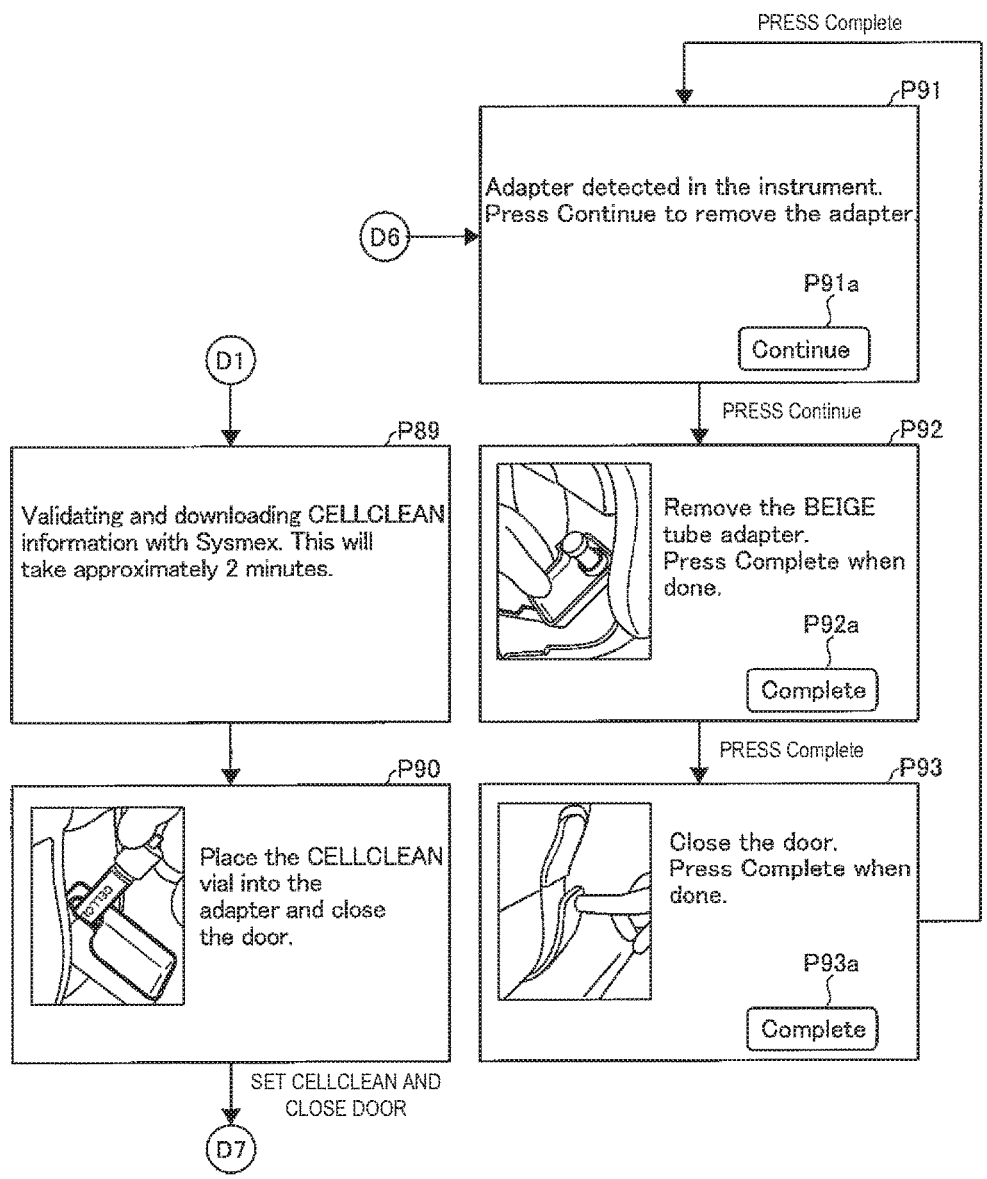
FIG. 24 is a diagram illustrating display example 3 for cleaning by CELLCLEAN.

As illustrated in FIG. 24, screen P89 shows a description on validation and download of CELLCLEAN information. Thereafter, display unit 131 displays screen P90. Screen P90 shows a picture and an instruction on how to place CELLCLEAN. After CELLCLEAN is placed and the door is closed, display unit 131 displays screen P94 (see FIG. 25).

Screen P91 shows a description that the adapter is set and Continue button P91a. When Continue button P91a is pressed, display unit 131 displays screen P92. Screen P92 shows a picture and an instruction on how to remove the adapter. Also, screen P92 shows Complete button P92a. When Complete button P92a is pressed, display unit 131 displays screen P93. Screen P93 shows a picture and an instruction on how to close the door. Also, screen P93 shows Complete button P93a. When Complete button P93a is pressed, display unit 131 displays screen P91.

Figure 25:
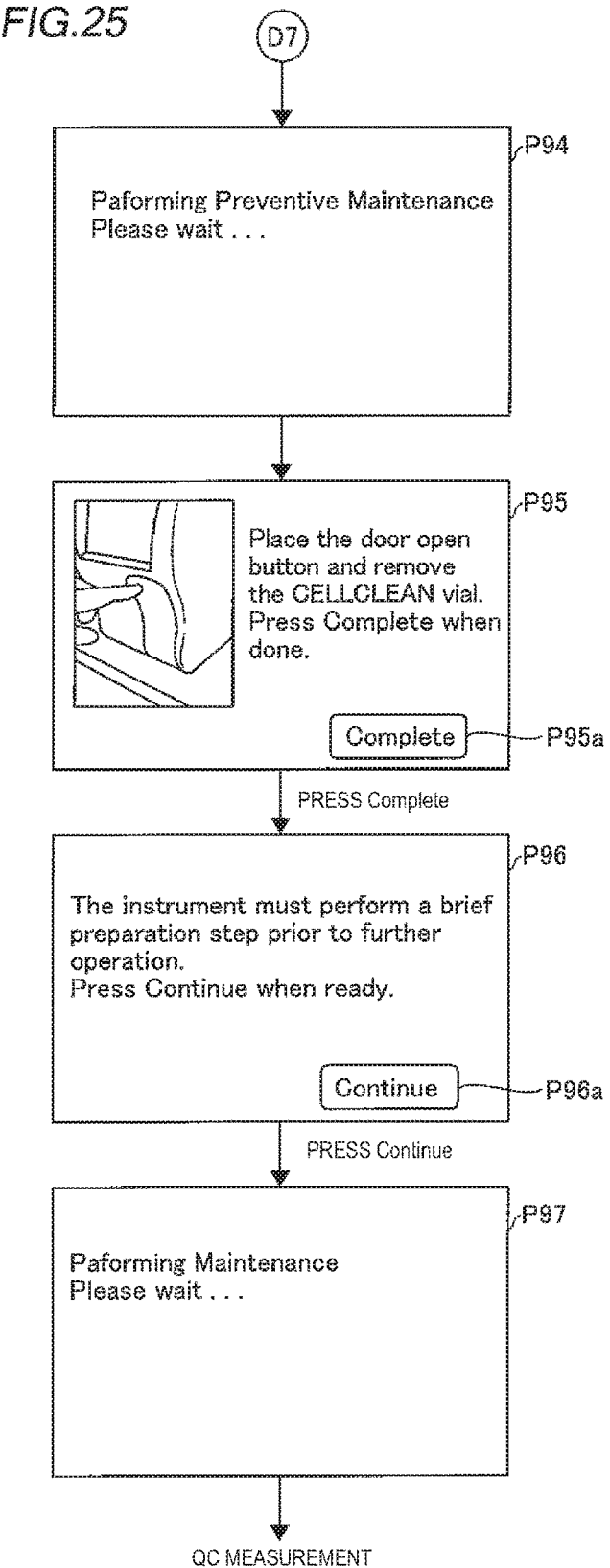
FIG. 25 is a diagram illustrating display example 4 for cleaning by CELLCLEAN.

As illustrated in FIG. 25, display unit 131 displays screen P94. Also, CELLCLEAN cleans the inside of specimen analyzer 100. Thereafter, display unit 131 displays screen P95. Screen P95 shows a picture and an instruction on how to remove the container of CELLCLEAN from specimen analyzer 100. Also, screen P95 shows Complete button P95a. When Complete button P95a is pressed, display unit 131 shows screen P96.

Screen P96 shows a description to prepare specimen analyzer 100 and Continue button P96a. When Continue button P96a is pressed, display unit 131 displays screen P97. Also, the preparation of specimen analyzer 100 proceeds. Finally, the screen of cleaning by CELLCLEAN finishes being displayed. Then, the screen proceeds to a screen of QC measurement.

(Display Example at QC Measurement)

With reference to FIG. 26 to FIG. 32, a display example at QC measurement is described.

Figure 26:
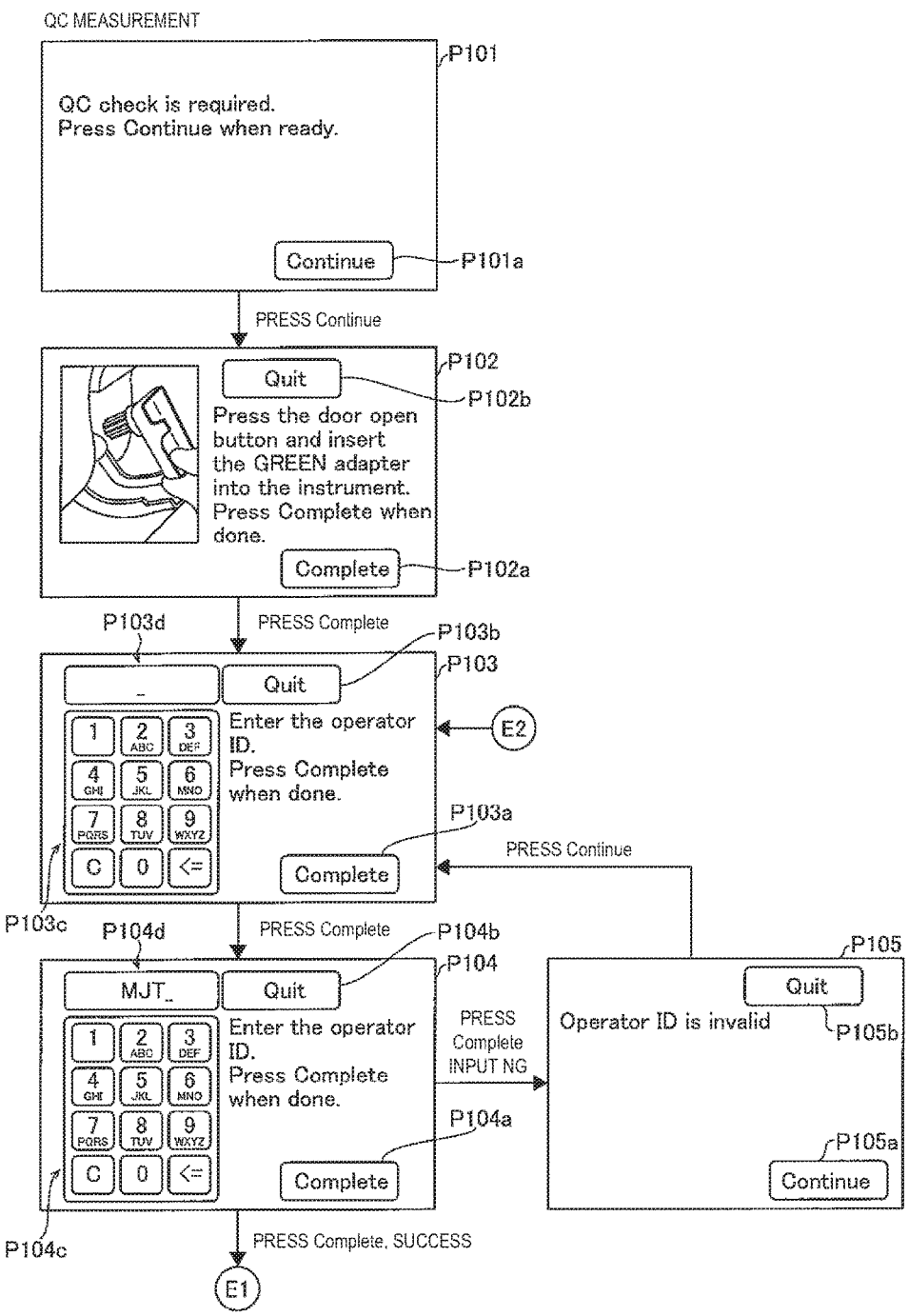
FIG. 26 is a diagram illustrating display example 1 for QC measurement.

As illustrated in FIG. 26, display unit 131 displays screen P101 in order to indicate the necessity of QC (Quality Control) measurement. Screen P101 shows Continue button P101a. When Continue button P101a is pressed, display unit 131 displays screen P102. Screen P102 shows a picture and an instruction on how to open the door and insert the adapter. Also, screen P102 shows Complete button P102a. When Complete button P102a is pressed, display unit 131 displays screen P103.

Screen P103 shows a description to input the ID of the operator. Also, screen P103 shows Complete button P103a, Quit button P103b, input buttons P103c, and input region P103d. When input buttons P103c are operated, input region P103d displays inputted characters. The ID of the operator can be set using, for example, any one to three alphabetical letters. Also, the ID of the operator may be different for each of the High, Low, and Normal QC reagents.

When Complete button P103a is pressed, display unit 131 displays screen P104. In the example of FIG. 26, the string "MJT" is inputted as the ID of the operator. Screen P104 shows Complete button P104a, Quit button P104b, input buttons P104c, and input region P104d. When the pressing of Complete button P104a succeeds, display unit 131 displays screen P106 (see FIG. 27). When Complete button P104a is pressed but the input is NG, display unit 131 displays screen P105.

Screen P105 shows a description that the operator ID is invalid, Continue button P105a, and Quit button P105b. When Continue button P105a is pressed, display unit 131 displays screen P103.

Figure 27:
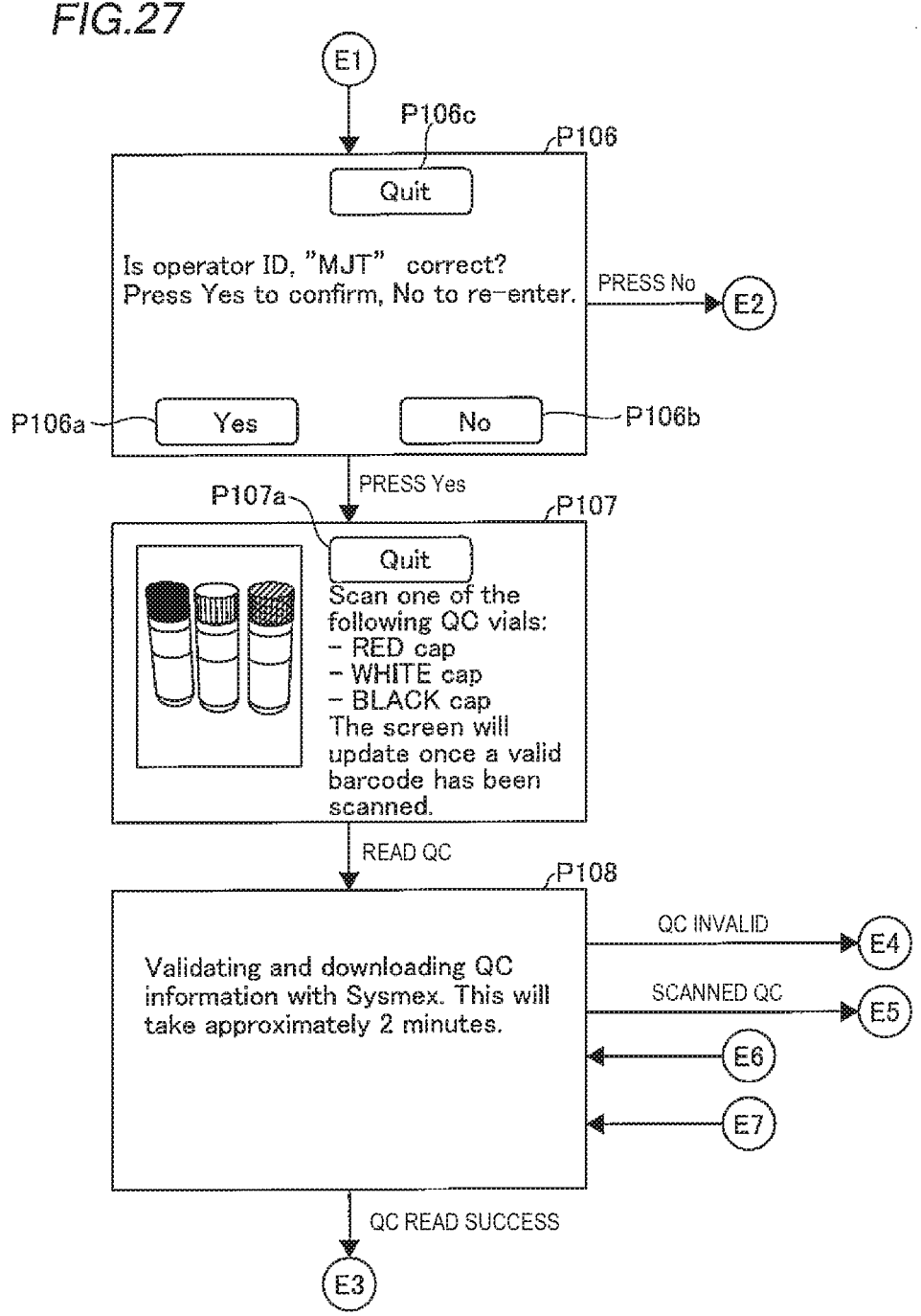
FIG. 27 is a diagram illustrating display example 2 for QC measurement.

As illustrated in FIG. 27, screen P106 shows a question asking whether or not the operator ID is correct, Yes button P106a and No button P106b, and Quit button P106c. When No button P106b is pressed, display unit 131 displays screen P103. When Yes button P106a is pressed, display unit 131 displays screen P107.

Screen P107 shows a picture and an instruction on how to read a barcode of a High QC reagent. Also, screen P107 shows Quit button P107a. When the barcode of the QC reagent is read, display unit 131 displays screen P108. Screen P108 shows a description on validation and download of information on the QC reagent. Once information on the QC reagent is downloaded from server 200, a range of the measurement value of the QC reagent is obtained.

Figure 28:
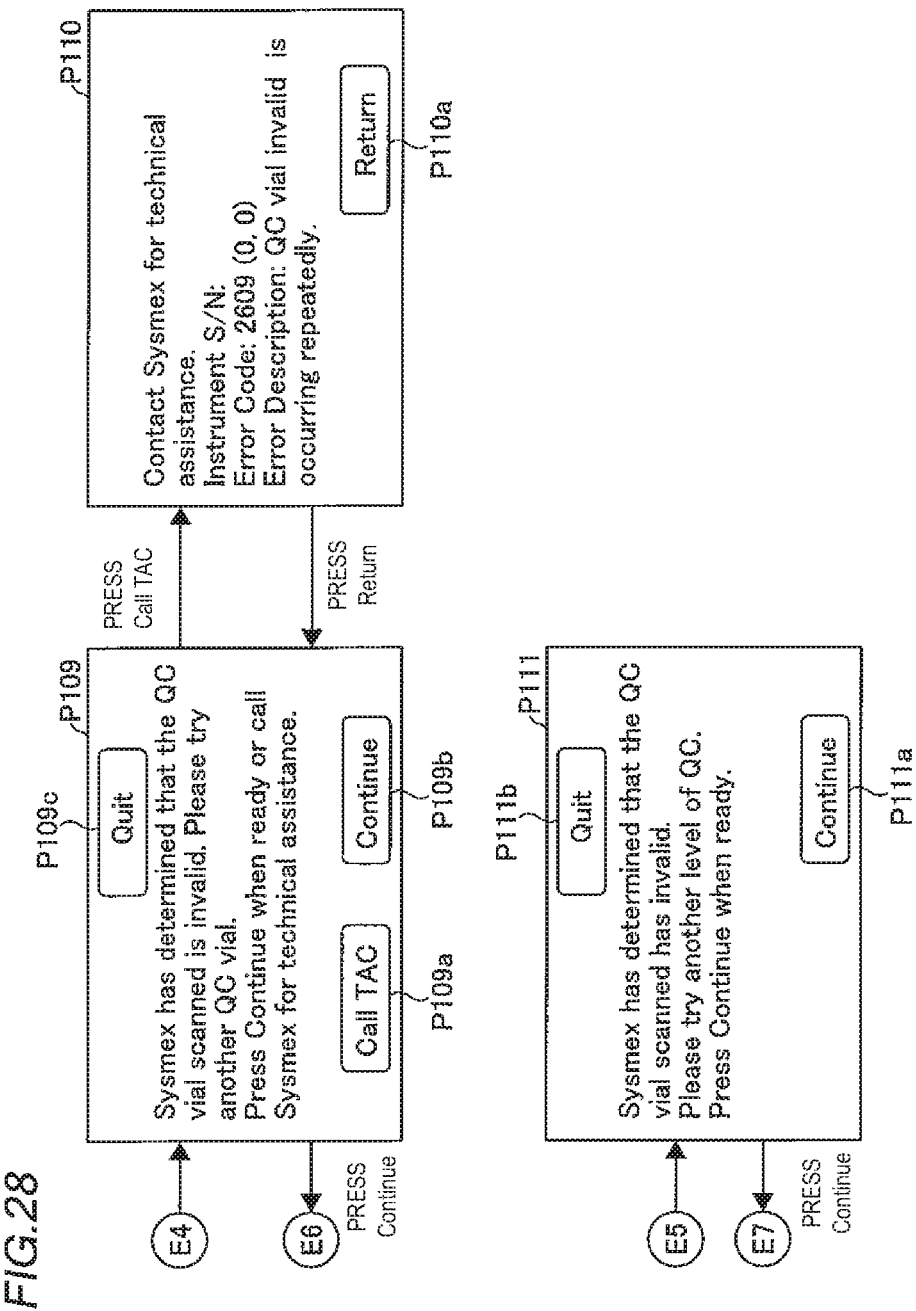
FIG. 28 is a diagram illustrating display example 3 for QC measurement.
Figure 29:
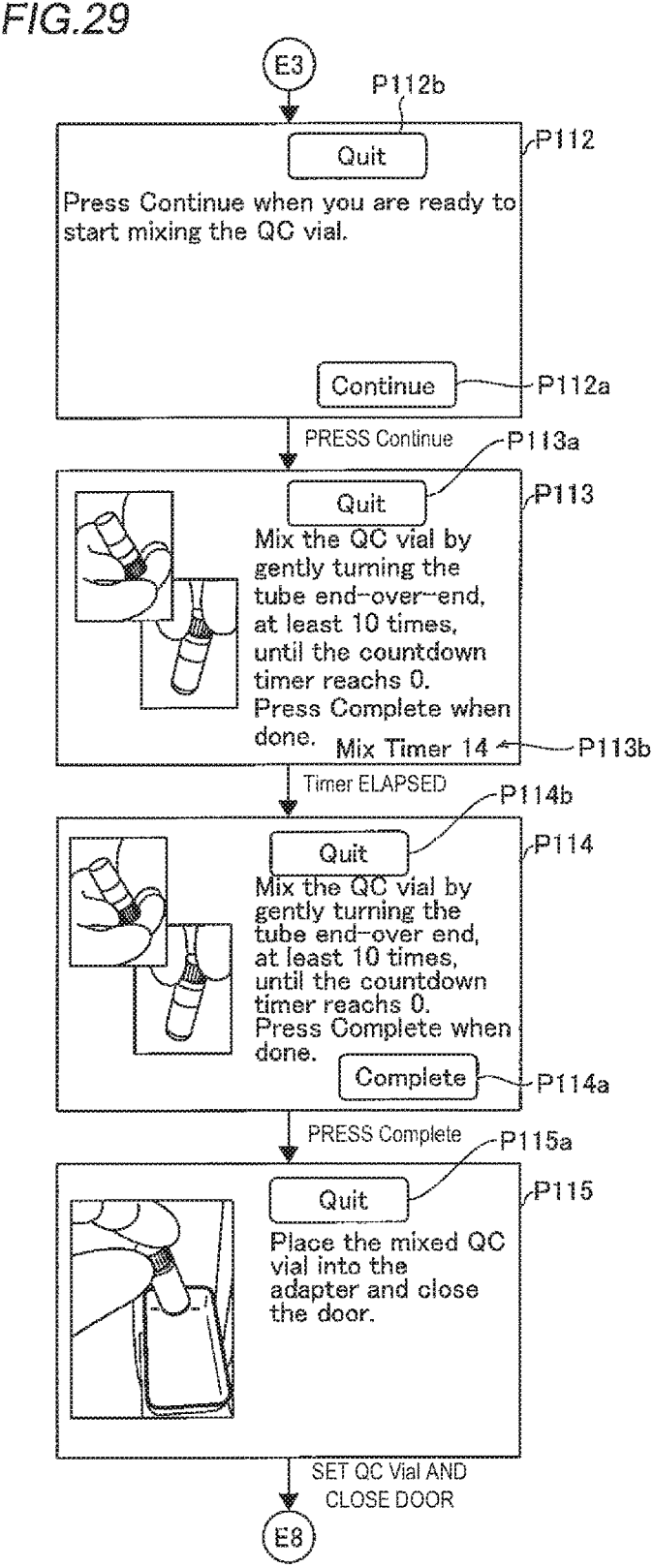
FIG. 29 is a diagram illustrating display example 4 for QC measurement.

When the validation and download of information on the QC reagent succeed, display unit 131 displays screen P112 (see FIG. 29). When the QC reagent is determined as invalid, display unit 131 displays screen P109 (see FIG. 28). When the QC reagent is determined as a scanned QC reagent, display unit 131 displays screen P111 (see FIG. 28).

As illustrated in FIG. 28, screen P109 shows a description that the QC reagent is invalid. Also, screen P109 shows Call TAC button P109a, Continue button P109b, and Quit button P109c. When Call TAC button P109a is pressed, display unit 131 displays screen P110. When Continue button P109b is pressed, display unit 131 displays screen P108 (see FIG. 27). Screen P110 shows error details. If the user telephones to the TAC and communicates the description of screen P110, he/she can receive support smoothly. Screen P110 shows Return button P110*a*. When Return button P110*a* is pressed, display unit 131 displays screen P109.

Screen P111 shows a description that the QC reagent is invalid. Also, screen P111 shows Continue button P111*a* and Quit button P111*b*. When Continue button P111*a* is pressed, display unit 131 displays screen P108 (see FIG. 27).

As illustrated in FIG. 29, screen P112 shows a description to start stirring the QC reagent, Continue button P112*a*, and Quit button P112*b*. When Continue button P112*a* is pressed, display unit 131 displays screen P113. Screen P113 shows a description to stir the QC reagent, Quit button P113*a*, and timer P113*b*. Timer P113*b* is displayed counting down from 15 sec, for example. When the time counted down by timer P113*b* has elapsed, display unit 131 displays screen P114.

Screen P114 shows Complete button P114*a* and Quit button P114*b*. When Complete button P114*a* is pressed, display unit 131 displays screen P115. Screen P115 shows a picture and an instruction on how to set the QC reagent. Also, screen P115 shows Quit button P115*a*.

Figure 30:
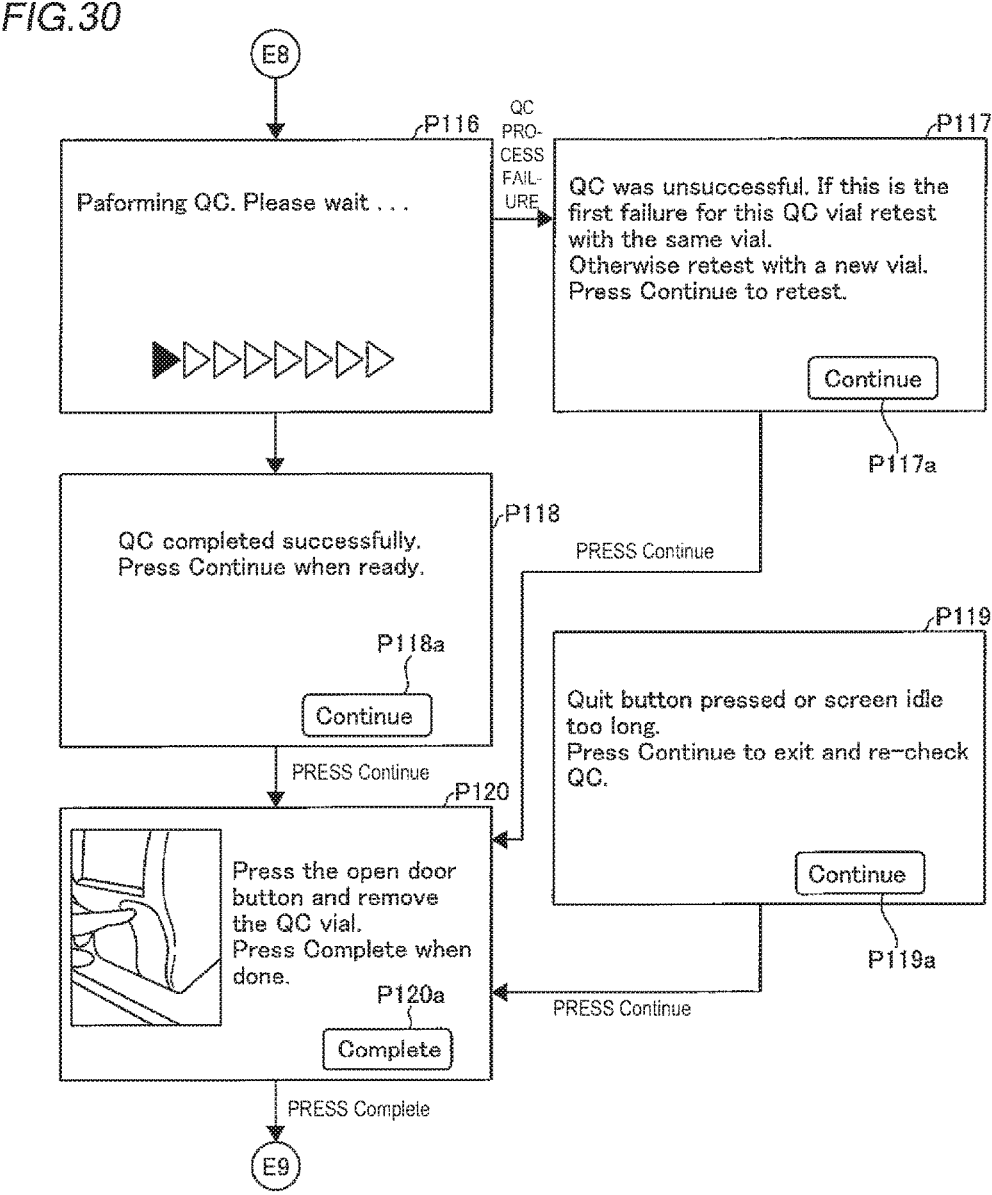
FIG. 30 is a diagram illustrating display example 5 for QC measurement.

When the QC reagent is set and the door is closed, display unit 131 displays screen P116, as illustrated in FIG. 30. Also, measurement of QC reagent is performed. When the treatment of the QC reagent fails, display unit 131 displays screen P117. Screen P117 shows a description to perform measurement again. Also, screen P117 shows Continue button P117*a*. When Continue button P117*a* is pressed, display unit 131 displays screen P120. When the measurement of the QC reagent finishes normally, display unit 131 displays screen P118. Screen P118 shows Continue button P118*a*. When Continue button P118*a* is pressed, display unit 131 displays screen P120.

Here, display unit 131 displays screen P119 when the Quit button is pressed in any of the screens, or when a predetermined time period has elapsed with the screen left unoperated. Screen P119 shows Continue button P119*a*. When Continue button P119*a* is pressed, display unit 131 displays screen P120.

Screen P120 shows a picture and an instruction on how to remove the container of the QC reagent from specimen analyzer 100. Also, screen P120 shows Complete button P120*a*. When Complete button P120*a* is pressed, display unit 131 displays screen P121 (see FIG. 31).

Figure 31:
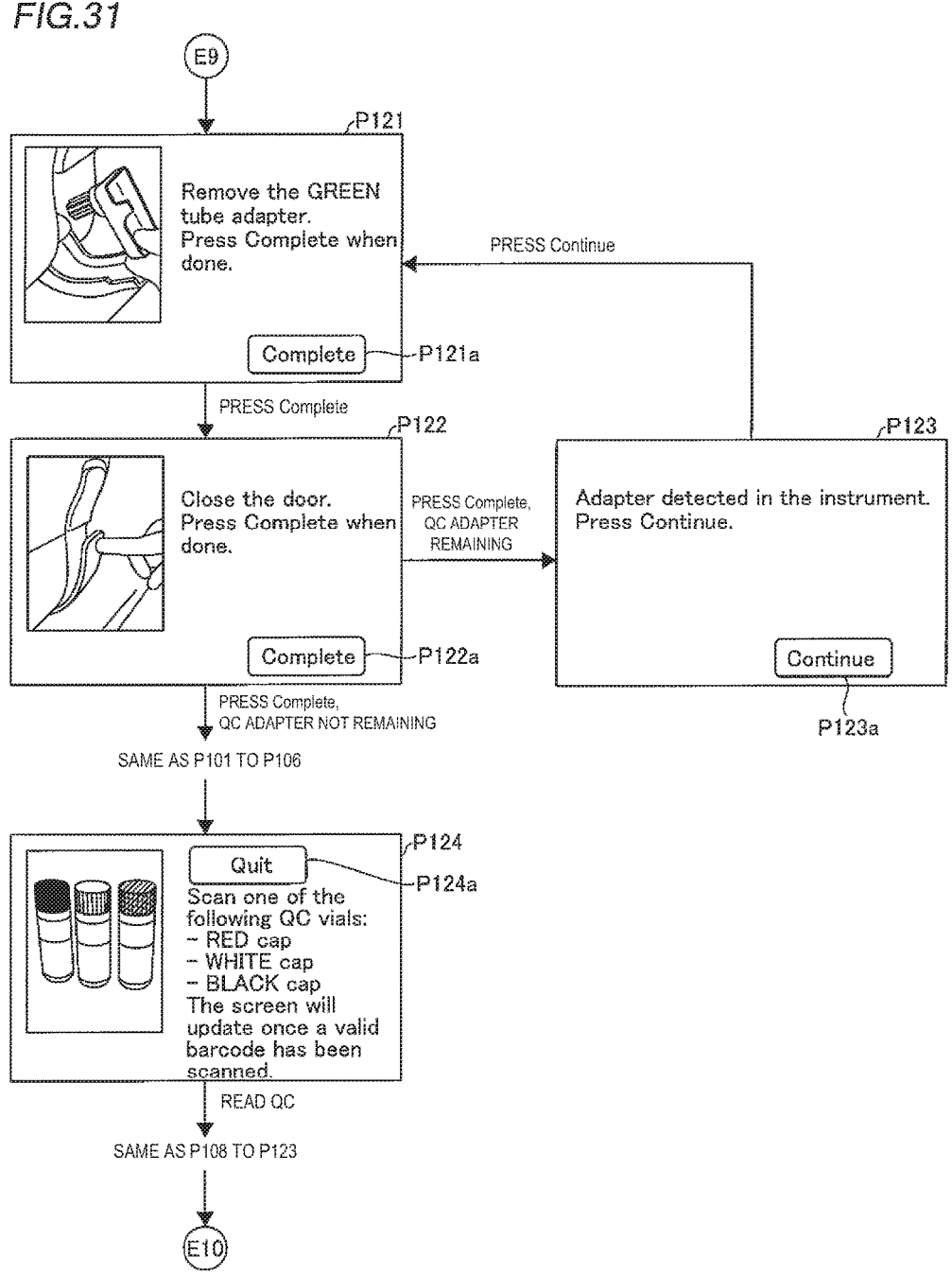
FIG. 31 is a diagram illustrating display example 6 for QC measurement.
Figure 32:
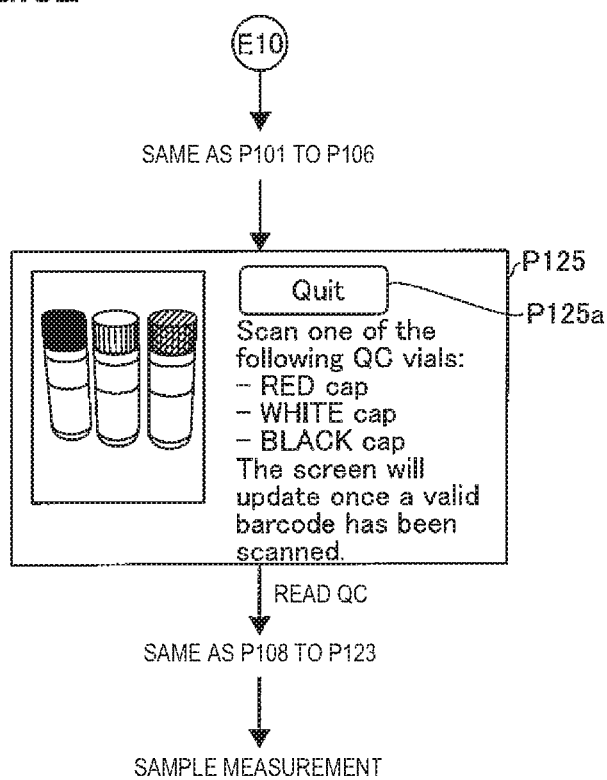
FIG. 32 is a diagram illustrating display example 7 for QC measurement.

As illustrated in FIG. 31, screen P121 shows a picture and an instruction on how to remove the adapter from specimen analyzer 100. In addition, screen P121 shows Complete button P121*a*. When Complete button P121*a* is pressed, display unit 131 displays screen P122. Screen P122 shows a picture and an instruction on how to close the door. Also, screen P122 shows Complete button P122*a*. When Complete button P122*a* is pressed, the measurement process of the High QC reagent finishes. Thereafter, a measurement process of a Low QC reagent is performed.

If the QC adapter is remaining when Complete button P122*a* is pressed, display unit 131 displays screen P123. Screen P123 shows Continue button P123*a*. When Continue button P123*a* is pressed, display unit 131 displays screen P121.

When the measurement process of the Low QC reagent starts, display unit 131 displays screens similar to screens P101 to P106, and similar processes are performed. Thereafter, display unit 131 displays screen P124. Screen P124 displays a picture and an instruction on how to read a barcode of the Low QC reagent. Also, screen P124 shows Quit button P124*a*. When the barcode of the QC reagent is read, display unit 131 displays screens similar to screen P108 to P123, and similar processes are performed. Finally, the measurement process of the Low QC reagent finishes. Thereafter, a measurement process of a Normal QC reagent is performed.

When the measurement process of the Normal QC reagent starts, display unit 131 displays screens similar to screen P101 to P106, and similar processes are performed. Thereafter, display unit 131 displays screen P125. Screen P125 displays a picture and an instruction on how to read a barcode of the Normal QC reagent. Also, screen P125 shows Quit button P125*a*. When the barcode of the QC reagent is read, display unit 131 displays screens similar to screen P108 to P123, and similar processes are performed. Finally, the measurement process of the Normal QC reagent finishes. Then, the screen of QC measurement stops being displayed. Subsequently, the screen proceeds to a screen of sample measurement. Thus, the preparation for sample measurement is done.

(Display Example at Sample Measurement)

With reference to FIG. 33 to FIG. 40, display example at sample measurement is described.

Figure 33:
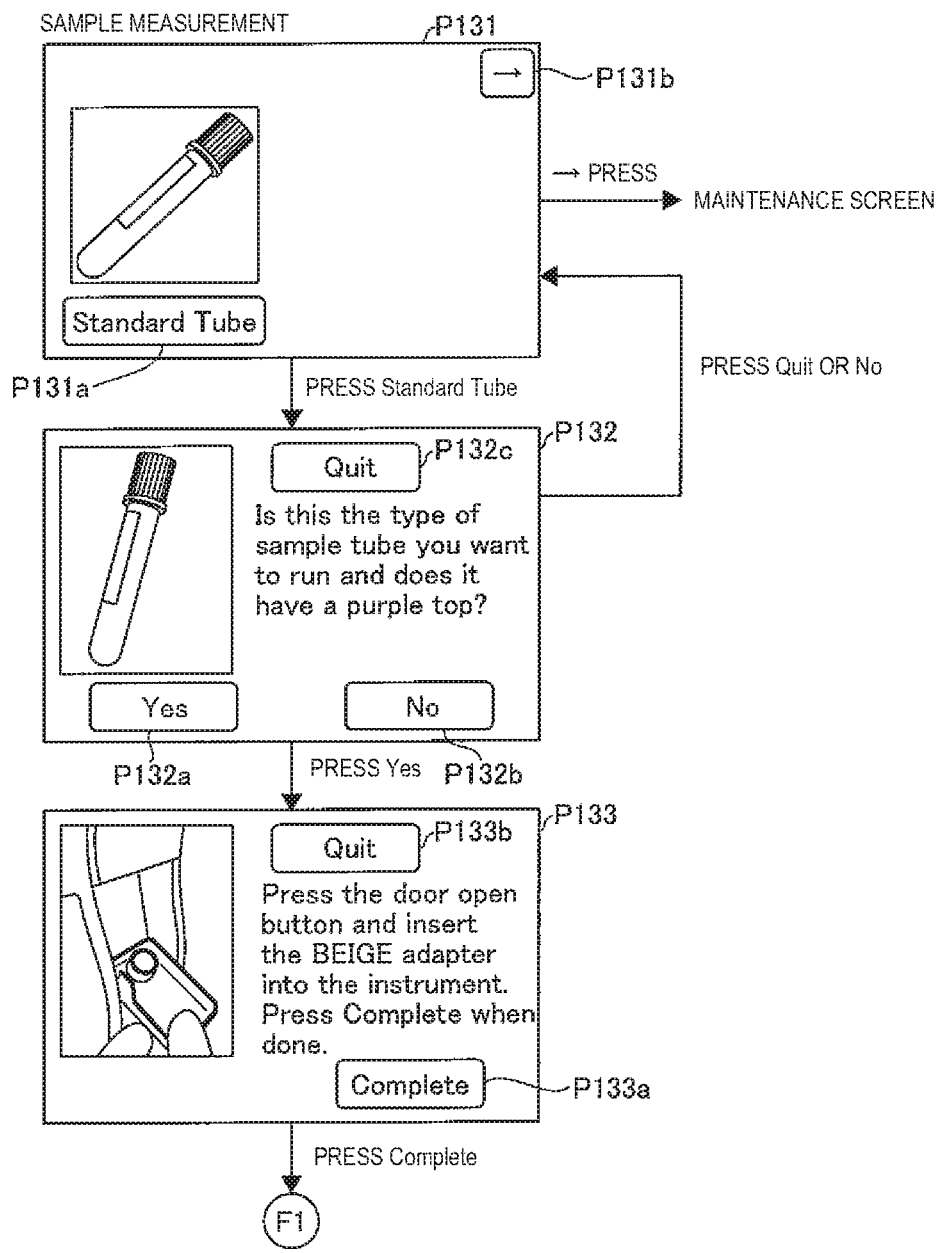
FIG. 33 is a diagram illustrating display example 1 for sample measurement.

As illustrated in FIG. 33, display unit 131 displays screen P131 for measuring the sample of the patient as the specimen. In the case of waiting for preparation of sample measurement, display unit 131 displays screen P131. Screen P131 shows Standard Tube button P131*a* and arrow button P131*b*. When arrow button P131*b* is pressed, display unit 131 displays screen P160 for maintenance (see FIG. 41). When Standard Tube button P131*a* is pressed, display unit 131 displays screen P132. Screen P132 shows a question asking whether or not the sample container is correct, Yes button P132*a* and No button P132*b*, and Quit button P132*c*. When No button P132*b* or Quit button P132*c* is pressed, display unit 131 displays screen P131. When Yes button P132*a* is pressed, display unit 131 displays screen P133.

Screen P133 shows a picture and an instruction on how to open the door and insert the adapter. Also, screen P133 shows Complete button P133*a* and Quit button P133*b*. When Complete button P133*a* is pressed, display unit 131 displays screen P134 (see FIG. 34).

Figure 34:
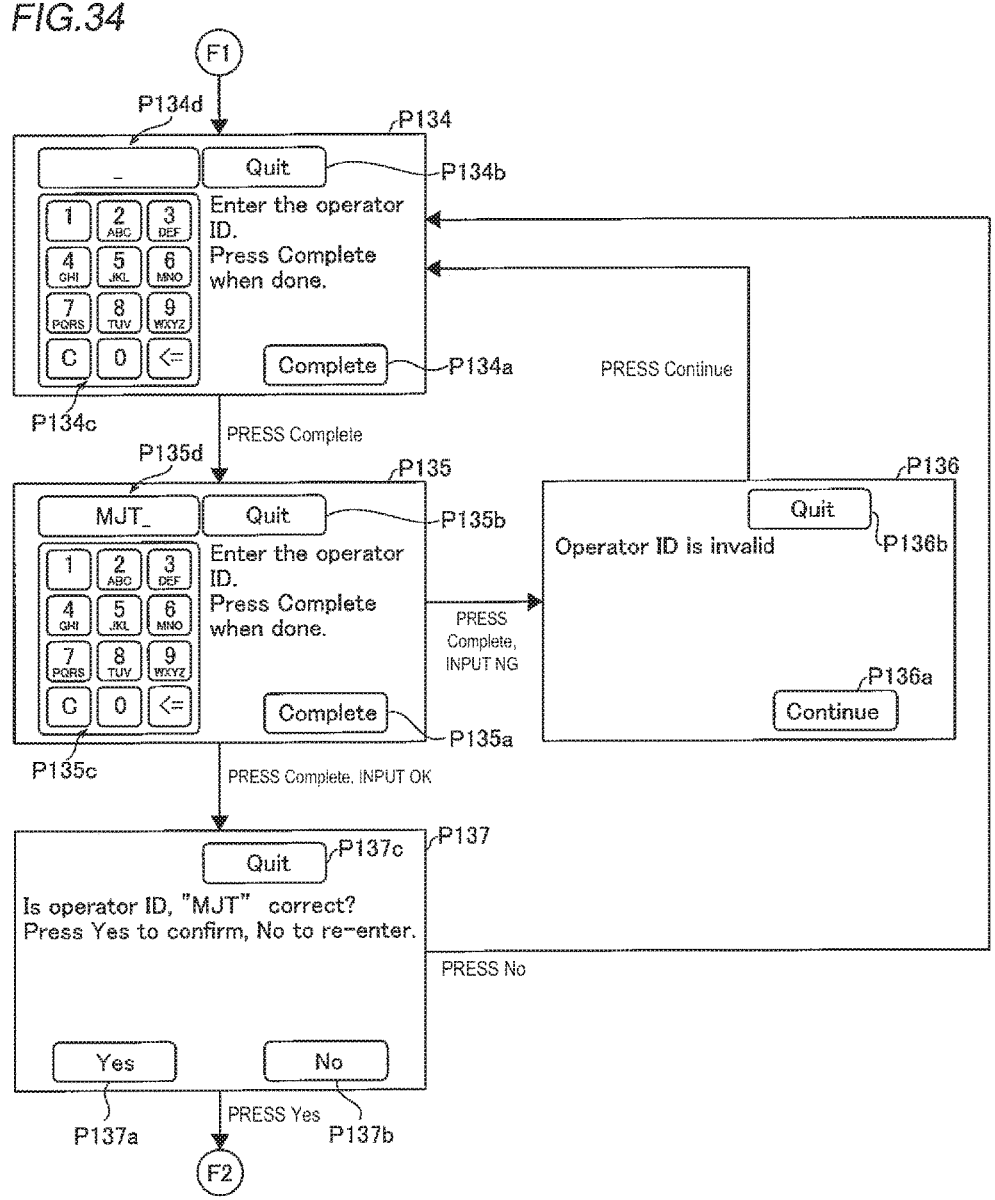
FIG. 34 is a diagram illustrating display example 2 for sample measurement.

As illustrated in FIG. 34, screen P134 shows a description for inputting the ID of the operator. Also, screen P134 shows Complete button P134*a*, Quit button P134*b*, input buttons P134*c*, and input region P134*d*. When input buttons P134*c* are operated, input region P134*d* displays inputted characters. The ID of the operator can be set using, for example, any one to three alphabetical letters.

When Complete button P134*a* is pressed, display unit 131 displays screen P135. In the example of FIG. 34, the string "MJT" is inputted as the ID of the operator. Screen P135 shows Complete button P135*a*, Quit button P135*b*, input buttons P135*c*, and input region P135*d*. When Complete button P135*a* is pressed and the input is OK, display unit 131 displays screen P137. When Complete button P135*a* is pressed but the input is NG, display unit 131 displays screen P136.

Screen P136 shows a description that the operator ID is invalid, Continue button P136*a*, and Quit button P136*b*. When Continue button P136*a* is pressed, display unit 131 displays screen P134.

Screen P137 shows a question asking whether or not the operator ID is correct, Yes button P137*a* and No button P137*b*, and Quit button P137*c*. When No button P137*b* is pressed, display unit 131 displays screen P134. When Yes button P137*a* is pressed, display unit 131 displays screen P138 (see FIG. 35).

Figure 35:
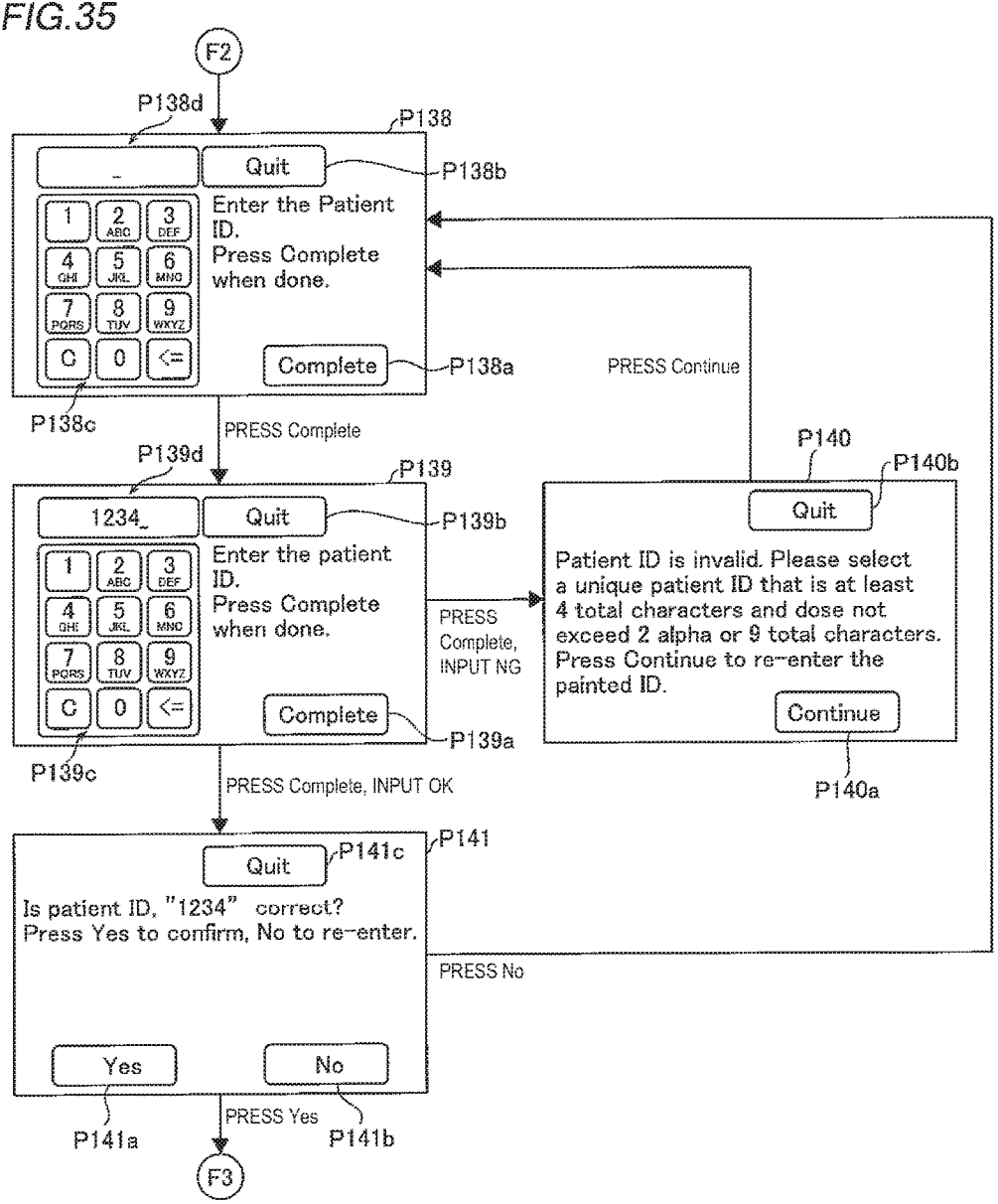
FIG. 35 is a diagram illustrating display example 3 for sample measurement.

As illustrated in FIG. 35, screen P138 shows a description for inputting the ID of the operator. Also, screen P138 shows Complete button P138a, Quit button P138b, input buttons P138c, and input region P138d. When input buttons P138c are operated, input region P138d displays inputted characters. The ID of the patient can be set using, for example, any four or more characters. The ID of the patient can be set using four to nine characters. Also, the ID of the patient can include zero to two alphabetical letters. In addition, the ID of the patient can include numbers from zero to eight characters.

When Complete button P138a is pressed, display unit 131 displays screen P139. In the example of FIG. 35, the string "1234" is inputted as the ID of the patient. Screen P139 shows Complete button P139a, Quit button P139b, input buttons P139c, and input region P139d. When Complete button P139a is pressed and the input is OK, display unit 131 displays screen P141. When Complete button P139a is pressed but the input is NG, display unit 131 displays screen P140.

Screen P140 shows a description that the patient ID is invalid, Continue button P140a, and Quit button P140b. When Continue button P140a is pressed, display unit 131 displays screen P138.

Screen P141 shows a question asking whether or not patient ID is correct, Yes button P141a and No button P141b, and Quit button P141c. When No button P141b is pressed, display unit 131 displays screen P138. When Yes button P141a is pressed, display unit 131 displays screen P142 (see FIG. 36).

Figure 36:
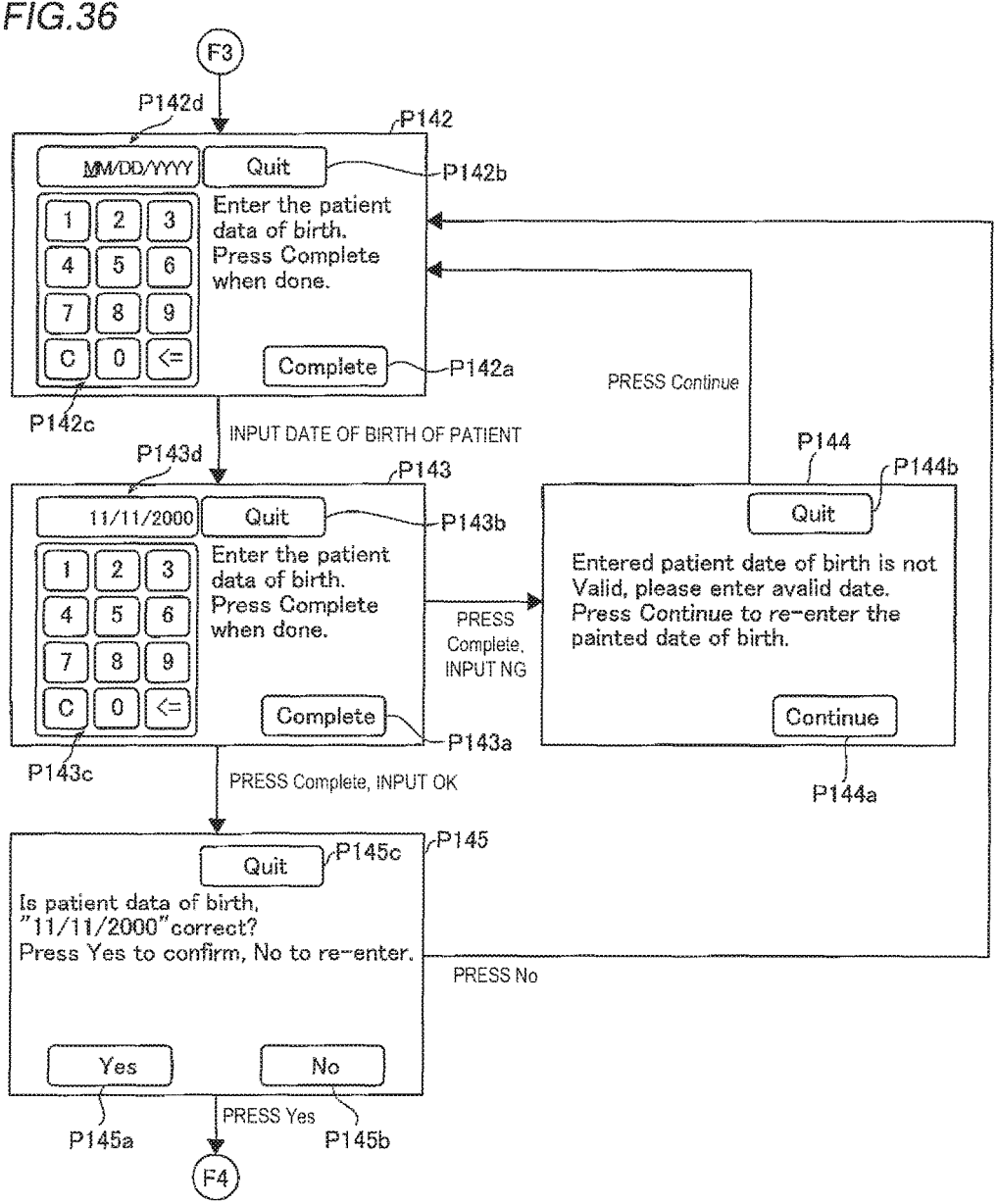
FIG. 36 is a diagram illustrating display example 4 for sample measurement.

As illustrated in FIG. 36, screen P142 shows a description for inputting the date of birth of the patient. Also, screen P142 shows Complete button P142a, Quit button P142b, input buttons P142c, and input region P142d. When input buttons P142c are operated, input region P142d displays inputted characters.

When Complete button P142a is pressed, display unit 131 displays screen P143. In the example of FIG. 36, "Nov. 11, 2000" is inputted as the date of birth of the patient. Screen P143 shows Complete button P143a, Quit button P143b, input buttons P143c, and input region P143d. When the Complete button P143a is pressed and the input is OK, display unit 131 displays screen P145. When Complete button P143a is pressed but the input is NG, display unit 131 displays screen P144.

Screen P144 shows a description that the date of birth of the patient is invalid, Continue button P144a, and Quit button P144b. When Continue button P144a is pressed, display unit 131 displays screen P142.

Screen P145 shows a question asking whether or not the date of birth of the patient is correct, Yes button P145a and No button P145b, and Quit button P145c. When No button P145b is pressed, display unit 131 displays screen P142. When Yes button P145a is pressed, display unit 131 displays screen P146 (see FIG. 37).

Figure 37:
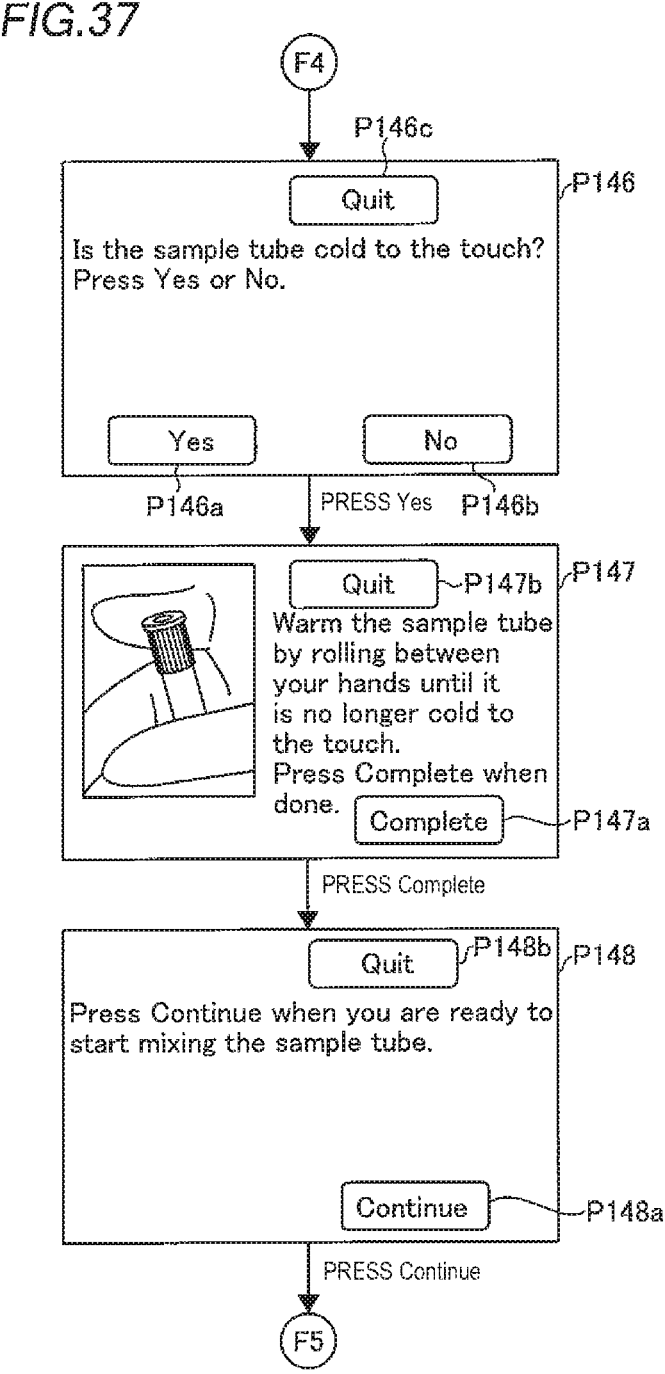
FIG. 37 is a diagram illustrating display example 5 for sample measurement.

As illustrated in FIG. 37, screen P146 shows a question asking whether or not the sample container is cold, Yes button P146a and No button P146b, and Quit button P146c. When Yes button P146a is pressed, display unit 131 displays screen P147. Screen P147 shows a picture and an instruction on how to warm the sample container. Also, screen P147 shows Complete button P147a and Quit button P147b. When Complete button P147a is pressed, display unit 131 displays screen P148.

Screen P148 shows a description to start stirring the sample, Continue button P148a, and Quit button P148b. When Continue button P148a is pressed, display unit 131 displays screen P149 (see FIG. 38).

Figure 38:
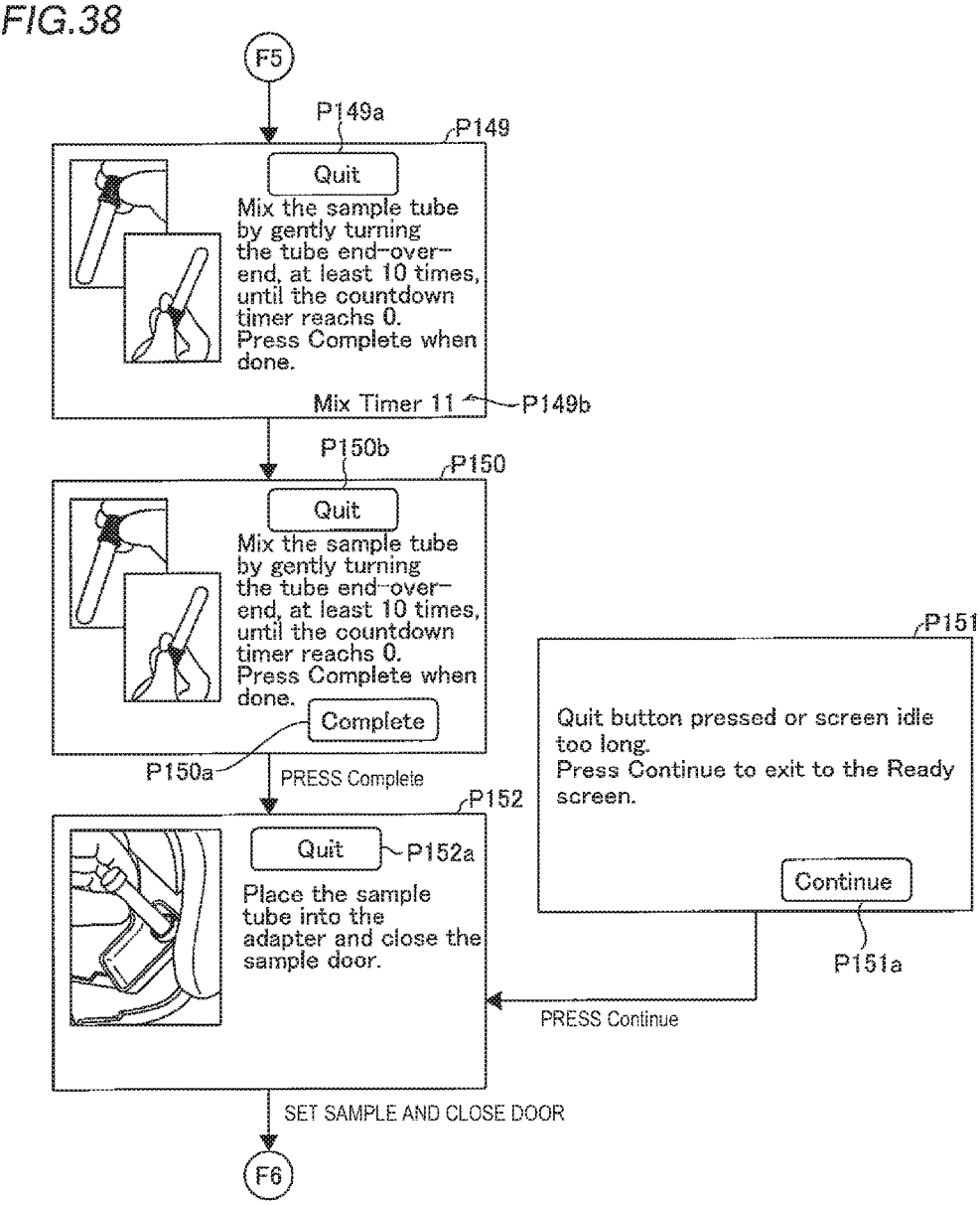
FIG. 38 is a diagram illustrating display example 6 for sample measurement.

As illustrated in FIG. 38, screen P149 shows a description to stir the sample, Quit button P149a, and timer P149b. Timer P149b is displayed counting down from 15 sec, for example. When the time counted down by timer P149b has elapsed, display unit 131 displays screen P150. Screen P150 shows Complete button P150a and Quit button P150b. When Complete button P150a is pressed, display unit 131 displays screen P152.

Here, display unit 131 displays screen P151 when the Quit button is pressed in any of the screens, or when a predetermined time period has elapsed with the screen left unoperated. Screen P151 shows Continue button P151a. When Continue button P151a is pressed, display unit 131 shows screen P152.

Screen P152 shows a picture and an instruction on how to set the sample container. Also, screen P152 shows Quit button P152a.

Figure 39:
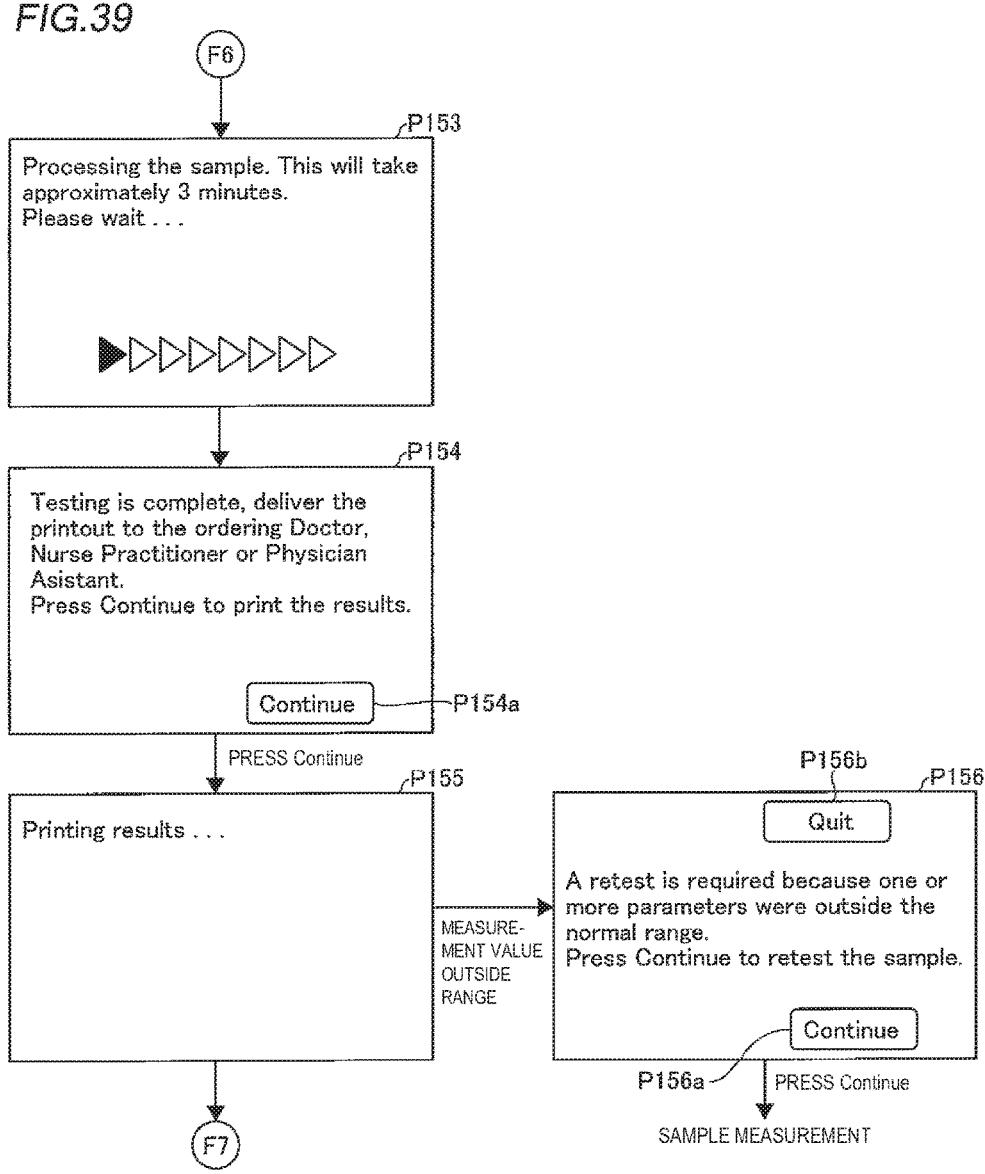
FIG. 39 is a diagram illustrating display example 7 for sample measurement.

When the sample container is set and the door is closed, display unit 131 displays screen P153, as illustrated in FIG. 39. Also, measurement of sample is performed. When the measurement of the sample finishes, display unit 131 displays screen P154. Screen P154 shows a description for printing and Continue button P154a. When Continue button P154a is pressed, display unit 131 displays screen P155.

Screen P155 shows a description that the printing is in progress. Also, print unit 135 prints the results. If one or more of the measurement results are outside normal range, display unit 131 displays screen P156. Screen P156 shows a description to perform measurement again, Continue button P156a, and Quit button P156b. When Continue button P156a is pressed, display unit 131 displays first screen P131 of sample measurement (see FIG. 33).

Figure 40:
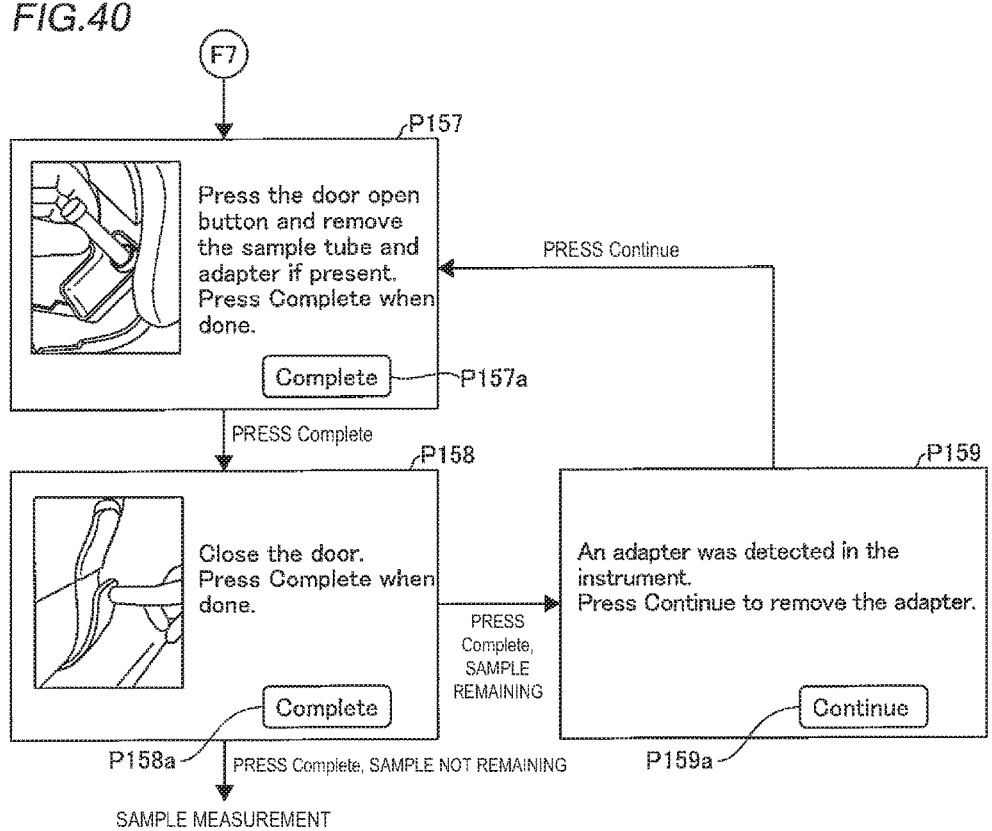
FIG. 40 is a diagram illustrating display example 8 for sample measurement.

As illustrated in FIG. 40, screen P157 shows a picture and an instruction on how to remove the sample container from specimen analyzer 100. Also, screen P157 shows Complete button P157a. When Complete button P157a is pressed, display unit 131 displays screen P158. Screen P158 shows a picture and an instruction on how to close the door. Also, screen P158 shows Complete button P158a. When Complete button P158a is pressed, the sample measurement process finishes. Thereafter, display unit 131 displays first screen P131 of sample measurement (see FIG. 33).

If the adapter is remaining when Complete button P158a is pressed, display unit 131 displays screen P159. Screen P159 shows Continue button P159a. When Continue button P159a is pressed, display unit 131 displays screen P157.

In the example of FIG. 39, controller 140 performs control of causing print unit 135 to print analysis results 102 of analysis unit 120, and causing display unit 131 to display a notification message indicating that printed sheet 300, on which analysis results 102 has been printed, is to be outputted. To be more specific, in screen P154 of FIG. 39, controller 140 displays a message to print analysis results 102 when Continue button P154a is pressed. Also, in screen P155, controller 140 displays a notification message indicating that printed sheet 300 is being outputted.

In addition, in the example of FIG. 39, display unit 131 displays print operation screen (see screen P154) for starting of the printing of analysis results 102.

In print operation screen P154, display unit 131 displays operational guidance and instructions to deal with printed sheet 300 after printing. Thus, prior to operation, print operation screen P154 shows not only a description on the operation by the user in the case where print operation screen P154 is displayed, but also instructions to deal with printed sheet 300 after the printing is started. There is possibility that the user may not take a look at the display screen after he/she performs operation in accordance with print operation screen P154. For this reason, the above configuration makes sure that the user recognizes the instructions relating to printed sheet 300 before the printing is started. As a result, it is possible to more reliably communicate analysis results 102 to the ordering doctor or the like even if the user is unaccustomed to dealing with specimen analyzer 100.

The instructions to deal with the printed sheet include a message instructing to deliver the printed sheet to the ordering doctor. Thus, prior to outputting printed sheet 300, a message is displayed instructing to deliver printed sheet 300 to the ordering doctor. For this reason, it is possible to more reliably communicate analysis results 102 to the ordering doctor or the like even if the user is unaccustomed to dealing with specimen analyzer 100. As an explanation for the printing, screen P154 shows an example of operational guidance teaching to input Continue button P154a, and of delivering the printed sheet to the ordering doctor or the like.

In the first embodiment, controller 140 causes display unit 131 to automatically display print operation screen P154 for starting of the printing of analysis results 102 when analysis unit 120 finishes analyzing specimen 101, and causes print unit 135 to start the printing of analysis results 102 depending on the operations in accordance with print operation screen P154. Print unit 135 starts the printing of analysis results 102 based on the operations in accordance with print operation screen P154 (see screen P155). To be more specific, print unit 135 starts the printing of analysis results 102 based on the input of Continue button P154a. Thus, print unit 135 prints analysis results 102 on print sheet 136. Although the size of the display screen displayable at one time by display unit 30 is limited, the print area of print unit 135 can be adjusted as desired by, for example, changing the size of the print sheet. Thus, it is possible to print analysis results 102 without making the font size small. When print unit 135 starts the printing of analysis results 102 depending on the operations in accordance with print operation screen P154, the user is allowed to recognize that analysis results 102 are outputted as printed sheet 300. As a result, it is possible to prevent erroneous recognition of analysis results 102 attributed to low visibility and overlooking of analysis results 102 by the user, even in the case of a small display screen. Moreover, by printing analysis results 102, the operator can hand in printed sheet 300 to the ordering doctor or the like without any modifications. Thus, miscommunication of analysis results 102 to the ordering doctor can be prevented.

Furthermore, in the example of FIG. 39 and FIG. 40, controller 140 performs control to disable analysis unit 120 from analyzing next specimen 101 until print unit 135 completes printing of analysis results 102. To be more specific, the analysis operation for next specimen 101 is not started unless the user performs operations in accordance with print operation screen P154 and printed sheet 300 is outputted along with screen P155. Thus, since analysis results 102 are reliably printed each time an analysis is performed, it is possible not only to prevent overlooking of analysis results 102, but also to prevent wrong taking of analysis results 102 in the case of performing analysis more than one time.

In addition, if analysis results 102 include an abnormal value, controller 140 causes display unit 131 to display an abnormal value notification screen (see screen P156) to communicate that an abnormal value is included. When abnormal value notification screen P156 is displayed, analysis unit 120 is capable of retesting same specimen 101 only when an operation is performed in accordance with abnormal value notification screen P156. Thus, it is possible for the user to retest same specimen 101 as a recommended action if there is an abnormal value which requires attention during diagnosis based on analysis results 102. Since retest is not started unless operations are performed in accordance with abnormal value notification screen P156, it is possible for the user, unaccustomed to dealing with specimen analyzer 100, to more reliably recognize the necessity of retest.

If analysis results 102 include an abnormal value, controller 140 prohibits print unit 135 from printing analysis results 102, and causes abnormal value notification screen P156 to show a message prompting to perform retesting. The example of screen P156 shows a message communicating it is necessary to retest because one or more analysis results 102 are outside normal range. Thus, the fact that analysis results 102 are not printed and the message prompting to perform retest make it possible for the user, unaccustomed to dealing with specimen analyzer 100, to strongly recognize the necessity of retest. In addition, since analysis results 102 including an abnormal value are not printed, it is possible to prevent wrong treatment based on the abnormal value.

In the example of screen P156, when Continue button 156a is inputted, a series of processes for performing retest are executed. Here, by inputting Quit button 156b, analysis of another specimen 101 can be started.

(Display Example at Maintenance)

With reference to FIG. 41 to FIG. 48, a display example at maintenance is described.

Figure 41:
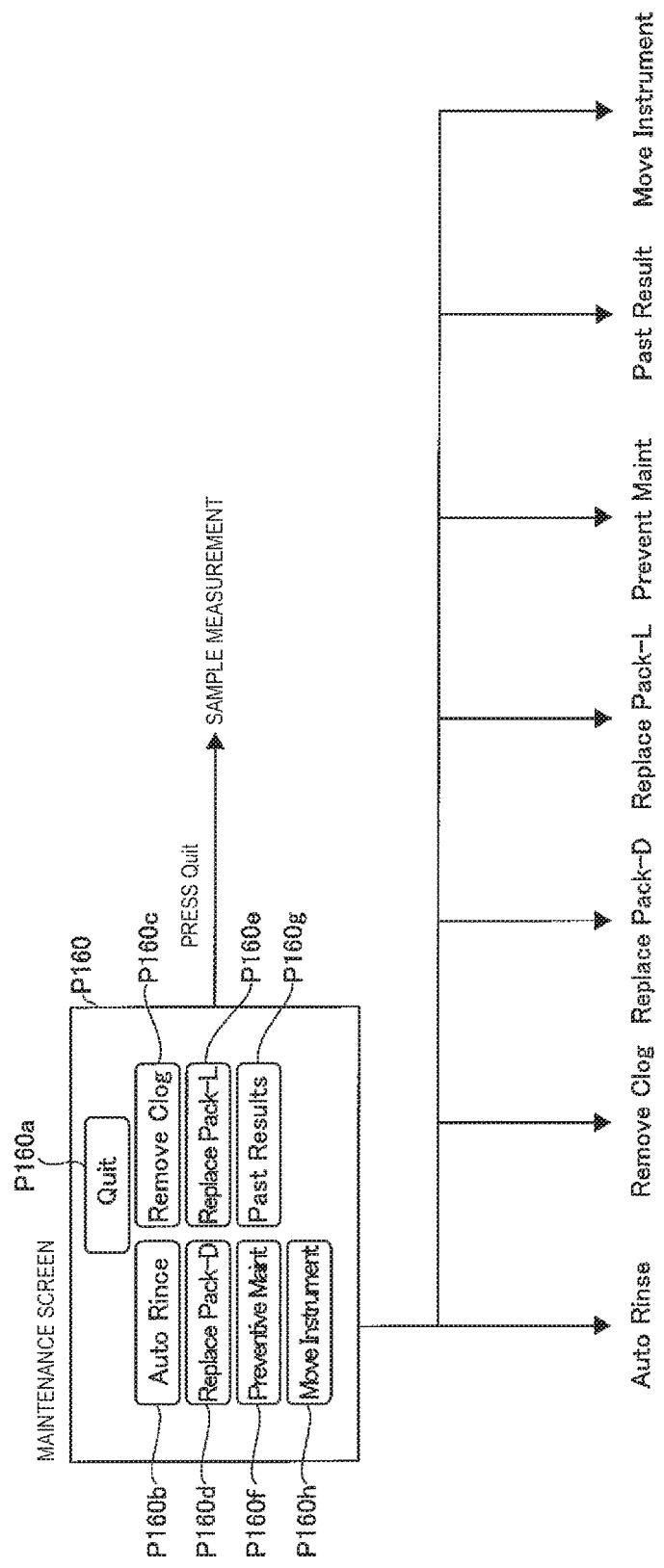
FIG. 41 is a diagram illustrating display example 1 for maintenance.

As illustrated in FIG. 41, screen P160 shows a screen for performing maintenance. To be more specific, screen P160 Quit button P160a, Auto Rince button P160b, Remove Clog button P160c, Replace Pack-D button P160d, Replace Pack-L button P160e, Preventive Maint button P160f, Past Results button P160g, and Move Instrument button P160h.

Figure 42:
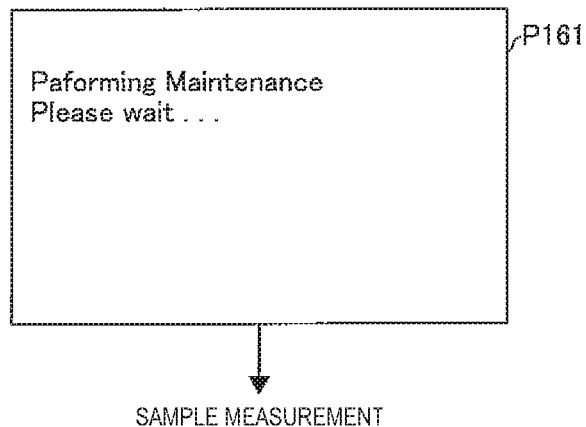
FIG. 42 is a diagram illustrating display example 2 for maintenance.

When Auto Rince button P160b is pressed, display unit 131 displays screen P161, as illustrated in FIG. 42. Also, a cleaning process with use of a diluted solution is performed. Thereafter, display unit 131 displays first screen P131 of sample measurement (see FIG. 33).

Figure 43:
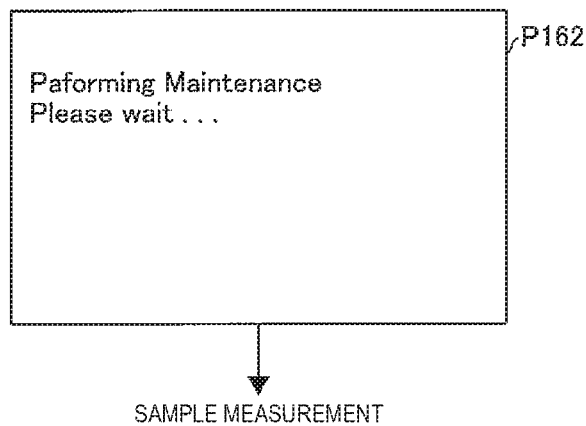
FIG. 43 is a diagram illustrating display example 3 for maintenance.

When Remove Clog button P160c is pressed, display unit 131 displays screen P162, as illustrated in FIG. 43. Also, a process of removing the clog of detector 123 is performed.

Figure 44:
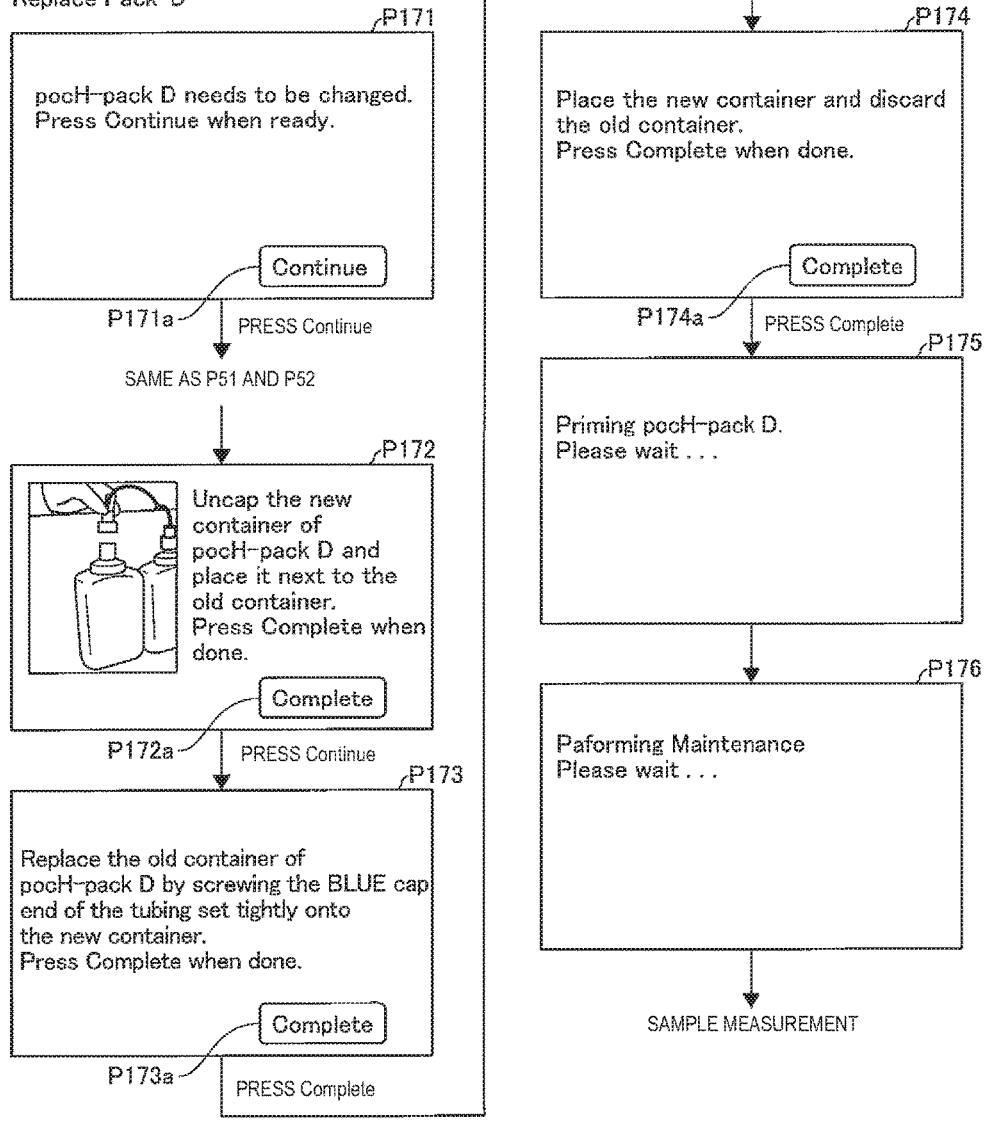
FIG. 44 is a diagram illustrating display example 4 for maintenance.

When Replace Pack-D button P160d is pressed, display unit 131 displays screen P171, as illustrated in FIG. 44. In addition, display unit 131 displays screen P171 also in the case where it is determined that the diluted solution has been used up. Screen P171 displays Continue button P171a. When Continue button P171a is pressed, display unit 131 displays screens similar to screens P51 and P52, and similar processes are performed. Thereafter, display unit 131 displays screen P172.

Screen P172 shows a picture and an instruction on how to place the reagent container. Also, screen P172 shows Complete button P172a. When Complete button P172a is pressed, display unit 131 displays screen P173. Screen P173 shows a description for replacing the reagent container. Also, screen P173 shows Complete button P173a. When Complete button P173a is pressed, display unit 131 displays screen P174.

Screen P174 shows a description to place and dispose of the reagent container. Also, screen P174 shows Complete button P174a. When Complete button P174a is pressed, display unit 131 displays screen P175. Also, the diluted solution is fed to specimen analyzer 100. Thereafter, display unit 131 displays screen P176. After that, display unit 131 displays first screen P131 of sample measurement (see FIG. 33).

Figure 45:
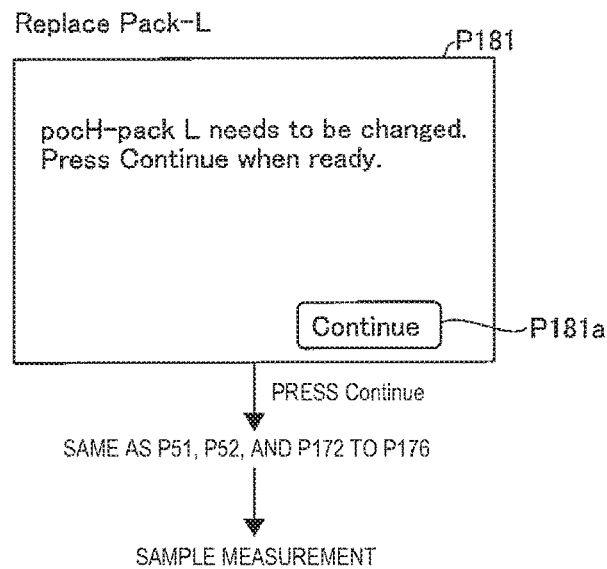
FIG. 45 is a diagram illustrating display example 5 for maintenance.

When Replace Pack-L button P160e is pressed, display unit 131 displays screen P181, as illustrated in FIG. 45. In addition, display unit 131 displays screen P181 also in the case where it is determined that the hemolyzer has been used up. Screen P181 displays Continue button P181a. When Continue button P181a is pressed, display unit 131 displays screens similar to screens P51, P52, and P172 to P176, and similar processes are performed. Thereafter, display unit 131 displays first screen P131 of sample measurement (see FIG. 33).

Figure 46:
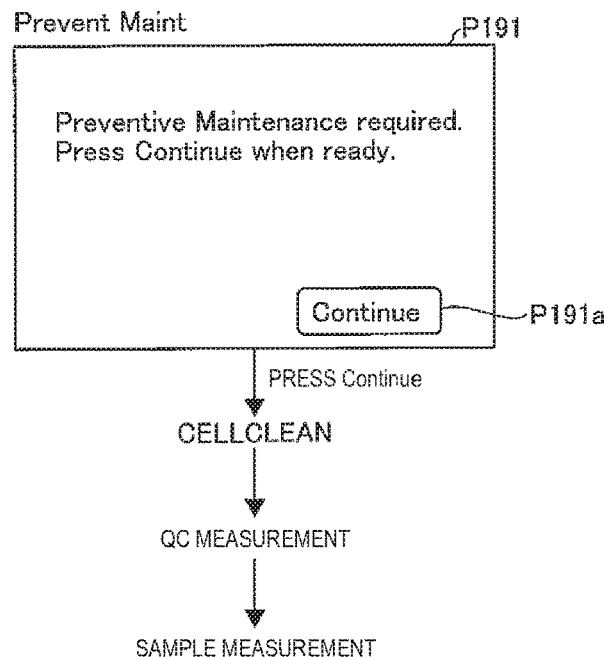
FIG. 46 is a diagram illustrating display example 6 for maintenance.

When Preventive Maint button P160f is pressed, display unit 131 displays screen P191, as illustrated in FIG. 46. Also, display unit 131 displays screen P191 when cleaning by CELLCLEAN is needed. Screen P191 shows Continue button P191a. When Continue button P191a is pressed, a process similar to the cleaning by CELLCLEAN is performed. Thereafter, a process similar to the QC measurement is performed, and display unit 131 displays first screen P131 of sample measurement (see FIG. 33).

Figure 47:
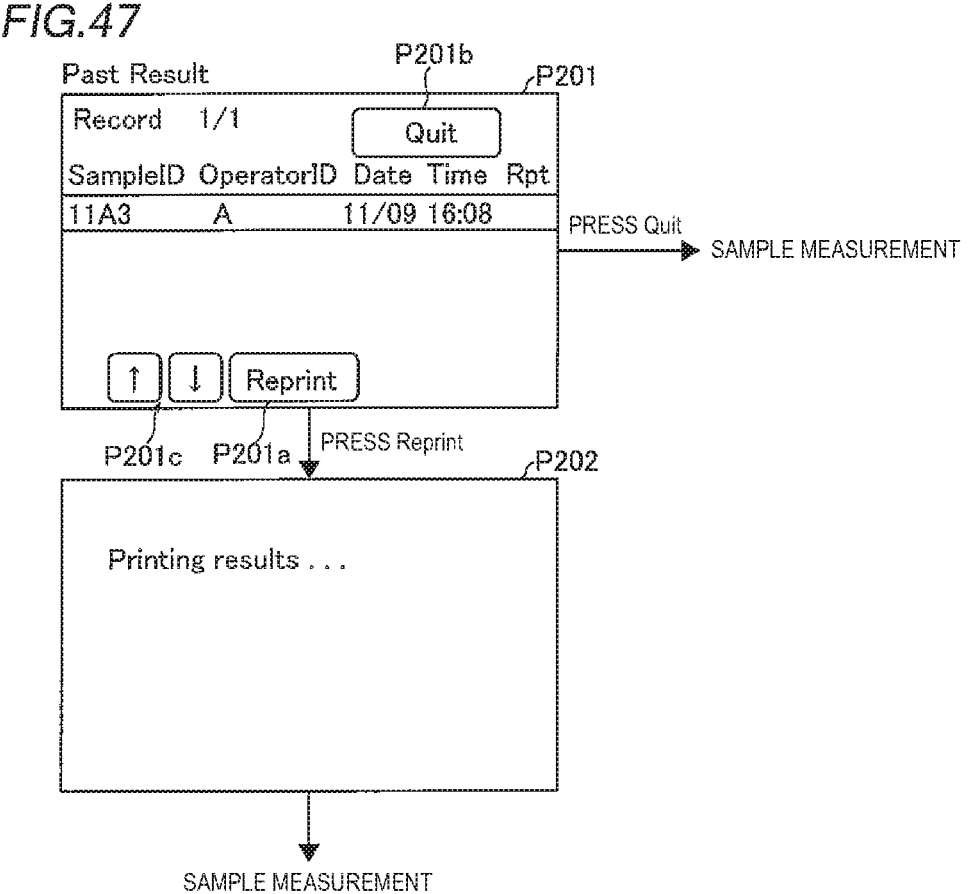
FIG. 47 is a diagram illustrating display example 7 for maintenance.

When Past Results button P160g is pressed, display unit 131 displays screen P201, as illustrated in FIG. 47. Screen P201 shows Reprint button P201a, Quit button P201b, and select button P201c. When select button P201c is used to select a past measurement and Reprint button P201a is pressed, past measurement results are printed. By pressing Reprint button 201a, display unit 131 displays screen P202. Then, print unit 135 prints the measurement results. Thereafter, display unit 131 displays first screen P131 of sample measurement (see FIG. 33).

Figure 48:
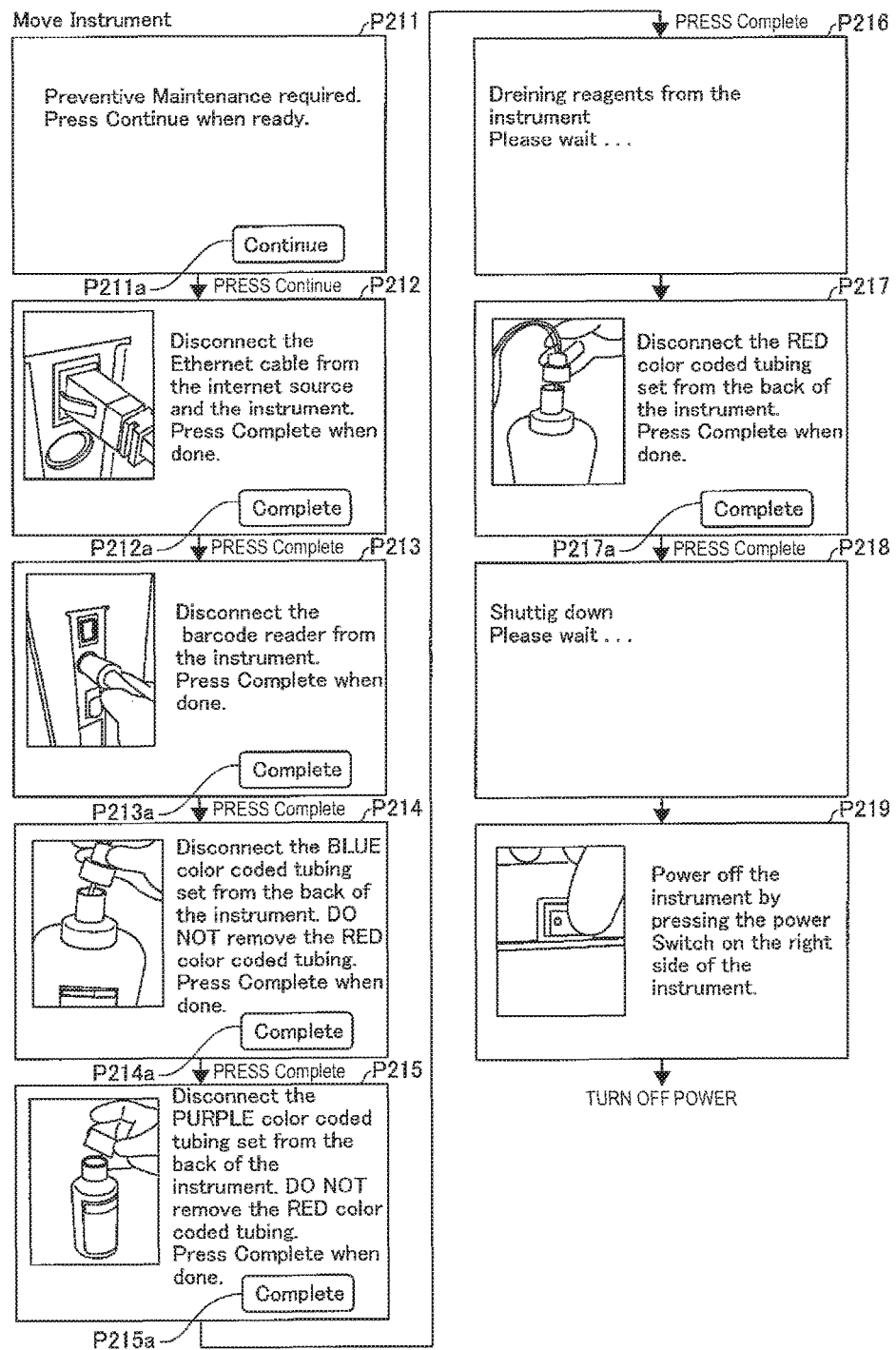
FIG. 48 is a diagram illustrating display example 8 for maintenance.

When Move Instrument button P160h is pressed, display unit 131 displays screen P211, as illustrated in FIG. 48. Screen P211 shows Continue button P211a. When Continue button P211a is pressed, display unit 131 displays screen P212. Screen P212 shows a picture and an instruction on how to remove the Ethernet cable from specimen analyzer 100. Also, screen P212 shows Complete button P212a. When Complete button P212a is pressed, display unit 131 displays screen P213.

Screen P213 shows a picture and an instruction on how to remove the barcode reader from specimen analyzer 100. Also, screen P213 shows Complete button P213a. When Complete button P213a is pressed, display unit 131 displays screen P214. Screen P214 shows a picture and an instruction on how to remove the container of the diluted solution from the tube. Also, screen P214 shows Complete button P214a. When Complete button P214a is pressed, display unit 131 displays screen P215.

Screen P215 shows a picture and an instruction on how to remove the container of the hemolyzer from the tube. Also, screen P215 shows Complete button P215a. When Complete button P215a is pressed, display unit 131 displays screen P216. Screen P216 shows a description to discharge the liquid. In addition, the liquid is discharged from specimen analyzer 100. Thereafter, display unit 131 displays screen P217.

Screen P217 shows a picture and an instruction on how to remove the container of the waste liquid from the tube. Also, screen P217 shows Complete button P217a. When Complete button P217a is pressed, display unit 131 displays screen P218. Screen P218 shows a description that shutdown is in progress. Thereafter, display unit 131 displays screen P219.

Screen P219 shows a picture and an instruction on how to power off specimen analyzer 100. Thereafter, the user powers off.

(Outputting of Analysis Results)

In the example illustrated in FIG. 2, analysis unit 120 perform analysis on seventeen analysis items in total, eight measurement items plus nine analysis items, as described above. In the first embodiment, controller 140 performs control of causing print unit 135 to print analysis results 102, and prohibiting display unit 131 from displaying analysis results 102. Thus, as a result of analysis operations of specimen analyzer 100, the user obtains printed sheet 300 being print sheet 136 on which analysis results 102 are written, as illustrated in FIG. 49.

In the example of FIG. 49, printed on printed sheet 300 are facility information 301, apparatus information 302, date information 303, operator information 304, subject information 305, subject attribute information 306, result displaying section 307, message section 308, and reference value information 309. Note that although printed sheet 300 is separated for convenience in FIG. 49, the separated portions are actually connected, and printed sheet 300 is one piece of print sheet 136 on which printing has been performed.

Facility information 301 includes information on the name and the address of the facility such as a hospital where specimen analyzer 100 is installed.

Apparatus information 302 is information for identifying specimen analyzer 100 which performed analysis. Apparatus information 302 includes, for example, the model, the name, and the serial number of the apparatus.

Date information 303 is information for identifying the time point at which analysis was performed. Date information 303 includes the analysis date. In FIG. 49, date information 303 includes the analysis time in addition to the analysis date.

Operator information 304 is ID information for identifying the operator who operated specimen analyzer 100. Operator information 304 is not particularly limited, and is represented by three alphabetical letters, for example.

Subject information 305 is ID information for identifying the subject from which specimen 101 is collected. Subject information 305 is represented by a seven-digit number, for example.

Subject attribute information 306 is information on the subject from which specimen 101 is collected, and shows the characteristics and nature of the subject. Preferable as subject attribute information 306 is information useful for diagnosis based on analysis results 102. Subject attribute information 306 includes at least one of the date of birth, age, and sex, for example. It is possible to grasp the age of the subject using the date of birth. The age and the sex of the subject are important information particularly useful for diagnosis based on analysis results 102. For this reason, when printed on printed sheet 300 together with analysis results 102, these factors contribute to convenience for the user such as the ordering doctor. Subject attribute information 306 may be an age, or information on the corresponding one of the age sections. There is a case where the criteria for diagnosis based on analysis results 102 differ depending on the sex, in addition to the age. Hence, subject attribute information 306 may include sex. Furthermore, subject attribute information 306 may include body information such as the height and the weight of the subject.

Result displaying section 307 is an area where analysis results 102 are printed. Analysis results 102 include numerical information 102a. In addition, if analysis results 102 include an error, analysis results 102 include information 102b indicating the type of the abnormality. As illustrated in FIG. 49, regarding multiple analysis items, print unit 135 prints analysis results 102 for each of the analysis items. Regarding each analysis item, one line of result displaying section 307 is assigned one item. To be more specific, in each analysis item of result displaying section 307, the item name, numerical information 102a, and information 102b indicating the type of the abnormality (flag) are displayed in sequential order from left. Thus, it is possible to collectively recognize analysis results 102 of the multiple analysis items. When analysis results 102 of the multiple analysis items are printed on print sheet 136, it is possible to prevent overlooking of analysis results 102 even when there is a large amount of information.

Information 102b indicating the type of the abnormality is printed to notify the user of the type of the abnormality when one or more of analysis results 102 are outside normal range, or when there is a predetermined analysis result error. If analysis results 102 include an abnormal value, controller 140 prints information 102b indicating the type of the abnormality as analysis results 102. Determination as to whether or not the results are normal or erroneous is made based on the numerical ranges for analysis result determination. Thus, if analysis results 102 of certain specimen 101 include an abnormal value, it is possible for the operator or the ordering doctor to know there is an abnormal value using printed sheet 300 on which information 102b indicating the type of the abnormality is printed. As a result, it is possible to further improve the convenience during diagnosis based on analysis results 102.

In the example of FIG. 50, for example, as information 102b indicating the type of the abnormality, print unit 135 prints information 102b indicating the type of the abnormality if analysis results 102 includes an abnormal value. Information 102b indicating the content of the error includes information 314 indicating a first error showing that numerical information 102a is included in a first erroneous ranges 372 (see FIG. 53), and information 315 indicating a second error showing that numerical information 102a is included in a second erroneous ranges 373 (see FIG. 53). Information 314 indicating a first error can include an indicator indicating a high value (High) and an indicator indicating a low value (Low) for each of analysis results 102. Information 315 indicating a second error can include an indicator indicating an erroneously high value (ALERT H) and an indicator indicating an erroneously low value (ALERT L), for example.

If a certain abnormal value included in analysis results 102 is within a preset predetermined numerical range, controller 140 excludes the predetermined abnormal value in analysis result 102 from the content to be printed. The predetermined numerical range is, for example, second determination range 360 to be described later (see FIG. 53 to FIG. 55). Thus, if predetermined numerical range 360 is set to a numerical range of abnormal value which requires attention particularly in clinical examination, for example, it is possible to strongly prompt to perform e.g. retest when a predetermined abnormal value is obtained which requires attention in particular because the predetermined abnormal value is not provided to the ordering doctor or the like. Additionally, it is possible to avoid inappropriate treatment performed based on an abnormal value belonging to predetermined numerical range 360. An embodiment of displaying result displaying section 307 is described later.

In FIG. 49, displayed in message section 308 is a predetermined message to the user in a predetermined case. For example, if analysis results 102 include an abnormal value, controller 140 prints a predetermined message. The predetermined message includes message 311 prompting further testing. Thus, message 311 prompting further testing allows the user to propose to the patient that he/she have a detailed examination at, for example, a specialized medical facility, enabling appropriate diagnosis based on more appropriate analysis results. Moreover, it is possible to seek instructions of the ordering doctor or the like based on the message even if the operator of the apparatus does not understand the content of analysis results 102. Furthermore, the predetermined message includes, for example, message 312 recommending the user to act immediately. If analysis results 102 have no particular problem, no message is displayed in message section 308.

Here, print unit 135 prints the predetermined message on print sheet 136 below analysis results 102. This makes it possible for the user such as the ordering doctor to recognize the predetermined message by continuing to read the print content after he/she checks analysis results 102 on printed sheet 300. Thus, it is possible to prevent overlooking of not only analysis results 102 but also the predetermined message. In FIG. 49, message section 308 where the predetermined message is displayed is printed between analysis results 102 and reference value information 309. In addition, message section 308 is printed immediately below analysis results 102.

The intention of reference value information 309 is to provide information for evaluating analysis results 102 to the user. Thus, in addition to analysis results 102, print unit 135 prints reference value information 309 to evaluate analysis results 102. This makes it possible to improve convenience during diagnosis based on analysis results 102 because printed analysis results 102 and reference value information 309 can be compared on printed sheet 300. Moreover, in the case of outputting reference value information 309 in addition to analysis results 102, the amount of information increases. For this reason, there is increased possibility of overlooking because display unit 131 has to display the information in multiple screens. Hence, in the case of outputting reference value information 309 together with analysis results 102, it is particularly effective to print on print sheet 136 for the purpose of preventing overlooking of analysis results 102.

Here, analysis result 102 of each analysis item has a numerical range considered a normal range. Reference value information 309 of FIG. 49 is information on numerical ranges indicating normal ranges 371 (see FIG. 55) of analysis results 102. Thus, on printed sheet 300, reference value information 309 makes it possible to grasp whether or not analysis results 102 are normal values. Hence, it is possible to improve convenience during diagnosis based on analysis results 102.

Here, the normal range for each analysis item differs depending on subject attribute information 306 such as the age of the subject. In light of this, in FIG. 49, reference value information 309 possesses several types depending on subject attribute information 306 on the subject from which specimen 101 is collected. Print unit 135 prints: subject attribute information 306: and reference value information 309 corresponding to subject attribute information 306 out of several types of reference value information 309. This makes it possible to provide a more appropriate reference value to the user depending on subject attribute information 306. As a result, it is possible to further improve convenience during diagnosis based on analysis results 102.

As described above, in the example of FIG. 49, in addition to analysis results 102, print unit 135 prints the analysis date, operator information 304 on the operator who performed analysis, and subject attribute information 306 on the subject from which the specimen is collected. This makes it possible to facilitate managing and dealing with printed sheet 300 because information necessary to manage analysis results 102 can be printed together with analysis results 102. Moreover, in the case of outputting other information associated with analysis results 102 in addition to analysis results 102, the amount of information increases. For this reason, there is increased possibility of overlooking because display unit 131 has to display the information in multiple screens. Hence, in the case of outputting other information such as the analysis date (date information 303) together with analysis results 102, it is particularly effective to print on print sheet 136 for the purpose of preventing overlooking of analysis results 102.

The information above is printed on the same surface of a single piece of print sheet 136. To be more specific, print unit 135 prints analysis results 102, subject attribute information 306, reference value information 309, and the predetermined message on the same surface of a single piece of print sheet 136. In the example of FIG. 49, all information to be printed is printed on the same surface of a single piece of print sheet 136. This makes it possible to print subject attribute information 306 and reference value information 309 useful for diagnosis, and when necessary, predetermined messages 311 and 312, together with analysis results 102, and to collectively provide them to the ordering doctor or the like. Hence, it is possible to improve convenience during diagnosis based on analysis results 102. Moreover, it is possible to prevent overlooking of printed information by the user because printing is performed on one piece of print sheet 136 in one page even in the case of outputting subject attribute information 306, reference value information 309, and predetermined messages 311 and 312 together with analysis results 102.

(Output Rules and Display Embodiment of Analysis Results on Printed Sheet)

Subsequently, output rules and a display embodiment in result displaying section 307 of printed sheet 300 are described.

Controller 140 determines whether or not analysis results 102 can be outputted depending on numerical information 102a as analysis results 102. If numerical information 102a falls within a predetermined range, controller 140 prohibits outputting of numerical information 102a to printed sheet 300. Memory 142 of controller 140 stores data of numerical ranges for analysis result determination (see FIG. 53 to FIG. 55).

<First Determination Ranges>

As illustrated in FIG. 51, out of numerical information 102a as analysis results 102 of analysis unit 120, controller 140 performs control of prohibiting the outputting of numerical information 102a outside first determination ranges relating to reliability of analysis.

FIG. 52 illustrates an example of first determination ranges 350. First determination ranges 350 (see FIG. 52) are each a numerical range considered reliable enough for analysis itself by analysis unit 120. First determination ranges 350 are each a numerical range which surely has reproducibility, accuracy, linearity, etc. of analysis results 102 of specimen analyzer 100 within a predetermined range, and is a numerical range set as the specifications of specimen analyzer 100.

In the example of FIG. 52, first determination ranges 350 are each a linearity guarantee range for specimen analyzer 100. To be more specific, analysis unit 120 outputs analysis results proportional to the number and the concentration of the target components in specimen 101. Here, the linearity guarantee range is a range where the analysis results match the line of proportionality within a predetermined error range. In other words, the linearity guarantee range may be referred to as a measurable range for analysis unit 120. Out of the analysis items, first determination ranges 350 are set for five measurement items, WBC, RBC, HGB, HCT, and PLT, which are measured by detector 123. Regarding the measurement items, when numerical information 102a outside the numerical ranges illustrated in FIG. 52 is obtained as analysis results 102, controller 140 prohibits the outputting of numerical information 102a as a measurement error.

In the example of FIG. 51, even in the case of numerical information 102a within first determination ranges 350, controller 140 performs control of prohibiting outputting when numerical information 102a includes a predetermined abnormal value. Regarding numerical information 102a within first determination ranges 350, controller 140 prohibits outputting when the information is within second determination ranges 360 indicating a predetermined error of the specimen, and performs control of permitting outputting when the information is outside second determination ranges 360.

Figure 53:
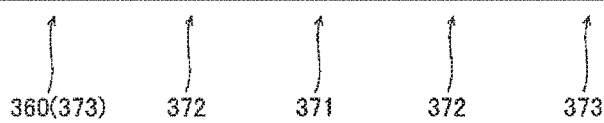
FIG. 53 is a diagram for explaining numerical ranges for evaluating analysis results for an infant.
Figure 54:
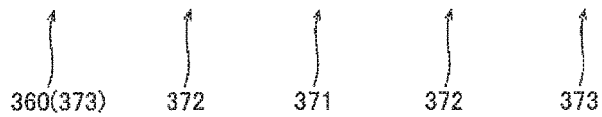
FIG. 54 is a diagram for explaining numerical ranges for evaluating analysis results for a youth.

First, regarding numerical information 102a within first determination ranges 350, analysis unit 120 performs analysis based on the numerical ranges for analysis result determination illustrated in FIG. 53 to FIG. 55. To be more specific, first determination ranges 350 include normal ranges (reference ranges) 371 indicating normal values, first erroneous ranges 372 wider than corresponding normal ranges 371, and second erroneous ranges 373 wider than first erroneous ranges 372. In the first embodiment, second determination ranges 360 are set as second erroneous ranges 373.

<Normal Range>

Controller 140 outputs analysis results 102 included in normal ranges 371 illustrated in FIG. 53 to FIG. 55. In the example of printed sheet 300 illustrated in FIG. 50, for instance, the value of MCH (29.8 [pg]) falls within the normal range of an adult (see FIG. 55), and numerical information 102a is printed as it is. If analysis results 102 are included in normal ranges 371, this means there is no error. Thus, information 102b indicating the type of the abnormality for the analysis items is not printed.

As illustrated in FIG. 53 to FIG. 55, first erroneous ranges 372 include ranges of low value (Low) and ranges of high value (High). Second erroneous ranges 373 include ranges of erroneously low value (ALERT LOW) and ranges of erroneously high value (ALERT HIGH). To be more specific, first erroneous ranges 372 are ranges indicating minor errors near normal ranges 371, and second erroneous ranges 373 are ranges indicating significant errors further deviating from first erroneous ranges 372.

<First Erroneous Range>

In the example of FIG. 51, in the initial test, controller 140 prohibits the outputting of printed sheet 300 if numerical information 102a is included in first erroneous ranges 372. To be more specific, if numerical information 102a is included in first erroneous ranges 372, controller 140 does not output printed sheet 300 but causes the user to perform retest on same specimen 101 using abnormal value notification screen P156 (see FIG. 39) for notifying that an abnormal value is included. Thus, in the initial test, all analysis results 102 are prohibited from being outputted if numerical information 102a is included in first erroneous ranges 372.

Controller 140 causes printed sheet 300 to output analysis results 102 obtained in retest. If initial analysis results 102 match retested analysis results 102, controller 140 causes print unit 135 to print analysis results 102, and if initial analysis results 102 do not match retested analysis results 102, controller 140 prohibits the printing of mismatched analysis results 102. To be more specific, if numerical information 102a of retest is included in first erroneous ranges 372 and if determination results of numerical information 102a match those of the initial test, controller 140 permits the outputting of that numerical information 102a, and outputs information indicating the type of the abnormality. For example, if numerical information 102a of the initial test is included in the range of "Low" and if numerical information 102a of retest is included in the range of "Low" as well, the controller outputs information 314 indicating a first error where numerical information 102a is included in first erroneous ranges 372, together with numerical information 102a. This makes it possible to provide analysis results 102 to the user and to cause the user to perform necessary action because analysis results 102 with an abnormal value is correct if initial analysis results 102 match retested analysis results 102. On the other hand, if initial analysis results 102 do not match retested analysis results 102, there is possibility that correct analysis results 102 cannot be obtained for a reason. Hence, it is possible to keep analysis results 102 from being provided to the user. As a result, it is possible to avoid inappropriate treatment performed based on low-reliability analysis results.

In the example of printed sheet 300 illustrated in FIG. 50, the value of MCV (81.6 [fL]) corresponds to a low value (see FIG. 55) of an adult, and "Low" information 314 indicating a first error is printed together with analysis results. Note that if the analysis result corresponds to a high value, "High" is printed as information 314 indicating a first error.

If numerical information 102a of retest is included in first erroneous ranges 372 and if determination results of numerical information 102a do not match those of the initial test, controller 140 prohibits the outputting of that numerical information 102a, and outputs information indicating the type of the abnormality. For example, if numerical information 102a of the initial test is included in the range of "Low" and if numerical information 102a of retest is included in the range of "High," the controller prohibits the outputting of numerical information 102a. In this case, as the analysis items, information 314 indicating a first error is printed.

<Second Erroneous Range>

In the example of FIG. 51, out of numerical information 102a included in second erroneous ranges 373, controller 140 prohibits the outputting of numerical information 102a within second determination ranges 360, and permits the outputting of numerical information 102a outside second determination ranges 360. If numerical information 102a is included in second erroneous ranges 373, controller 140 outputs information 102b indicating the type of the abnormality. To be more specific, as has been illustrated in FIG. 50, controller 140 displays an indicator indicating an erroneously high value (ALERT H) or an indicator indicating an erroneously low value (ALERT L) as information 315 indicating a second error where numerical information 102a is included in second erroneous ranges 373.

Second determination ranges 360 are each a range of abnormal value presenting the possibility of having a predetermined serious disease. Possible predetermined serious diseases in the blood cell counting apparatus include, for example, leukemia, aplastic anemia, myelodysplastic syndromes, paroxysmal nocturnal hemoglobinuria, systemic lupus erythematosus, malignant lymphoma, disseminated intravascular coagulation, thrombotic thrombocytopenic purpura, hypersplenism, megaloblastic anemia, sepsis, tuberculosis, sarcoidosis, hemangioma, infectious diseases, and congenital thrombocytopenia.

Each of second determination ranges 360 is set as at least part of corresponding one of second erroneous ranges 373. Each of second determination ranges 360 is set within a range satisfying corresponding one of first determination ranges 350 and within a range of predetermined erroneously low value.

In the example of FIG. 53 to FIG. 55, each of second determination ranges 360 is set within a range of erroneously low value (ALERT LOW) of corresponding one of second erroneous ranges 373 set for at least one analysis item of white blood cell count (WBC), hemoglobin concentration (HGB), hematocrit value (HCT), and platelet count (PLT). In FIG. 53 to FIG. 55, the range of erroneously low value (ALERT L) of each of white blood cell count, hemoglobin concentration, hematocrit value, and platelet count is set as corresponding one of second determination ranges 360.

Thus, if numerical information 102a is included in a range of erroneously low value (ALERT L), controller 140 prohibits the outputting of numerical information 102a. If there is numerical information 102a within second determination ranges 360, controller 140 causes output unit 130 to output information 102b indicating the type of the abnormality. To be more specific, if numerical information 102a is included in a range of erroneously low value (ALERT L), controller 140 prints information 315 indicating a second error (ALERT L) being an erroneously low value.

If numerical information 102a is included in a range of erroneously high value (ALERT H), controller 140 permits the outputting of numerical information 102a. If numerical information 102a is included in a range of erroneously high value (ALERT H), controller 140 prints information 315 indicating a second error being an erroneously high value (ALERT H).

For example, in the example of printed sheet 300 illustrated in FIG. 50, the value of HGB (24.3 [g/dL]) corresponds to an erroneously high value of an adult, and "ALERT H" information 315 indicating a second error is printed together with numerical information 102a.

On the other hand, in the example of printed sheet 300 illustrated in FIG. 50, numerical information 102a is not printed for WBC and PLT. This is because numerical information 102a of WBC and PLT falls within second determination ranges 360 (see FIG. 55). In the example of FIG. 50, "ALERT L" information 315 indicating a second error is printed for the analysis items of WBC and PLT. Thus, it is possible to know which analysis items fall within second determination ranges 360 even though numerical information 102a is not outputted.

When excluding a predetermined abnormal value from the content to be printed, controller 140 causes substitute indication 313 to be printed in place of the predetermined abnormal value. For example, controller 140 substitutes numerical information 102a within second determination ranges 360 for substitute indication 313, and causes output unit 130 to print substitute indication 313. Thus, it is possible to exclude a predetermined abnormal value from printing while causing the user to recognize that certain analysis results 102 are obtained by using substitute indication 313. Hence, the user does not misunderstand that the analysis has not been performed for a reason, unlike the case of simply excluding a predetermined abnormal value. In the example of FIG. 50, numerical information WBC and PLT within second determination ranges 360 is printed in the form of substitute indication 313 "**." Note that any display embodiment of substitute indication 313 is possible as long as it can be distinguished from numerical information 102***a*. Thus, substitute indication 313 is preferably a character other than a number, a symbol, or a plane figure, for example. If numerical information 102*a* is within second determination ranges 360, controller 140 prints information 102*b* indicating the type of the abnormality together with substitute indication 313.

As described above, if numerical information 102*a* is included in first erroneous ranges 372 or second erroneous ranges 373, controller 140 outputs information 102*b* indicating the type of the abnormality as analysis results 102. Controller 140 prohibits the outputting of numerical information 102*a* within second determination ranges 360, and permits the outputting of information 102*b* indicating the type of the abnormality.

On the other hand, if numerical information 102*a* is outside first determination ranges 350, controller 140 substitutes numerical information 102*a* outside first determination ranges 350 for substitute indication 313 and causes output unit 130 to output substitute indication 313, and prohibits the outputting of information 102*b* indicating the type of the abnormality. To be more specific, if numerical information 102*a* falls within none of normal ranges 371, first erroneous ranges 372, and second erroneous ranges 373 described above, and is outside the linearity guarantee ranges, the numerical information is substituted for substitute indication 313 on printed sheet 300. Information indicating the type of the abnormality such as information 315 or 316 is not printed.

In the example of FIG. 50, for the analysis items outside first determination ranges 350 and for the analysis items within second determination ranges 360, controller 140 prints the item names and prohibits the outputting of numerical information 102*a*. When excluding a predetermined abnormal value from the content to be printed, print unit 135 prints substitute indication 313 in place of the predetermined abnormal value.

Note that in the example of FIG. 51, the case where the outputting of numerical information 102*a* is prohibited for the analysis items other than the measurement items includes the case of a fractionation error of the analysis results. In the case of a fractionation error, controller 140 prohibits the outputting of numerical information 102*a*, and outputs information 102*b* indicating the type of the abnormality corresponding to the type of the fractionation error. Information 102*b* indicating the type of the abnormality corresponding to the type of the fractionation error includes "WBC," "RBC," "PLT," "WBC/PLT," and "WBC Diff". FIG. 50 illustrates an example where WBC Diff is displayed, and "WBC," "RBC," "PLT," and "WBC/PLT" are also displayed in the same manner.

"WBC" is printed if the number of particles of upper discriminator value or lower discriminator value is erroneously high in the particle size distribution of white blood cells. The discriminator value is a value for distinguishing the distribution of white blood cells from noise components called ghost. "RBC" is printed if the number of particles of upper discriminator value or lower discriminator value is erroneously high in the particle size distribution of red blood cells, if it is impossible to analyze red blood cell distribution width (RDW-SD and RDW-CV), or if the particle size distribution of red blood cells is bimodal. "PLT" is printed if the number of particles of upper discriminator value or lower discriminator value is erroneously high in the particle size distribution of platelets, or if it is impossible to analyze red blood cell distribution width (RDW-SD and RDW-CV). "WBC/PLT" is printed if the number of particles having a predetermined value or less is erroneously high in the particle size distribution of white blood cells. In the particle size distribution of white blood cells, "WBC Diff" is printed in any of the cases where it is impossible to fractionate into small-sized white blood cells and medium-sized white blood cells, where the discriminator value for fractionating into small-sized white blood cells and medium-sized white blood cells is high, where it is impossible to fractionate into medium-sized white blood cells and large-sized white blood cells, or where the discriminator value for fractionating into medium-sized white blood cells and large-sized white blood cells. In the cases of these fractionation errors, controller 140 substitutes numerical information 102*a* for a substitute indication.

As illustrated in FIG. 50, for each of the analysis items, controller 140 prohibits the outputting of numerical information 102*a* outside first determination ranges 350 and the outputting of numerical information 102*a* within second determination ranges 360. For this reason, in the case where numerical information 102*a* outside the linearity guarantee range is obtained or "ALERT L" numerical information 102*a* is obtained for any of the analysis items, other analysis items for which printable numerical information 102*a* is obtained are printed.

(Age Section)

FIG. 53 to FIG. 55 illustrate data examples of numerical ranges for analysis result determination, for each of the age sections. As examples of age sections, FIG. 53 illustrates an infant at the ages of two to eleven, FIG. 54 illustrates a youth at the ages of twelve to twenty, and FIG. 55 illustrates an adult at the ages of twenty one or more. The number of sections may be other than three.

In the examples of FIG. 53 to FIG. 55, out of normal ranges 371, first erroneous ranges 372, and second erroneous ranges 373, at least normal ranges 371 differ depending on the age sections. Controller 140 calculates the age of the subject from subject attribute information 306, and obtains the numerical ranges of the age section corresponding to the calculated age. Then, when numerical information 102*a* is obtained for each of the analysis items, analysis unit 120 analyzes which of normal ranges 371, first erroneous ranges 372, and second erroneous ranges 373, and second determination ranges 360 numerical information 102*a* falls within, based on the numerical ranges of the age section to which the subject belongs.

In addition, controller 140 prints normal ranges 371 of the age section to which the subject belongs on printed sheet 300 as reference value information 309. In the example of FIG. 49, it is possible to know from subject attribute information 306 (born in 1965) that the subject is an adult at the age of twenty one or more as of date information 303. Thus, FIG. 55 illustrates normal ranges 371 of the age section of an adult printed as reference value information 309. Reference value information 309 is printed for each of the analysis items. Here, in FIG. 53 to FIG. 55, the numerical ranges of "ALERT L" second determination ranges 360 are the same regardless of the age section. However, second determination ranges 360 may be different for each age section.

(Predetermined Message)

Subsequently, the predetermined message printed on printed sheet 300 is described. In the example of FIG. 49, if there is numerical information 102*a* within second determination ranges 360, controller 140 causes output unit 130 to output the predetermined message.

If numerical information 102a is within second erroneous ranges 373, controller 140 prints message 311 prompting further testing. To be more specific, if there is numerical information 102a corresponding to an erroneously high value (ALERT H) or an erroneously low value (ALERT L) within second determination ranges 360 for any of the analysis items, message 311 prompting further testing is printed. In FIG. 49, as an example, the message "RECOMMEND FURTHER TESTING" is printed.

Also, if numerical information 102a is within second erroneous ranges 373, controller 140 further prints message 312 recommending immediate action. In FIG. 49, as an example, message 312 "Potential ALERT Value should be acted upon IMMEDIATELY" is printed.

Also, numerical information 102a of all analysis items is within normal ranges 371, controller 140 does not display message 311 and message 312. Controller 140 may display a message in message section 308 based on display conditions for other messages. For example, regarding numerical information 102a of three analysis items of WBC, RBC, and HGB, if those three items are not erroneously low values (ALERT L), but if all of those three items are low values (Low), controller 140 prints message 311 prompting further testing but does not print message 312.

As described above, controller 140 controls the print content of analysis results 102. "END REPORT" printed on the end of printed information shows the end of printed sheet 300. Note that memory 142 of controller 140 stores data necessary to output analysis results 102 such as first determination ranges 350 and second determination ranges 360, information 102b indicating the type of the abnormality, and message 311 and message 312.

(Modified Example of Second Determination Range)

FIG. 53 to FIG. 55 illustrates an example where second determination ranges 360 are set to ranges of erroneously low value (ALERT L) within second erroneous ranges 373. However, all of second erroneous ranges 373 may be set to second determination ranges 360, for example. To be more specific, second determination ranges 360 may be set also to ranges of erroneously high value (ALERT H), in addition to ranges of erroneously low value (ALERT L).

FIG. 56 illustrates a printing example where both erroneously low values (ALERT L) and an erroneously high value (ALERT H) are set as second determination ranges 360. In the example of FIG. 50, numerical information 102a is printed for the HGB item corresponding to an erroneously high value (ALERT H). In the example of FIG. 56, on the other hand, the outputting of numerical information 102a is prohibited for the HGB item corresponding to an erroneously high value (ALERT H), and substitute indication 313 is printed instead of numerical information 102a. In FIG. 56, numerical information 102a corresponding to an item being an erroneously low value is substituted for substitute indication 313. "ALERT L" is assigned to an item of erroneously low value as information 315 indicating a second error, and "ALERT H" is assigned to an item of erroneously high value (ALERT H) as information 315 indicating a second error. Thus, it is possible to recognize which of an erroneously low value and erroneously high value numerical information 102a is even when the numerical information is not printed.

(Modified Example of Printing Embodiment)

The example of FIG. 50 and the example of FIG. 56 illustrate examples of substituting numerical information 102a falling within second determination ranges 360 for substitute indication 313 and printing substitute indication 313. However, the configuration may be such that numerical information 102a falling within second determination ranges 360 is not displayed, for example. The example of FIG. 57 illustrates an example where numerical information 102a falling within second determination ranges 360 is not displayed when both erroneously low values and an erroneously high value are set as second determination ranges 360. In FIG. 57, from the content to be printed, controller 140 excludes numerical information 102a falling within second determination ranges 360 together with the item names of the analysis items. Thus, information 316 indicating that the numerical information falls within second determination ranges 360 is not printed either. For this reason, in the example of FIG. 57, the analysis items themselves of WBC, HGB, and PLT with numerical information 102a falling within second determination ranges 360 have been excluded from result displaying section 307.

On the other hand, also in the example of FIG. 57, if there is numerical information 102a falling within second determination ranges 360, controller 140 prints message 311 prompting further testing in message section 308. In the example of FIG. 57, message 312 recommending immediate action is also printed. The user is allowed to recognize there is an error in analysis results 102 by message 311 prompting further testing and message 312 recommending immediate action even in the case where numerical information 102a falling within second determination ranges 360 is deleted together with the analysis items in result displaying section 307.

(Modified Example of Output Rules for Analysis Result on Printed Sheet)

The example of FIG. 51 illustrates an example where in the initial test, controller 140 prohibits the outputting of printed sheet 300 if numerical information 102a is included in first erroneous ranges 372, and performs retest. However, printed sheet 300 may be outputted in the initial test. In the initial test, if numerical information 102a is included in first erroneous ranges 372, controller 140 may substitute numerical information 102a for substitute indication 313 and output substitute indication 313, or remove numerical information 102a as a not-displayed item from the print content together with the item names of the analysis items.

FIG. 58 illustrates a modified example of output rules for analysis results 102. In a first modification of FIG. 58, controller 140 permits the outputting of numerical information 102a included in normal ranges 371. Controller 140 prohibits the outputting of numerical information 102a outside first determination ranges 350, numerical information 102a within first erroneous ranges 372, numerical information 102a within second erroneous ranges 373, and numerical information 102a in the case of a fractionation error. Controller 140 substitutes numerical information 102a for substitute indication 313 as in FIG. 56, where the outputting of the numerical information is prohibited. In the first modification, controller 140 permits the outputting of information 102b indicating the type of the abnormality, out of analysis results 102.

In the case of a second modification of FIG. 58, controller 140 permits the outputting of numerical information 102a included in normal ranges 371. Controller 140 prohibits the outputting of numerical information 102a outside first determination ranges 350, numerical information 102a within first erroneous ranges 372, numerical information 102a within second erroneous ranges 373, and numerical information 102a in the case of a fractionation error. Controller 140 does not display numerical information 102a on printed sheet 300, where the outputting of the numerical information is prohibited. To be more specific, numerical information 102*a* not within normal ranges 371 is not printed on printed sheet 300 as in FIG. 57. In the second modification, controller 140 also prohibits the outputting of information 102*b* indicating the type of the abnormality, out of analysis results 102. Thus, in the second modification, when an analysis item having numerical information 102*a* outside normal ranges 371 is obtained, all of its item name, numerical information 102*a*, and information 102*b* indicating the type of the abnormality are removed from printed sheet 300, and the item itself is not printed.

Additionally, the initial test and the retest are not distinguished in the first modification and the second modification of FIG. 58. To be more specific, in the initial test, if numerical information 102*a* is included in first erroneous ranges 372, the outputting of numerical information 102*a* is prohibited and printed sheet 300 is outputted.

(Error Display of Display Unit)

Subsequently, an error display of display unit 131 is described. If analysis results 102 include an abnormal value, controller 140 causes print unit 135 to print information 102*b* indicating the type of the abnormality as analysis results 102, and if there is an error with the apparatus other than with analysis results 102, the controller causes display unit 131 to display information indicating there is an error. Analysis results 102 are outputted collectively on printed sheet 300, and display unit 131 displays information other than on analysis results 102. Information displayed by display unit 131 includes information on instructions concerning the series of operations illustrated in FIG. 7 to FIG. 48, and on an apparatus error. This causes the ordering doctor or the like to surely recognize an error relating to analysis results 102 by handing over printed sheet 300 from the operator to the ordering doctor or the like, because the error relating to analysis results 102 is printed by print unit 135. On the other hand, display unit 131 displays an apparatus error which is not necessarily notified to the ordering doctor or the like. Thus, information unnecessary for diagnosis does not have to be printed on printed sheet 300.

To be more specific, display unit 131 displays information indicating there is an error if there is an error with the apparatus other than with analysis results 102. Thus, print unit 135 prints an error with analysis results 102, and display unit 131 displays an apparatus error. An apparatus error is not printed by print unit 135, but is displayed by display unit 131.

Figure 59:
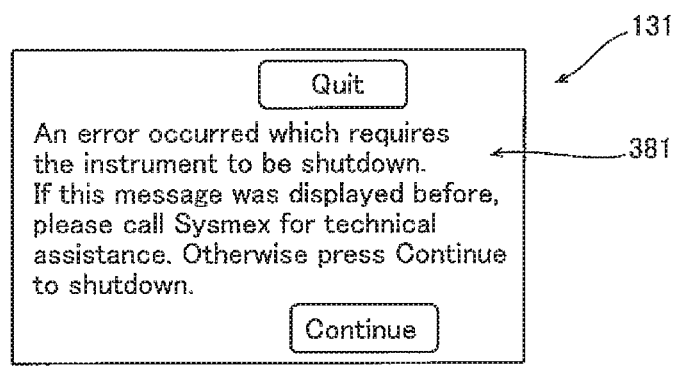
FIG. 59 is a diagram illustrating an example of an error display screen.

Display unit 131 displays information indicating there is an error for at least one of an error with analysis unit 120 and an error with a quality control process of analysis unit 120, for example. This makes it possible for the user to recognize an error relating to analysis operations or analysis quality displayed on display unit 131. In analysis unit 120, when there is an error in e.g. drive mechanism 122, fluid circuit 124, or detector 123, controller 140 causes display unit 131 to display information 381 indicating there is an error as illustrated in FIG. 59. In addition, in the quality control process, for example, controller 140 causes display unit 131 to display information (screen P117) indicating there is an error illustrated in FIG. 30 when the quality control process fails such as when an analysis result of a QC reagent exceeds a reference range set for the QC reagent.

Second Embodiment

Figure 60:
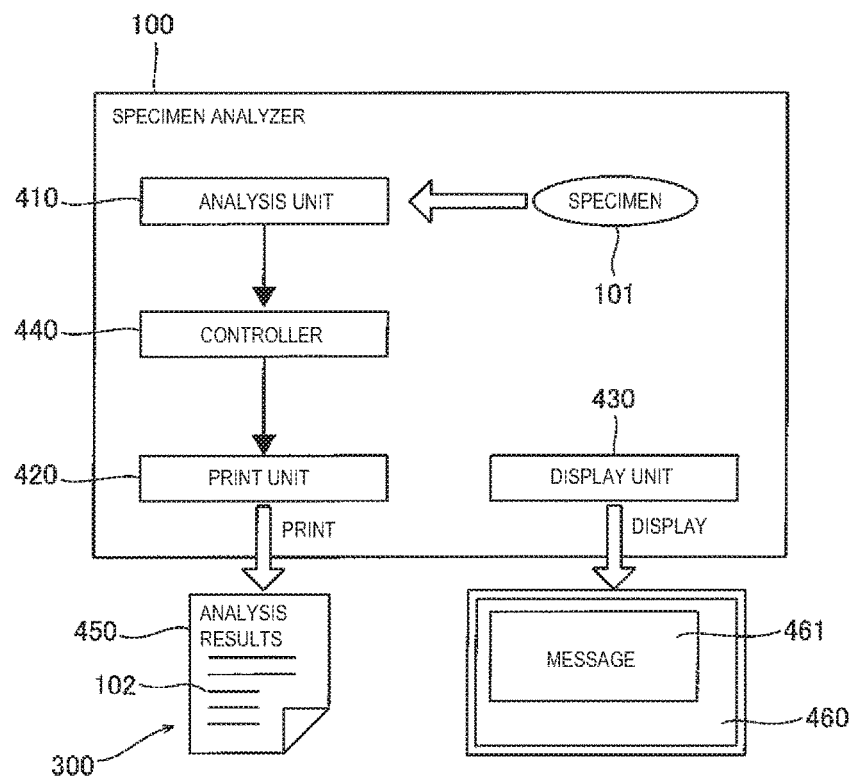
FIG. 60 is a diagram for explaining an overview of a specimen analyzer and a specimen analysis method of a second embodiment.
Figure 61:
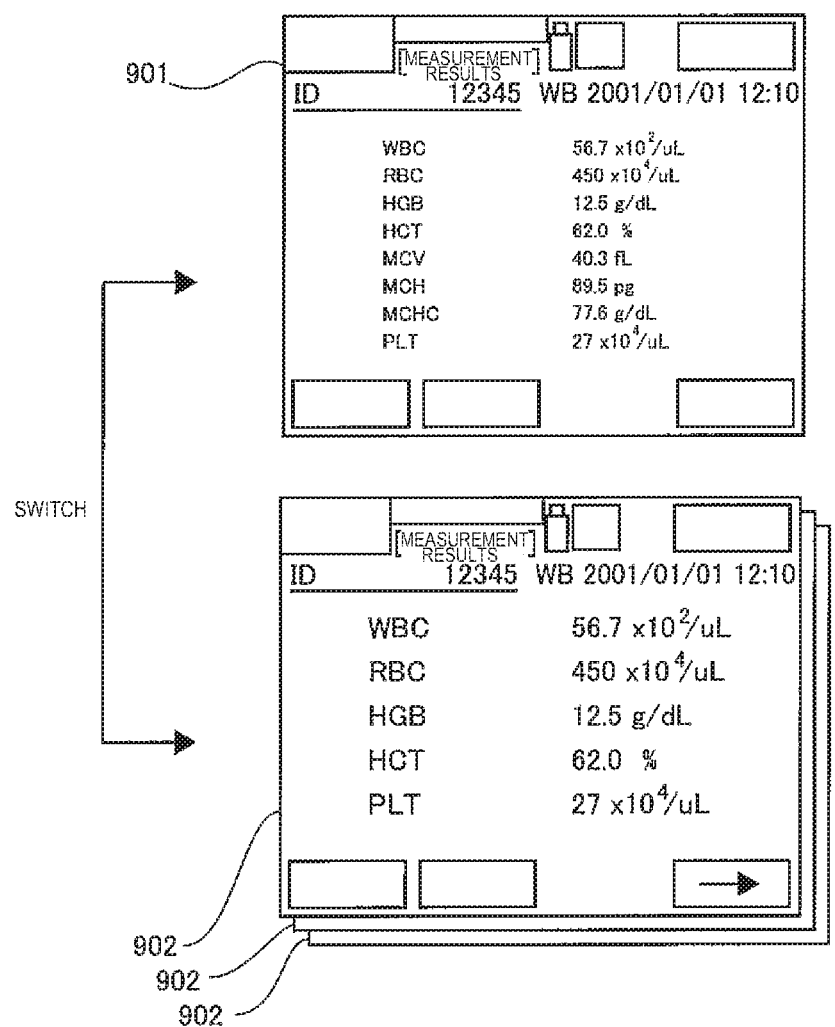
FIG. 61 is a diagram for explaining related art.
Figure 30:
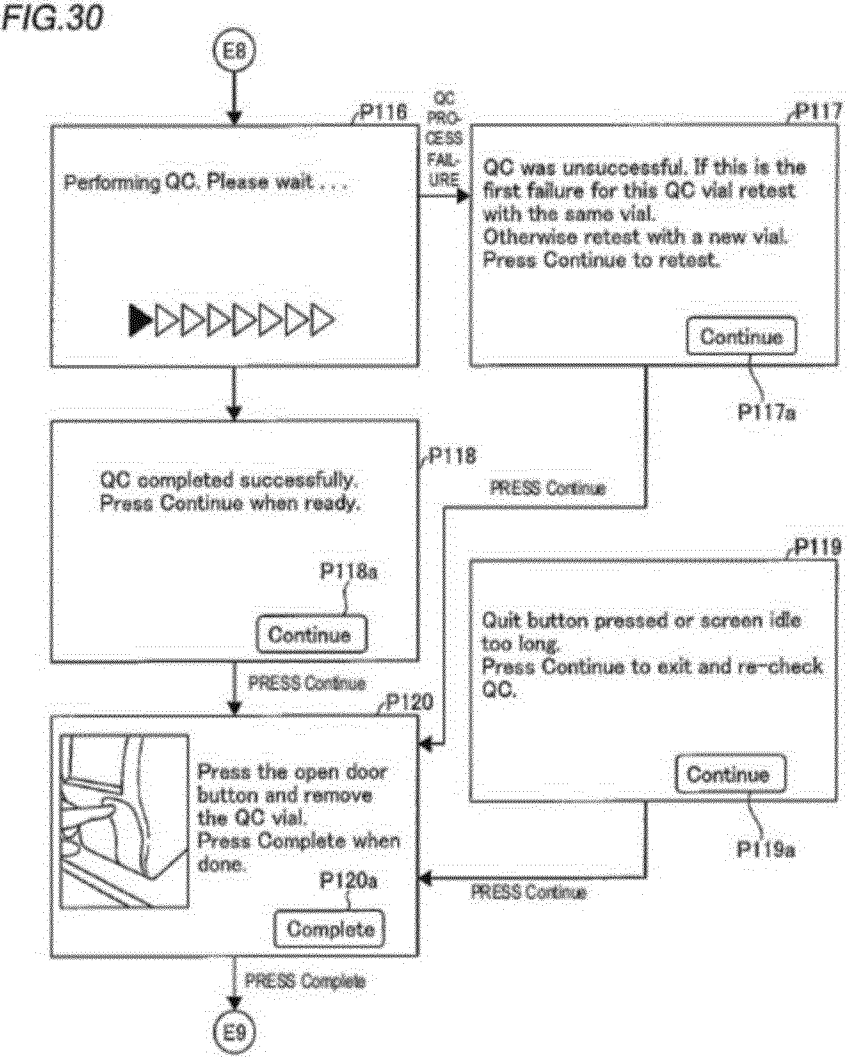
Figure 42:
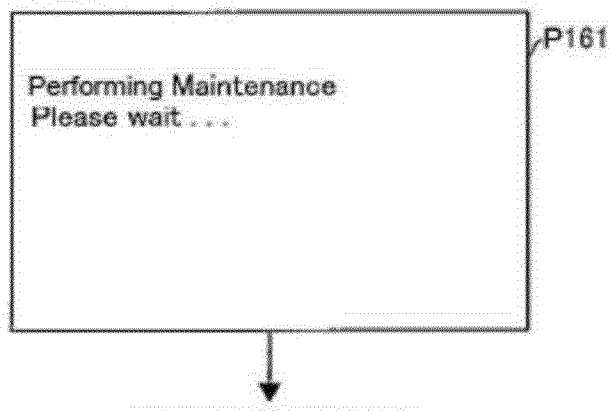
Figure 43:
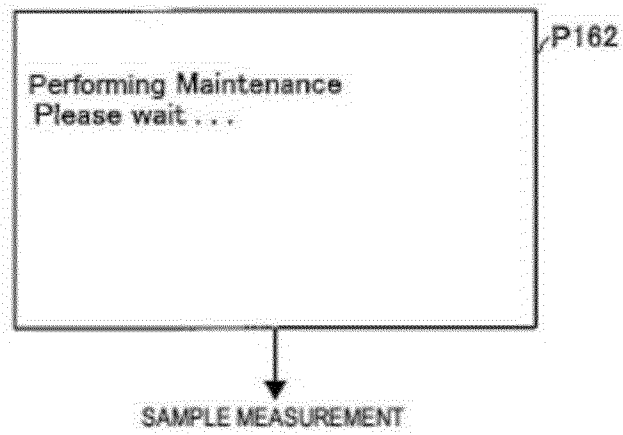

With reference to FIG. 60, a second embodiment is described. Specimen analyzer 100 of the second embodiment includes analysis unit 410, print unit 420 for printing on print sheet 450, display unit 430 for displaying an operation screen, and controller 440. The structures of analysis unit 410, print unit 420, display unit 430, and controller 440 are the same as those of the first embodiment described above.

Unlike the first embodiment described above where controller 40 is provided which performs control of causing print unit 20 to print analysis results 102 of analysis unit 10, and prohibiting display unit 30 from displaying analysis results 102, in specimen analyzer 100 of second embodiment, controller 440 performs control of causing print unit 420 to print analysis results 102 of analysis unit 410, and causing display unit 430 to display notification message 461 indicating that printed sheet 300, on which analysis results 102 has been printed, is to be outputted.

Thus, in the second embodiment illustrated in FIG. 60, display unit 430 may be caused to display analysis results 102 if display unit 430 is caused to display message 461 along with the printing of analysis results 102. Display unit 430 displays, on display screen 460, notification message 461 indicating that printed sheet 300, on which analysis results 102 has been printed, is to be outputted.

For example, notification message 461 indicating that printed sheet 300 is to be outputted may be a message meaning "printed sheet is to be outputted," a message meaning "printed sheet is being outputted," or a message saying "please check the analysis results on the outputted printed sheet." For example, FIG. 39 illustrates an example where controller 140 performs control of causing print unit 135 to print analysis results 102 of analysis unit 120, and causing display unit 131 to display a notification message to output printed sheet 300 on which analysis results 102 are printed. To be more specific, in screen P154 of FIG. 39, controller 140 displays a message to print analysis results 102 when Continue button P154*a* is pressed. Also, in screen P155, controller 140 displays a notification message indicating that printed sheet 300 is being outputted. In the second embodiment too, the content of message 461 is the same as that of screen P154 and screen P155.

As described above, in specimen analyzer 100 of the second embodiment, analysis results 102 are printed on print sheet 450 by print unit 420. Although the size of the display screen displayable at one time by display unit 430 is limited, the print area of print unit 420 can be adjusted as desired by, for example, changing the size of print sheet 450. Thus, it is possible to print analysis results 102 without making the font size small. Further, by message 461 displayed by display unit 430, the user is allowed to recognize that analysis results 102 are outputted as printed sheet 300. As a result, it is possible to prevent erroneous recognition of analysis results 102 attributed to low visibility and overlooking of analysis results 102 by the user, even in the case of small display screen 460.

There is a case where the operator of the apparatus directly communicates analysis results 102 to the ordering doctor or the like. In that case, by printing analysis results 102, the user such as an operator can hand in printed sheet 300 to the ordering doctor or the like without any modifications. Thus, miscommunication of analysis results 102 to the ordering doctor can be prevented.

Moreover, in the first embodiment, specimen analyzer 100 performs the following specimen analysis method. To be more specific, specimen analyzer 100 analyzes specimen 101 collected from the subject. Specimen analyzer 100 causes print unit 420 to print analysis results 102 on print sheet 450. Specimen analyzer 100 causes display unit 430 to display notification message 461 to output printed sheet 300 on which analysis results 102 are printed.

Thus, in the specimen analysis method of the second embodiment, analysis results 102 are printed on print sheet 450 by print unit 420. Although the size of the display screen displayable at one time by display unit 430 is limited, the print area of print unit 420 can be adjusted as desired by, for example, changing the size of print sheet 450. Thus, it is possible to print analysis results 102 without making the font size small. Further, by message 461 displayed by display unit 430, the user is allowed to recognize that analysis results 102 are outputted as printed sheet 300. As a result, it is possible to prevent erroneous recognition of analysis results 102 attributed to low visibility and overlooking of analysis results 102 by the user, even in the case of small display screen 460. There is a case where the operator of the apparatus directly communicates analysis results 102 to the ordering doctor or the like. In that case, by printing analysis results 102, the user such as an operator can hand in printed sheet 300 to the ordering doctor or the like without any modifications. Thus, miscommunication of analysis results 102 to the ordering doctor can be prevented.

Other configurations of the second embodiment are the same as those of the first embodiment described above. Thus, in the second embodiment too, the configuration illustrated in FIG. 2 to FIG. 4 can be adopted as the apparatus configuration of specimen analyzer 100. Additionally, the configuration illustrated in FIG. 4 to FIG. 48 and FIG. 59 can be adopted as the operations and control of specimen analyzer 100. Moreover, the configuration illustrated in FIG. 49 to FIG. 58 can be adopted as the print content and the printing rules for analysis results 102. Furthermore, the content of notification message 461 to output printed sheet 300 on which analysis results 102 are printed may be content other than the content illustrated in screen P154 and screen P155 of FIG. 39.

Note that the embodiments disclosed herein should be considered illustrative and non-limited in all respects. The scope of the invention is given by the scope of claims, not by the description of the embodiments described above, and moreover includes all modifications (modified examples) within the meaning and the scope equivalent to the scope of claims.

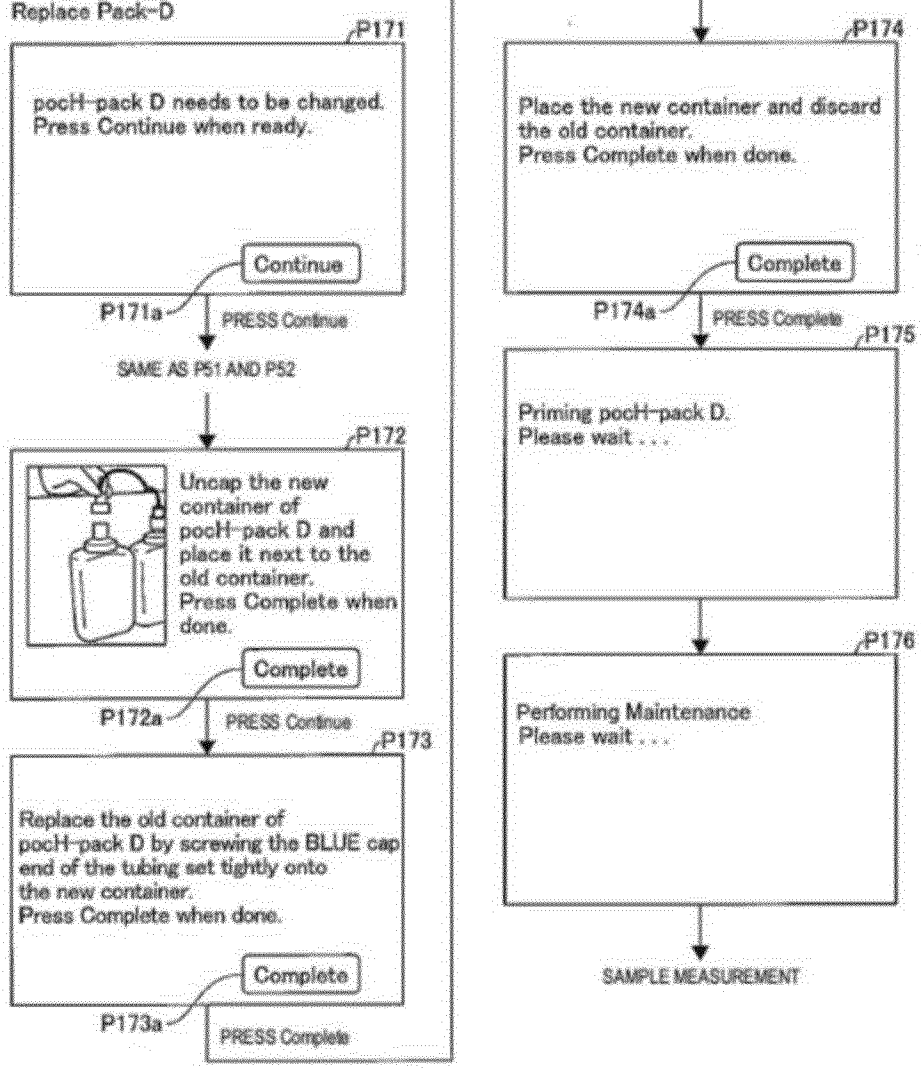

The invention claimed is:

1. A specimen analyzer comprising:
one or more detectors that measure target components in a specimen collected from a subject;
a printer that prints on a print sheet;
a display that displays an operation screen; and
a processor programmed to: cause the printer to print a result of the measurement by the one or more detectors, and cause the display to display only information other than the result of the measurement, wherein
the processor is programmed to cause the printer to print the result of the measurement by the one or more detectors and to cause the display to display only information other than the result of the measurement, so as to prevent erroneous recognition of the result of the measurement due to causing the display to display the result of the measurement,
the display has a size that reduces recognition of the result of the measurement, and
the processor is programed to cause the printer to print the result of the measurement and to cause the display having the size, to display only information other than the result of the measurement such that recognition of the printed result of the measurement is increased.

2. The specimen analyzer according to claim 1, wherein the printer is capable of changing a size of the print sheet, and prints the result of the measurement on a same surface of a single piece of the print sheet.

3. The specimen analyzer according to claim 2, wherein the printer includes a sheet set unit which holds the print sheet which is elongated, and
the printer changes the size of the print sheet by printing on an area of the print sheet with any length depending on a print amount.

4. The specimen analyzer according to claim 1, wherein the one or more detectors are configured to perform measurement for, measurement items, and
the processor is programmed to cause the printer to print the result of the measurement for each of the measurement items.

5. The specimen analyzer according to claim 1, wherein the processor is programmed to cause the printer to print, in addition to the result of the measurement, a measurement date, operator information on an operator in charge of measurement, and subject attribute information on the subject from which the specimen is collected.

6. The specimen analyzer according to claim 5, wherein the subject attribute information includes at least one of date of birth, age, and sex.

7. The specimen analyzer according to claim 1, wherein the processor is programmed to cause the printer to print, in addition to the result of the measurement, reference value information to evaluate the result of the measurement.

8. The specimen analyzer according to claim 7, wherein the reference value information is information on a numerical range indicating a normal range of the result of the measurement.

9. The specimen analyzer according to claim 7, wherein the processor is programmed to:
select the reference value information from among two or more types of reference value information depending on subject attribute information on the subject from which the specimen is collected; and
cause the printer to print the subject attribute information and the reference value information corresponding to the subject attribute information among the two or more types of reference value information.

10. The specimen analyzer according to claim 9, wherein if the result of the measurement includes an abnormal value, the processor is programmed to cause the printer to print a predetermined message,
the result of the measurement, the subject attribute information, the reference value information, and the predetermined message on a same surface of a single piece of the print sheet.

11. The specimen analyzer according to claim 10, wherein the predetermined message includes a message prompting further testing.

12. The specimen analyzer according to claim 11, wherein the processor is programmed to cause the printer to print the predetermined message subsequent to the result of the measurement on the print sheet.

13. The specimen analyzer according to claim 1, wherein the processor is programmed to:
cause the display to display a print operation screen for starting of printing of the result of the measurement; and cause the printer to start the printing of the result of the measurement based on an operation in accordance with the print operation screen.

14. The specimen analyzer according to claim 13, wherein the processor is programmed to cause the display to display, in the print operation screen, operational guidance and an instruction on how to deal with a printed sheet after printing.

15. The specimen analyzer according to claim 14, wherein the instruction on how to deal with the printed sheet includes a message instructing to deliver delivery of the printed sheet to an ordering doctor.

16. The specimen analyzer according to claim 1, wherein the processor is programmed to disable the one or more detectors from measuring a next specimen until the printer completes printing of the result of the measurement.

17. The specimen analyzer according to claim 1, wherein if the result of the measurement includes an abnormal value, the processor is programmed to cause the display to display an abnormal value notification screen to report that the abnormal value is included, and the one or more detectors are capable of retesting the same specimen if an operation in accordance with the abnormal value notification screen is performed.

18. The specimen analyzer according to claim 17, wherein if the result of the measurement includes an abnormal value, the processor is programmed to:

prohibit the printer from printing the result of the measurement, and cause a message prompting performance of retesting to be shown on the abnormal value notification screen.

19. The specimen analyzer according to claim 17, wherein the processor is further programmed to perform operations comprising:

if the result of the measurement in an initial measurement matches the result of the measurement in a retest, causing the printer to print the result of the measurement, and if the result of the measurement in the initial measurement does not match the result of the measurement in the retest, prohibiting the printer from printing the mismatched result of the measurement.

20. The specimen analyzer according to claim 1, wherein if the result of the measurement includes an abnormal value, the processor is further programmed to cause the printer to print information indicating a type of an abnormality as the result of the measurement.

21. The specimen analyzer according to claim 20, wherein if the abnormal value included in the result of the measurement is within a preset predetermined numerical range, the processor excludes the abnormal value in the result of the measurement from printing.

22. The specimen analyzer according to claim 21, wherein in a case of excluding the abnormal value from printing, the processor is further programmed to cause a substitute indication to be printed in place of the abnormal value.

23. The specimen analyzer according to claim 1, wherein the processor is further programmed to perform operations comprising:

if the result of the measurement includes an abnormal value, causing the printer to print information indicating a type of an abnormality as the result of the measurement, and if there is an error other than the result of the measurement in the specimen analyzer, causing the display to display information indicating that there is the error.

24. The specimen analyzer according to claim 23, wherein the processor is further programmed to cause the display to display information that there is the error in at least one of the one or more detectors and a quality control process of the one or more detectors.

25. The specimen analyzer according to claim 1, wherein the specimen comprises blood, and the processor is further programmed to analyze a number of blood cells and a concentration of a component contained in blood.

26. The specimen analyzer according to claim 1, wherein the processor is further programmed not to proceed to a next process until the print sheet is set in the printer.

27. A specimen measurement method in a specimen analyzer which includes a printer and a display, the method comprising:

measuring a specimen collected from a subject;

causing the printer to print a result of the measurement on a print sheet; and causing the display to display only information other than the result of the measurement, wherein causing the printer to print the result of the measurement and causing the display to display only information other than the result of the measurement, prevents erroneous recognition of the result of the measurement due to causing the display to display the result of the measurement, the display has a size that reduces recognition of the result of the measurement, and a processor is programmed to cause the printer to print the result of the measurement and to cause the display having the size, to display only information other than the result of the measurement such that recognition of the printed result of the measurement is increased.

28. A specimen analyzer comprising:

one or more detectors that measure target components in a specimen collected from a subject; and a printer that prints on a print sheet;

a display that displays an operation screen; and a processor programmed to:

cause the printer to print a result of the measurement by the one or more detectors, cause the display to display only information other than the result of the measurement, and cause the display to display a notification message indicating that a printed sheet, on which the result of the measurement has been printed, is to be outputted by the printer, wherein the processor is programmed to cause the printer to print the result of the measurement by the one or more detectors and to cause the display to display only information other than the result of the measurement, so as to prevent erroneous recognition of the result of the measurement due to causing the display to display the result of the measurement, the display has a size that reduces recognition of the result of the measurement, and the processor is programed to cause the printer to print the result of the measurement and to cause the display having the size, to display only information other than the result of the measurement such that recognition of the printed result of the measurement is increased.

29. A specimen measurement method in a specimen analyzer which includes a printer and a display, the method comprising:
   measuring a specimen collected from a subject;
   causing the printer to print a result of the measurement by one or more detectors on a print sheet;
   causing the display to display only information other than the result of the measurement; and
   causing the display to display a notification message indicating that a printed sheet, on which the result of the measurement by the one or more detectors has been printed, is to be outputted,
   wherein
   causing the printer to print the result of the measurement and causing the display to display only information other than the result of the measurement prevents erroneous recognition of the result of the measurement due to causing the display to display the result of the measurement,
   the display has a size that reduces recognition of the result of the measurement, and
   a processor is programed to cause the printer to print the result of the measurement and to cause the display having the size, to display only information other than the result of the measurement such that recognition of the printed result of the measurement is increased.

30. A specimen analyzer comprising:
   one or more detectors that measure target components in a specimen collected from a subject; and
   a printer that prints on a print sheet;
   a display that displays an operation screen; and
   a processor programmed to:
   cause the display to display only information other than a result of the measurement by the one or more detectors,
   cause the display to automatically display a print operation screen for starting printing of the result of the measurement by the one or more detectors in response to a completion of the measurement by the one or more detectors, and
   cause the printer to start the printing of the result of the measurement by the one or more detectors, in response to an operation in accordance with the print operation screen, wherein
   the processor is programmed to cause the display to display only information other than the result of the measurement and to cause the printer to print the result of the measurement by the one or more detectors, to prevent erroneous recognition of the result of the measurement due to causing the display to display the result of the measurement,
   the display has a size that reduces recognition of the result of the measurement, and
   the processor is programed to cause the printer to print the result of the measurement and to cause the display having the size, to display only information other than the result of the measurement such that recognition of the printed result of the measurement is increased.

31. The specimen analyzer according to claim 1, wherein the result of the measurement includes a plurality of measurement values corresponding to a plurality of measurement items.

32. The specimen analyzer according to claim 1, further comprising
   an analyzer body accommodating the one or more detectors and the processor, wherein
   a container set unit is provided at a front portion of the analyzer body and configured to receive a specimen container set by a user,
   the display is provided at the front portion of the analyzer body so as to be located higher than the container set unit, and
   the printer is located on an upper surface of analyzer body.

33. The specimen analyzer according to claim 1, wherein the processor is programmed not to cause the display to display the result of the measurement by the one or more detectors.

34. The specimen analyzer according to claim 1, wherein the processor is programed to cause the printer to print the result of the measurement and to cause the display to display only information other than the result of the measurement, based on the result of the measurement indicating a normal condition of the specimen.

35. The specimen analyzer according to claim 1, wherein the processor is programed to cause the printer to print the result of the measurement and to cause the display to display only information other than the result of the measurement, based on the result of the measurement indicating an abnormal condition of the specimen.

36. The specimen analyzer according to claim 1, wherein the processor is programed to cause the printer to print the result of the measurement and to cause the display to display only information other than the result of the measurement such that a printed record of the result of the measurement is provided.

* * * * *

UNITED STATES PATENT AND TRADEMARK OFFICE
CERTIFICATE OF CORRECTION

PATENT NO.        : 10,192,637 B2
APPLICATION NO.   : 15/609711
DATED             : January 29, 2019
INVENTOR(S)       : Seiji Takemoto et al.

It is certified that error appears in the above-identified patent and that said Letters Patent is hereby corrected as shown below:

In the Drawings

The word "Paforming" is changed to "Performing" in FIGs. 21, 25, 30, 42, 43 and 44 as reflected in the following sheets.

Signed and Sealed this
Eighteenth Day of February, 2020

Andrei Iancu
*Director of the United States Patent and Trademark Office*

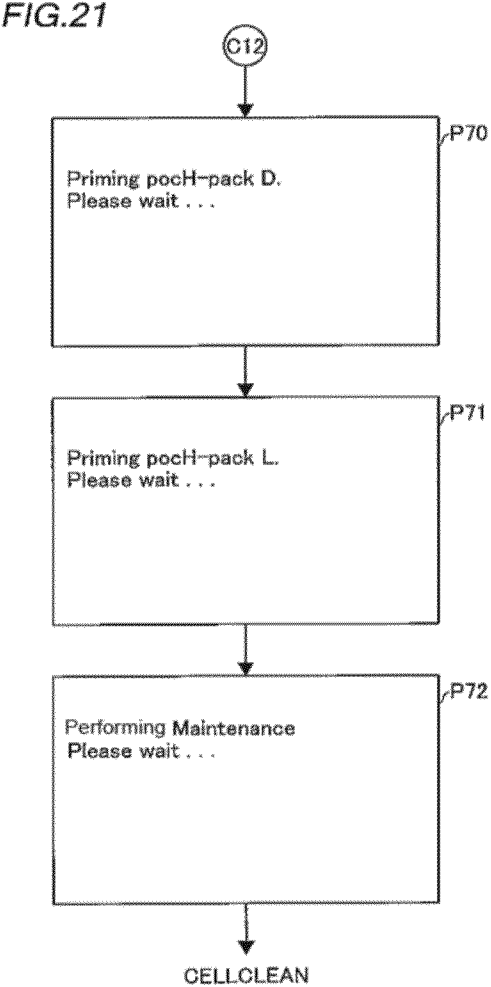

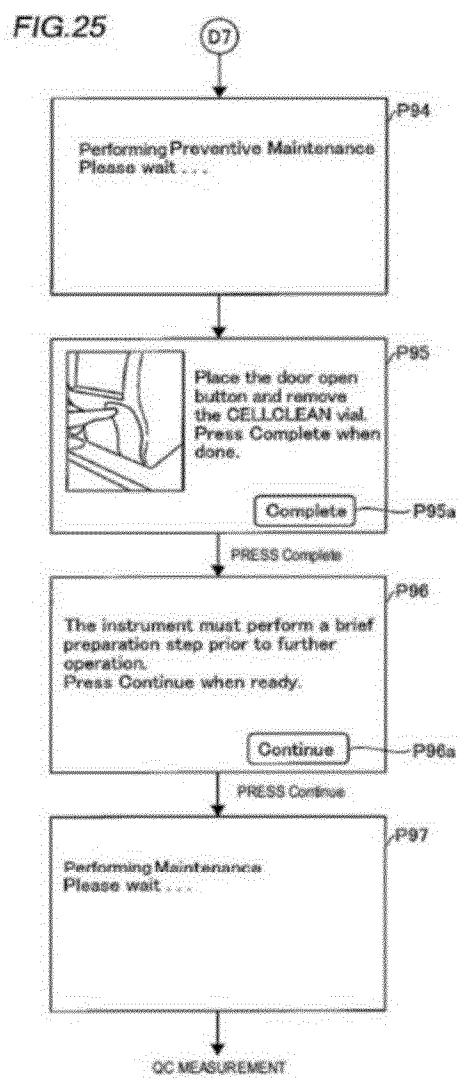

Auto Rinse

Remove Clog